United States Patent
Borras et al.

(10) Patent No.: US 10,590,193 B2
(45) Date of Patent: *Mar. 17, 2020

(54) STABLE AND SOLUBLE ANTIBODIES INHIBITING VEGF

(71) Applicant: ESBATech, an Alcon Biomedical Research Unit LLC, Schlieren (CH)

(72) Inventors: Leonardo Borras, Schlieren (CH); David Urech, Hombrechtikon (CH); Tea Gunde, Zurich (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,784

(22) Filed: Nov. 16, 2017

(65) Prior Publication Data

US 2018/0072802 A1    Mar. 15, 2018

Related U.S. Application Data

(62) Division of application No. 14/741,430, filed on Jun. 16, 2015, now Pat. No. 9,873,737, which is a division of application No. 13/708,575, filed on Dec. 7, 2012, now Pat. No. 9,090,684, which is a division of application No. 13/000,423, filed as application No. PCT/CH2009/000220 on Jun. 25, 2009, now Pat. No. 8,349,322.

(60) Provisional application No. 61/155,041, filed on Feb. 24, 2009, provisional application No. 61/075,692, filed on Jun. 25, 2008, provisional application No. 61/075,697, filed on Jun. 25, 2008, provisional application No. 61/133,212, filed on Jun. 25, 2008.

(51) Int. Cl.
| | | |
|---|---|---|
| C07K 16/22 | (2006.01) | |
| A61K 39/395 | (2006.01) | |
| C12N 15/63 | (2006.01) | |
| C07H 21/00 | (2006.01) | |
| C07K 1/00 | (2006.01) | |
| C07K 7/06 | (2006.01) | |

(52) U.S. Cl.
CPC ........... *C07K 16/22* (2013.01); *C07K 1/00* (2013.01); *C07K 7/06* (2013.01); C07K 2317/24 (2013.01); C07K 2317/54 (2013.01); C07K 2317/55 (2013.01); C07K 2317/56 (2013.01); C07K 2317/565 (2013.01); C07K 2317/567 (2013.01); C07K 2317/622 (2013.01); C07K 2317/73 (2013.01); C07K 2317/92 (2013.01)

(58) Field of Classification Search
CPC ........... C07K 16/22; C07K 2317/56; C07K 2317/55; C07K 2317/54; C07K 2317/92; C07K 2317/622; C07K 2317/567; C07K 2317/565; C07K 2317/24; A61K 39/395; C12N 15/63; C07H 21/00
See application file for complete search history.

(56) References Cited

U.S. PATENT DOCUMENTS

| | | |
|---|---|---|
| 4,376,110 A | 3/1983 | David et al. |
| 4,881,175 A | 11/1989 | Ladner |
| 4,946,778 A | 8/1990 | Ladner et al. |
| 5,013,653 A | 5/1991 | Huston et al. |
| 5,091,513 A | 2/1992 | Huston et al. |
| 5,132,405 A | 7/1992 | Huston |
| 5,225,539 A | 7/1993 | Winter |
| 5,260,203 A | 9/1993 | Ladner et al. |
| 5,258,498 A | 11/1993 | Huston et al. |
| 5,455,030 A | 10/1995 | Ladner et al. |
| 5,476,786 A | 12/1995 | Huston |
| 5,482,858 A | 1/1996 | Huston et al. |
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,730,977 A | 3/1998 | Ooka et al. |
| 5,859,205 A | 1/1999 | Adair et al. |
| 6,180,370 B1 | 1/2001 | Queen et al. |
| 6,342,219 B1 | 1/2002 | Thorpe et al. |
| 6,342,221 B1 | 1/2002 | Thorpe et al. |
| 6,407,213 B1 | 6/2002 | Carter et al. |
| 6,416,758 B1 | 7/2002 | Thorpe et al. |
| 6,524,583 B1 | 2/2003 | Thorpe et al. |
| 6,548,640 B1 | 4/2003 | Winter |
| 6,576,941 B1 | 6/2003 | Lee et al. |
| 6,632,927 B2 | 10/2003 | Adair et al. |
| 6,639,055 B1 | 10/2003 | Carter et al. |
| 6,703,020 B1 | 3/2004 | Thorpe et al. |
| 6,815,540 B1 | 11/2004 | Pluckthun et al. |
| 6,887,468 B1 | 5/2005 | Thorpe et al. |
| 6,982,321 B2 | 1/2006 | Winter |
| 6,986,890 B1 | 1/2006 | Kenya et al. |
| 7,022,500 B1 | 4/2006 | Queen et al. |
| 7,052,693 B2 | 5/2006 | Shitara et al. |
| 7,056,509 B2 | 6/2006 | Thorpe et al. |

(Continued)

FOREIGN PATENT DOCUMENTS

| | | |
|---|---|---|
| EP | 1179541 B1 | 6/2004 |
| EP | 0817648 B1 | 12/2004 |

(Continued)

OTHER PUBLICATIONS

Vascular endothelial growth factor A isoform b [*Homa sapiens*], NCBI Refrence Sequence: NP_003367.4; downloaded https://www.ncbi.nim.nih.gov/protein/NP_003367 Apr. 22, 2007.

(Continued)

*Primary Examiner* — Phuong Huynh
(74) *Attorney, Agent, or Firm* — Jason J. Derry

(57) ABSTRACT

The present invention relates to soluble and stable anti-VEGF imunobinders comprising CDRs from rabbit monoclonal antibodies. Said antibodies are designed for the diagnosis and/or treatment of VEGF-mediated disorders. The hybridomas, nucleic acids, vectors and host cells for expression of the recombinant antibodies of the invention, methods for isolating them and the use of said antibodies in medicine are also disclosed.

14 Claims, 27 Drawing Sheets

Specification includes a Sequence Listing.

(56) References Cited

U.S. PATENT DOCUMENTS

| | | | |
|---|---|---|---|
| 7,227,004 B2 | 6/2007 | Kim | |
| 7,241,877 B2 | 7/2007 | Adair et al. | |
| 7,244,615 B2 | 7/2007 | Adair et al. | |
| 7,244,832 B2 | 7/2007 | Adair et al. | |
| 7,262,050 B2 | 8/2007 | Adair et al. | |
| 7,375,193 B2 | 5/2008 | Baca et al. | |
| 7,482,005 B2 | 1/2009 | Kim | |
| 7,803,371 B2 | 9/2010 | Ke et al. | |
| 8,349,322 B2 * | 1/2013 | Borras | C07K 16/22 424/130.1 |
| 9,090,684 B2 * | 7/2015 | Borras | C07K 16/22 |
| 9,873,737 B2 * | 1/2018 | Borras | C07K 16/22 |
| 2003/0023046 A1 | 1/2003 | Ferrara et al. | |
| 2005/0033031 A1 | 2/2005 | Couto | |
| 2005/0048578 A1 | 3/2005 | Zhang | |
| 2006/0099204 A1 | 5/2006 | Couto et al. | |
| 2006/0280747 A1 | 12/2006 | Fuh et al. | |
| 2007/0020267 A1 | 1/2007 | Fuh et al. | |
| 2007/0190058 A1 | 8/2007 | Shams | |
| 2008/0112952 A1 | 5/2008 | Finger | |
| 2008/0226629 A1 | 9/2008 | Baca et al. | |
| 2008/0248033 A1 | 10/2008 | Ferrara et al. | |
| 2009/0081232 A1 | 3/2009 | Kim | |

FOREIGN PATENT DOCUMENTS

| | | |
|---|---|---|
| EP | 1627643 A2 | 2/2006 |
| EP | 1238986 B1 | 6/2008 |
| EP | 1975181 B1 | 2/2011 |
| WO | 198906692 | 7/1989 |
| WO | 199101753 | 2/1991 |
| WO | 9845331 | 10/1998 |
| WO | 0130393 A2 | 5/2001 |
| WO | 200148017 A1 | 7/2001 |
| WO | WO2003/060672 | 10/2003 |
| WO | 2003097697 A1 | 11/2003 |
| WO | 2004016740 A | 2/2004 |
| WO | 2005000900 A1 | 1/2005 |
| WO | 2005012359 A2 | 2/2005 |
| WO | 2005016950 A1 | 2/2005 |
| WO | 2005054273 A2 | 6/2005 |
| WO | 2006/012688 A1 | 2/2006 |
| WO | 2006047325 A1 | 5/2006 |
| WO | 2006050491 A2 | 5/2006 |
| WO | 2009000099 A2 | 12/2006 |
| WO | 2007019620 A1 | 2/2007 |
| WO | 2007089445 A2 | 8/2007 |
| WO | 2008006235 A2 | 1/2008 |
| WO | 2008063932 A2 | 5/2008 |
| WO | 2008110348 A1 | 9/2008 |
| WO | 2008149147 A2 | 12/2008 |
| WO | 2008149148 A2 | 12/2008 |
| WO | 2009000098 A2 | 12/2008 |
| WO | 2009155724 A1 | 12/2009 |
| WO | 2009155725 A1 | 12/2009 |
| WO | 2009155726 A2 | 12/2009 |

OTHER PUBLICATIONS

Asano et al, "An antihuman VEGF monoclonal antibody MV833 that exhibits potent anti-tumor activity in vivo", Hybridoma, 1998, vol. 17 (2), pp. 185-190.

Boulton et al, "VEGF localisation in diabetic retinopathy", Ophthalmol, 1998, vol. 82, pp. 561-568.

Moore et al, "Kinetics and thermodynamics of dimer formation and dissociation for a recombinant humanized monoclonal antibody to vascular endothelial growth factor", Biochemistry, 1999, vol. 38 (42), pp. 13960-13967.

Muller et al., "VEGF and the Fab fragment of a humanized neutralizing antibody: crystal structure of the complex at 2.4 A resolution and mutational analysis of the interface", Strucutre, 1998, vol. 6, No. 9, pp. 1153-1167.

Ran et al.; "Generation of new rabbit monoclonal antibody RAM-1 against human VEGF-C"; Proceedings of the annual meetings of the American Association for Cancer; Tumor Biology; vol. 46; p. 911 (2005).

Riechmann et al.; "Reshaping human antibodies for therapy"; Nature; vol. 332; pp. 323-327 (Mar. 1998).

Roovers and Van Der Linden; "In vitro characterization of a monovalent and bivalent form of a fully human anti-Ep-CAM phage antibody"; Cancer Immunol. Immunother; vol. 50; pp. 51-59 (2001).

Rose et al.; "Hydrophobicity of amino acid residues in globular proteins"; Science; vol. 229; pp. 834-838 (1985).

Saito, et al.; "Drug delivery strategy utilizing conjugation via reversible disulfide linkages: role and site of cellular reducing activities"; Advanced Drug Delivery Reviews; vol. 55; pp. 119-215 (2003).

Shibuya et al.; "Nucleotide sequence and expression of a novel human receptor-type tyrosine kinase gene (III) closely related to the fms family"; Oncogene; vol. 5; pp. 519-524 (1990).

Skerra and Pluckthun; "Assembly of a functional immunoglobulin Fv fragment in *Escherichia coli*"; Science; vol. 240; pp. 1038-1041 (May 20, 1988).

Terman et al.; "Identification of a new endothelial cell growth factor receptor tyrosine kinase"; Oncogene; vol. 6; pp. 1677-1683 (1991).

Terman et al.; "Identification of the KDR tyrosine kinase as a receptor for vascular endothelial cell growth factor"; Biochemical and Biophysical Research Communications vol. 187; No. 3; pp. 1579-1586 (Sep. 30, 1992).

Thorpe and Ross; "The preparation and cytotoxic properties of antibody-toxin conjugates"; Immunological Review; vol. 62; pp. 119-158 (1982).

Trail et al.; "Monoclonal antibody drug immunoconjugates for targeted treatment of cancer"; Cancer Immunol Immunother; vol. 52; pp. 328-337 (2003).

Warren et al.; "Regulation by vascular endothelial growth factor of human colon cancer tumorigenesis in a mouse model of experimental liver metastasis"; J. Clin. Invest.; vol. 95; pp. 1789-1797 (1995).

Weidner et al.; "Tumor angiogenesis and metastasis-correlation in invasive breast carcinoma"; The New England Journal of Medicine; vol. 324; No. 1; pp. 1-6 (Jan. 3, 1991).

Zhang et al.; Antibody and Antibody Targets; Proceedings of the annual meeting of the American Assoc for Cancer Research; vol. 50; pp. 296 (Apr. 22, 2009).

Search report and Written Opinion for corresponding PCT Application No. PCT/CH2009/000220.

Maccallum et al.; "Antibody-antigen interactions: contact analysis and binding site topography"; J. Mol. Biol.; vol. 262; pp. 732-745 (1996).

Wu et al.; "Humanization of a murine monoclonal antibody by simultaneous optimization of framework and CDR residues"; J. Mol. Biol.; vol. 294; pp. 151-162 (1999).

Rossi, et al: "A comparative study between a novel category of immunoreagents and the corresponding mouse monocional antibodies", Am. J. Clin. Pathol.; 2005; pp. 295-302.

Wang et al: "The effect of antibody against vascular endothelial growth factor on tumor growth and metastasis", J. Cancer Res. Clin. Oncol.; Jan. 1998; 124-615-620.

Steinberger et al: "Generation and characterization of a recombinant human CCR5-specitic antibody", The Journal of Biological Chemistry; vol. 275, No. 46, pp. 36073-36078.

Kohno et al: "Neutralizing effects of an anti-vascular endothelial growth factor antibody on tooth movement", Angle Orthodontist, vol. 75, No. 5, 2005.

Sone et al: "Neutralization of vascular endothelial growth factor prevents collagen-induced arthritis and ameliorates established disease in mice", Biochemical and Biophysical Research Communications; Dec. 19, 2000, pp. 562-568.

Vilches-Moure et al: "Comparison of rabbit monoclonal and mouse monoclonal antibodies in immunohistochemistry in canine tissues", J. Vet. Diagn. Invest. 2005; 17:346-350.

Yu et al. Investigative Ophthalmology & Visual Science 49(2): 522-527, Feb. 2008.

Singh et al: Nature Biotechnology 30(7): 648-657, Jul. 2012.

(56) References Cited

OTHER PUBLICATIONS

Fogarty et al: The Scientist 16(16): 33, 2002.
Adamis et al.; "Inhibition of vascular endothelial growth factor prevents retinal ischemia-associated iris neovascularization in a nonhuman primate"; Arch. Ophthalmol. vol. 114; pp. 66-71 (1996).
Aiello et al.; "Vascular endothelial growth factor in ocular fluid of patients with diabetic retinopathy and other retinal disorders"; N. Engl. J. Med.; vol. 331; pp. 480-487 (1994).
Kaija Alfthan, et al., "Properties of a Single-Chain Antibody Containing Different Linker Peptides," Protein Engineering, 1995, pp. 725-731, vol. 8, No. 7.
Allen; "Ligand-targeted therapeutics in anticancer therapy"; Nature; Reviews; Cancer; vol. 2; pp. 750-763 (Oct. 2002).
Banyay et al.; "Three-dimensional imaging in in situ specimens with low-dose electron tomography to analyze protein conformation"; ASSAY and Drug Development Technologies; vol. 2; No. 5; pp. 561-567; (Nov. 5, 2004).
Berkman et al.; "Expression of the vascular permeability factor/vascular endothelial growth factor gene in central nervous system neoplasms"; J. Clin. Invest.; vol. 91; pp. 153-159 (1993).
Bird et al.; "Single-chain antigen-binding proteins"; Science; vol. 242; pp. 423-426 (Oct. 21, 1988).
Borgstrom et al.; "Complete inhibition of angiogenesis and growth of microtumors by anti-vascular endothelial growth factor neutralizing antibody: novel concepts of angiostatic therapy from intravitral videomicroscopy" Cancer Research; vol. 56; pp. 4032-4039 (Sep. 1, 1996).
Brennan et al.; "Preparation of bispecific antibodies by chemical recombination of monoclonal immunoglobulin G1 fragments"; Science; vol. 229; pp. 81-83 (1985).
Brown, et al; "Expression of vascular permeability factor (vascular endothelial growth factor) and its receptors in adenocarcinomas of the gastrointestinal tract"; Cancer Research; vol. 53; pp. 4727-4735 (Oct. 1, 1993).
Brown et al.; "Expression of vascular permeability factor (vascular endothelial growth factor) and its receptors in breast cancer"; Human Pathology; vol. 26; pp. 86-91 (1995).
Brummell et al.; "Probing the combining site of an anti-carbohydrate antibody by saturation-mutagenesis: role of the heavy-chain CDR3 residues"; Biochemistry; vol. 32; pp. 1180-1187 (1993).
Burks et al.; "In vitro scanning saturation mutagenesis of an antibody binding pocket"; Proc. Natl. Acad. Sci.; vol. 94; pp. 412-417 (Jan. 1997).
Choi et al.; "Recombinant chimeric OKT3 scFv IgM antibodies mediate immune suppression while reducing T cell activation in vitro"; Eur. J. Immunol.; vol. 31; pp. 94-106 (2001).
Cornette et al; "Hydrophobicity scales and computational techniques for detecting amphipathic structures in proteins"; J. Mol. Biol., vol. 195; pp. 659-685 (1987).
Devries et al.; "The tms-like tyrosine kinase, a receptor for vascular endothelial growth factor"; Science; vol. 255; pp. 989-991; (Feb. 21, 1992).
Dumoulin et al.; "Single-domain antibody fragments with high conformational stability" Protein Science; vol. 11; pp. 500-515; 2002).
Dvorak et al.; "Vascular permeability factor/vascular endothelial growth factor, microvascular hyperpermeability, and angiogenesis"; American Journal of Pathology; vol. 146; No. 5; pp. 1029-1039 (May 1995).
Ferrara and Davis-Smyth; "The biology of vascular endothelial growth factor"; Endocrine Reviews; vol. 18; No. 1; pp. 4-25 (Feb. 25, 2005).
Folkman and Shing; Angiogenesis; The Journal of Biological Chemistry; vol. 267; No. 16; pp. 10931-10934 (1992).
Fuh et al.; Structure-function studies of two synthetic anti-vascular endothelial growth factor fabs and comparison with the Avastin (TM) fab; The Journal of Biological Chemistry, vol. 281; No. 10; pp. 6625-6631 (Mar. 10, 2006).

Glennie et al.; "Preparation and performance of bispecific F(ab'y)2 antibody containing thioether-linked Fab'y fragments"; The Journal of Immunology; vol. 139; No. 7; pp. 2367-2375 (Oct. 1, 1987).
Hamers-Casterman et al.; "Naturally occurring antibodies devoid of light chains"; Letters to Nature; vol. 363; pp. 446-448 (Jun. 3, 1993).
Hollinger et al.; "Diabodies: small bivalent and bispecific antibody fragments"; Proc. Natl. Acad. Sci.; vol. 90; pp. 6444-6448 (Jul. 1993).
Honegger and Pluckthun; "Yet another numbering scheme for immunoglobulin variable domains: an automatic modeling and analysis tool"; J. Mol. Biol.; vol. 309; pp. 657-670 (2001).
Horak et al; "Angiogenesis, assessed by platelet/endothelial cell adhesion molecule antibodies, as indicator of node metastases and survival in breast cancer"; The Lancet; vol. 340; pp. 1120-1124 (Nov. 7, 1992).
Houck, et al.; "The vascular endothelial growth factor family: identification of a fourth molecular species and characterization of alternative splicing of RNA"; Molecular Endocrinology; vol. 5; pp. 1806-1814 (1991).
Hu et al.; "Minibody: a novel engineered anti-carcinoembryonic antigen antibody fragment (single-chain Fv-CH3) which exhibits rapid, high-level targeting of xenografts"; Cancer Research; vol. 56; pp. 3055-3061 (Jul. 1, 1996).
Huston et al.; "Protein engineering of antibody binding sites: recovery of specific activity in an anti-digoxin single-chain Fv analogue produced in *Escherichia coli*"; Proc. Natl. Acad. Sci.; vol. 85; pp. 5879-5883 (Aug. 1988).
Jones et al.; "Replacing the complementarity-determining regions in a human antibody with those from a mouse"; Nature; vol. 321; pp. 522-525 (May 1986).
Karpovsky et al.; "Production of target-specific effect or cells using hetero-cross-linked aggregates containing anti-target cell and anti-Fcy receptor antibodies"; Journal of Experimental Medicine; vol. 160; pp. 1686-1701 (Dec. 1984).
Kim et al.; "Inhibition of vascular endothelial growth factor-induced angiogenesis suppresses tumour growth in vivo"; Letters to Nature; vol. 362; pp. 841-844 (Apr. 29, 1993).
Kipriyanov et al; "Bispecific tandem diabody for tumor therapy with improved antigen binding and pharmacokinetics"; J. Mol. Biol.; vol. 293; pp. 41-56 (1999).
Klagsbrun; "Regulators of angiogenesis"; Annu. Rev. Physiol.; vol. 53; pp. 217-239 (1991).
Kobayashi et al; "Tryptophan H33 plays an important role in pyrimidine (6-4) pyrimidone photoproduct binding by a high-affinity antibody"; Protein Engineering; vol. 12; No. 10; pp. 879-884 (1999).
Leung et al.; "Vascular endothelial growth factor is a secreted angiogenic mitogen"; Science; vol. 246; pp. 1306-1309 (Dec. 8, 1989).
Liang et al.; "Cross-species vascular endothelial growth factor (VEGF)-blocking antibodies completely inhibit the growth of human tumor xenografts and measure the contribution of stromal VEGF"; The Journal of Biological Chemistry; vol. 281; No. 2; pp. 951-961 (Jan. 13, 2006).
Liu et al.; "Heteroantibody duplexes target cells for lysis by cytotoxic T lymphocytes"; Proc. Natl. Acad. Sci.; vol. 82; pp. 8648-8652 (Dec. 1985).
Lopez et al.; "Transdifferentiated retinal pigment epithelial cells are immunoreactive for vascular endothelial growth factor in surgically excised age-related macular degeneration-related choroidal neovascular membranes"; Investigative Ophthalmology & Visual Science; vol. 37; No. 5; pp. 855-868 (Apr. 1996).
Macchiarini et al.; "Relation of neovascularization to metastasis of non-small-cell lung cancer"; Short Report; The Lancet; vol. 340; pp. 145-146 (Jul. 18, 1992).
Mattern et al.; "Associatin of vascular endothelial growth factor expression with intratumoral microvessel density and tumour cell proliferation in human epidermoid lung carcinoma"; British Journal of Cancer; vol. 73; pp. 931-934 (1996).

(56) References Cited

OTHER PUBLICATIONS

Matthews et al.; "A receptor tyrosine kinase cDNA isolated from a population of enriched primitive hematopoietic cells and exhibiting close genetic linkage to c-kit"; Proc. natl. Acad. Sci.; vol. 88; pp. 9026-9030 (Oct. 1991).

Melnyk et al.; "Vascular endothelial growth factor promotes tumor dissemination by a mechanism distinct form its effect on primary tumor growth"; Cancer Research; vol. 56; pp. 921-924 (Feb. 15, 1996).

Myers and Miller; "Optimal alignments in linear space"; CABIOS; vol. 4; No. 1; pp. 11-17 (1988).

Needleman and Wunsch; "A general method applicable to the search for similarities in the amino acid sequence of two proteins"; J. Mol. Biol.; vol. 48; pp. 443-453 (1970).

Pastan and Kreitman; "Overview: Immunotoxins in cancer therapy"; Current Opinion Investig. Drugs; vol. 3; pp. 1089-1091 (2002).

Paulus; "Preparation and biomedical applications for bispecific antibodies"; Behring Inst. Mitt.; No. 78; pp. 118-132 (1985).

Payne; "Progess in immunoconjugate cancer therapeutics"; Cancer Cell; vol. 3; pp. 207-212 (Mar. 2003).

Queen et al.; "A humanized antibody that binds to the interleukin 2 receptor"; Proc. Natl. Acad. Sci.; vol. 86; pp. 10029-10033 (Dec. 1989).

Rader et al.; "The rabbit antibody repertoire as a novel source for the generation of therapeutic human antibodies"; The Journal of Biological Chemistry; vol. 275; No. 18; pp. 13668-13676 (2000).

Rudikoff et al.; PNAS, vol. 79, p. 1979-1983; Mar. 1982.

Tamura et al.; J. Immunol., vol. 164, p. 1432-1441, Feb. 2000.

Muller et al., VEGF and the Fab fragment of a humanized neutralizing antibody : crystal structure of the complex at 2.4 A resolution and mutational analysis of the interface, Structure, vol. 6: 1153-1167, Sep. 15, 1998.

Mikhail Popkov et al., Human/mouse cross-reactive anti-VEGF receptor 2 recombinant antibodies selected from an immune b9 allotype rabbit antibody library, Journal of Immunological Methods, 2004, 288, pp. 149-164 (abstract).

Roitt A. et al., Immunilogy, Moscow, "MIR", 2000, pp. 97-109.

Kohno et al, Neutralizing Effects of an Anti-Vascular Endothelial Growth Factor Antibody on Tooth Movement, Angle Orthodontist, vol. 75, No. 5, pp. 797-804, 2005.

Sone et al, Neutralization of Vascular Endothelial Growth Factor Prevents Collagen-Induced Arthritis and Ameliorates Established Disease in Mice, Biochemical and Biophysical Research Communications, vol. 281, pp. 562-568, 2001.

Wang et al, The effect of antibody against vascular endothelial growth factor on tumor growth and metastasis, J. Cancer Res. Clin. Oncol., vol. 124, pp. 615-620, 1998.

\* cited by examiner

SEQUENCE LISTING

<160> NUMBER OF SEQ ID NOS: 184

<210> SEQ ID NO 1
<211> LENGTH: 11
<212> TYPE: PRT
<213> ORGANISM: Homo sapiens

<400> SEQUENCE: 1

Lys Phe Met Asp Val Tyr Gln Arg Ser Tyr Cys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 2

Gly Phe Pro Phe Ser Ser Gly Tyr Trp Val Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 3

Gly Phe Ser Phe Ser Ser Gly Tyr Trp Ile Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 4

Gly Phe Ser Leu Asn Thr Asn Tyr Trp Met Cys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 5

Gly Phe Ser Phe Ser Arg Ser Tyr Tyr Ile Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 6

Gly Phe Ser Phe Thr Thr Thr Asp Tyr Met Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 7

Gly Ile Asp Phe Ser Gly Ala Tyr Tyr Met Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 8

Gly Phe Ser Leu Thr Asp Tyr Tyr Tyr Met Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: CDR stemming from rabbit antibody

<400> SEQUENCE: 9

Gly Phe Ser Leu Ser Tyr Tyr Tyr Met Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: CDR stemming from rabbit antibody

<400> SEQUENCE: 10

Gly Phe Ser Leu Ser Asp Tyr Tyr Met Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: CDR stemming from rabbit antibody

<400> SEQUENCE: 11

Gly Phe Ser Leu Ser Ser Tyr Tyr Met Cys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: CDR stemming from rabbit antibody

<400> SEQUENCE: 12

Gly Phe Ser Leu Asn Thr Tyr Tyr Met Asn
1               5                   10

```
<210> SEQ ID NO 13
<211> LENGTH: 10
<212> TYPE: PRT
<213> ORGANISM: Artificial Sequence
<220> FEATURE:
<223> OTHER INFORMATION: CDR stemming from rabbit antibody

<400> SEQUENCE: 13

Gly Phe Ser Leu Ser Ser Tyr Tyr Met Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 14

Gly Phe Ser Leu Ser Ser Gly Tyr Tyr Met Cys
1               5                   10

<210> SEQ ID NO 15
<211> LENGTH: 18
<212> TYPE: PRT
<213> ORGANISM: Artificial Sequence
<220> FEATURE:
<223> OTHER INFORMATION: CDR stemming from rabbit antibody

<400> SEQUENCE: 15

Cys Ile Tyr Ala Gly Ser Ser Gly Ser Thr Tyr Tyr Ala Ser Trp Ala
1               5                   10                  15

Lys Gly

<210> SEQ ID NO 16
<211> LENGTH: 18
<212> TYPE: PRT
<213> ORGANISM: Artificial Sequence
<220> FEATURE:
<223> OTHER INFORMATION: CDR stemming from rabbit antibody

<400> SEQUENCE: 16

Cys Met Tyr Thr Gly Ser Tyr Asn Arg Ala Tyr Tyr Ala Ser Trp Ala
1               5                   10                  15

Lys Gly

<210> SEQ ID NO 17
<211> LENGTH: 18
<212> TYPE: PRT
<213> ORGANISM: Artificial Sequence
<220> FEATURE:
<223> OTHER INFORMATION: CDR stemming from rabbit antibody

<400> SEQUENCE: 17

Cys Ile Asp Ala Gly Ser Ser Gly Ile Leu Val Tyr Ala Asn Trp Ala
1               5                   10                  15

Lys Gly

<210> SEQ ID NO 18
<211> LENGTH: 17
<212> TYPE: PRT
<213> ORGANISM: Artificial Sequence
<220> FEATURE:
<223> OTHER INFORMATION: CDR stemming from rabbit antibody

<400> SEQUENCE: 18
```

```
Cys Ile Leu Ala Gly Asp Gly Ser Thr Tyr Tyr Ala Asn Trp Ala Lys
1               5                   10                  15
Gly
```

<210> SEQ ID NO 19
<211> LENGTH: 16
<212> TYPE: PRT
<213> ORGANISM: Artificial Sequence
<220> FEATURE:
<223> OTHER INFORMATION: CDR stemming from rabbit antibody

<400> SEQUENCE: 19

```
Tyr Ile Asp Tyr Asp Gly Asp Arg Tyr Tyr Ala Ser Trp Ala Lys Gly
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: CDR stemming from rabbit antibody

<400> SEQUENCE: 20

```
Phe Ile Asp Pro Asp Asp Asp Pro Tyr Tyr Ala Thr Trp Ala Lys Gly
1               5                   10                  15
```

<210> SEQ ID NO 21
<211> LENGTH: 16
<212> TYPE: PRT
<213> ORGANISM: Artificial Sequence
<220> FEATURE:
<223> OTHER INFORMATION: CDR stemming from rabbit antibody

<400> SEQUENCE: 21

```
Ile Ile Gly Pro Gly Asp Tyr Thr Asp Tyr Ala Ser Trp Ala Lys Gly
1               5                   10                  15
```

<210> SEQ ID NO 22
<211> LENGTH: 16
<212> TYPE: PRT
<213> ORGANISM: Artificial Sequence
<220> FEATURE:
<223> OTHER INFORMATION: CDR stemming from rabbit antibody

<400> SEQUENCE: 22

```
Cys Leu Asp Tyr Phe Gly Ser Thr Asp Ala Ser Trp Ala Lys Gly
1               5                   10                  15
```

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide

<400> SEQUENCE: 23

```
Cys Leu Asp Tyr Val Gly Asp Thr Asp Tyr Ala Ser Trp Ala Lys Gly
1               5                   10                  15
```

<210> SEQ ID NO 24
<211> LENGTH: 16
<212> TYPE: PRT
<213> ORGANISM: Artificial Sequence
<220> FEATURE:
<223> OTHER INFORMATION: CDR stemming from rabbit antibody

```
<400> SEQUENCE: 24

Ile Ile Ala Pro Asp Asp Thr Thr Tyr Tyr Ala Ser Trp Ala Lys Ser
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: CDR stemming from rabbit antibody

<400> SEQUENCE: 25

Ile Leu Asp Tyr Val Gly Asp Thr Asp Tyr Ala Ser Trp Ala Lys Gly
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: CDR stemming from rabbit antibody

<400> SEQUENCE: 26

Cys Ile Asp Ala Gly Ser Asp Gly Asp Thr Tyr Tyr Ala Ser Trp Ala
1               5                   10                  15

Lys Gly

<210> SEQ ID NO 27
<211> LENGTH: 19
<212> TYPE: PRT
<213> ORGANISM: Artificial Sequence
<220> FEATURE:
<223> OTHER INFORMATION: CDR stemming from rabbit antibody

<400> SEQUENCE: 27

Gly Asn Asn Tyr Tyr Ile Tyr Thr Asp Gly Gly Tyr Ala Tyr Ala Gly
1               5                   10                  15

Leu Glu Leu

<210> SEQ ID NO 28
<211> LENGTH: 8
<212> TYPE: PRT
<213> ORGANISM: Artificial Sequence
<220> FEATURE:
<223> OTHER INFORMATION: CDR stemming from rabbit antibody

<400> SEQUENCE: 28

Gly Ser Asn Trp Tyr Ser Asp Leu
1               5

<210> SEQ ID NO 29
<211> LENGTH: 14
<212> TYPE: PRT
<213> ORGANISM: Artificial Sequence
<220> FEATURE:
<223> OTHER INFORMATION: CDR stemming from rabbit antibody

<400> SEQUENCE: 29

Gly Asp Ala Ser Tyr Gly Val Asp Ser Phe Met Leu Pro Leu
1               5                   10

<210> SEQ ID NO 30
<211> LENGTH: 11
<212> TYPE: PRT
<213> ORGANISM: Artificial Sequence
```

```
<220> FEATURE:
<223> OTHER INFORMATION: CDR stemming from rabbit antibody

<400> SEQUENCE: 30

Ser Asp Pro Ala Ser Ser Trp Ser Phe Ala Leu
1               5                   10

<210> SEQ ID NO 31
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 31

Ser Asp Tyr Ser Ser Gly Trp Gly Thr Asp Ile
1               5                   10

<210> SEQ ID NO 32
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 32

Gly Asp His Asn Ser Gly Trp Gly Leu Asp Ile
1               5                   10

<210> SEQ ID NO 33
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 33

Gly Asp Asp Asn Ser Gly Trp Gly Glu Asp Ile
1               5                   10

<210> SEQ ID NO 34
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 34

Thr Asp Asp Ser Arg Gly Trp Gly Leu Asn Ile
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 35

Thr Asp Asp Ser Arg Gly Trp Gly Leu Asn Ile
1               5                   10

<210> SEQ ID NO 36
<211> LENGTH: 11
<212> TYPE: PRT
<213> ORGANISM: Artificial Sequence
<220> FEATURE:
```

<223> OTHER INFORMATION: CDR stemming from rabbit antibody

<400> SEQUENCE: 36

Ser Gly Asp Thr Thr Ala Trp Gly Ala Asp Ile
1               5                   10

<210> SEQ ID NO 37
<211> LENGTH: 19
<212> TYPE: PRT
<213> ORGANISM: Artificial Sequence
<220> FEATURE:
<223> OTHER INFORMATION: CDR stemming from rabbit antibody

<400> SEQUENCE: 37

Gly Asp Asp Ser Ser Gly Tyr Thr Asp Gly Gly Tyr Ala Tyr Trp Gly
1               5                   10                  15

Leu Asp Ile

<210> SEQ ID NO 38
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 38

Gln Ala Ser Gln Ser Ile Ser Ser Tyr Leu Ser
1               5                   10

<210> SEQ ID NO 39
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 39

Gln Ala Ser Gln Ser Ile Gly Ser Ser Leu Ala
1               5                   10

<210> SEQ ID NO 40
<211> LENGTH: 13
<212> TYPE: PRT
<213> ORGANISM: Artificial Sequence
<220> FEATURE:
<223> OTHER INFORMATION: CDR stemming from rabbit antibody

<400> SEQUENCE: 40

Gln Ser Ser Gln Ser Val Trp Asn Asn Asn Arg Leu Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 41

Gln Ala Ser Glu Asn Ile Asn Ile Trp Leu Ser
1               5                   10

<210> SEQ ID NO 42
<211> LENGTH: 11
<212> TYPE: PRT
<213> ORGANISM: Artificial Sequence

```
<220> FEATURE:
<223> OTHER INFORMATION: CDR stemming from rabbit antibody

<400> SEQUENCE: 42

Gln Ala Ser Gln Ser Ile Ser Ser Trp Leu Ser
1               5                   10

<210> SEQ ID NO 43
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 43

Gln Ala Ser Glu Ile Ile His Ser Trp Leu Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 44

Gln Ala Ser Gln Ser Ile Asn Ile Trp Leu Ser
1               5                   10

<210> SEQ ID NO 45
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 45

Gln Ala Asp Gln Ser Ile Tyr Ile Trp Leu Ser
1               5                   10

<210> SEQ ID NO 46
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 46

Gln Ala Ser Gln Asn Ile Arg Ile Trp Leu Ser
1               5                   10

<210> SEQ ID NO 47
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 47

Gln Ala Ser Gln Ser Ile Asn Ile Trp Cys Ser
1               5                   10

<210> SEQ ID NO 48
<211> LENGTH: 11
<212> TYPE: PRT
<213> ORGANISM: Artificial Sequence
<220> FEATURE:
```

```
<223> OTHER INFORMATION: CDR stemming from rabbit antibody

<400> SEQUENCE: 48

Gln Ala Ser Gln Ser Ile Asn Ile Trp Leu Ser
1               5                   10

<210> SEQ ID NO 49
<211> LENGTH: 13
<212> TYPE: PRT
<213> ORGANISM: Artificial Sequence
<220> FEATURE:
<223> OTHER INFORMATION: CDR stemming from rabbit antibody

<400> SEQUENCE: 49

Gln Ala Ser Gln Ser Ile Asn Ile Asn Asn Trp Leu Ser
1               5                   10

<210> SEQ ID NO 50
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 50

Lys Ala Ser Thr Leu Ala Ser
1               5

<210> SEQ ID NO 51
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 51

Thr Ala Ala Asn Leu Ala Ser
1               5

<210> SEQ ID NO 52
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 52

Tyr Ala Ser Thr Leu Ala Ser
1               5

<210> SEQ ID NO 53
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 53

Gln Ala Ser Lys Leu Ala Ser
1               5

<210> SEQ ID NO 54
<211> LENGTH: 7
<212> TYPE: PRT
<213> ORGANISM: Artificial Sequence
<220> FEATURE:
<223> OTHER INFORMATION: CDR stemming from rabbit antibody
```

```
<400> SEQUENCE: 54

Gln Ala Ser Thr Leu Ala Ser
1               5

<210> SEQ ID NO 55
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 55

Leu Ala Ser Thr Leu Ala Ser
1               5

<210> SEQ ID NO 56
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 56

Lys Glu Ser Thr Leu Ala Ser
1               5

<210> SEQ ID NO 57
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 57

Lys Ala Ser Thr Leu Glu Ser
1               5

<210> SEQ ID NO 58
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 58

Lys Ala Ser Thr Leu Glu Ser
1               5

<210> SEQ ID NO 59
<211> LENGTH: 7
<212> TYPE: PRT
<213> ORGANISM: Artificial Sequence
<220> FEATURE:
<223> OTHER INFORMATION: CDR stemming from rabbit antibody

<400> SEQUENCE: 59

Arg Ala Ser Thr Leu Ala Ser
1               5

<210> SEQ ID NO 60
<211> LENGTH: 7
<212> TYPE: PRT
<213> ORGANISM: Artificial Sequence
<220> FEATURE:
<223> OTHER INFORMATION: CDR stemming from rabbit antibody
```

```
<400> SEQUENCE: 60

Lys Ala Ser Thr Leu Ala Ser
1               5

<210> SEQ ID NO 61
<211> LENGTH: 14
<212> TYPE: PRT
<213> ORGANISM: Artificial Sequence
<220> FEATURE:
<223> OTHER INFORMATION: CDR stemming from rabbit antibody

<400> SEQUENCE: 61

Gln Ser Asn Tyr Gly Gly Ser Ser Ser Asp Tyr Gly Asn Pro
1               5                   10

<210> SEQ ID NO 62
<211> LENGTH: 10
<212> TYPE: PRT
<213> ORGANISM: Artificial Sequence
<220> FEATURE:
<223> OTHER INFORMATION: CDR stemming from rabbit antibody

<400> SEQUENCE: 62

Gln Asn Phe Ala Thr Ser Asp Thr Val Thr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: CDR stemming from rabbit antibody

<400> SEQUENCE: 63

Ala Gly Gly Tyr Ser Ser Thr Ser Asp Asn Thr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: CDR stemming from rabbit antibody

<400> SEQUENCE: 64

Gln Asn Asn Tyr Ser Tyr Asn Arg Tyr Gly Ala Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: CDR stemming from rabbit antibody

<400> SEQUENCE: 65

Gln Asn Asn Tyr Gly Phe Arg Ser Tyr Gly Gly Ala
1               5                   10

<210> SEQ ID NO 66
<211> LENGTH: 12
<212> TYPE: PRT
<213> ORGANISM: Artificial Sequence
<220> FEATURE:
<223> OTHER INFORMATION: CDR stemming from rabbit antibody

<400> SEQUENCE: 66
```

```
Gln Asn Val Tyr Leu Ala Ser Thr Asn Gly Ala Asn
1               5                   10

<210> SEQ ID NO 67
<211> LENGTH: 12
<212> TYPE: PRT
<213> ORGANISM: Artificial Sequence
<220> FEATURE:
<223> OTHER INFORMATION: CDR stemming from rabbit antibody

<400> SEQUENCE: 67

Gln Asn Asn Tyr Asp Ser Gly Asn Asn Gly Phe Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: CDR stemming from rabbit antibody

<400> SEQUENCE: 68

Gln Asn Asn Ala His Tyr Ser Thr Asn Gly Gly Thr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: CDR stemming from rabbit antibody

<400> SEQUENCE: 69

Gln Asn Asn Ala His Tyr Ser Thr Asn Gly Gly Thr
1               5                   10

<210> SEQ ID NO 70
<211> LENGTH: 13
<212> TYPE: PRT
<213> ORGANISM: Artificial Sequence
<220> FEATURE:
<223> OTHER INFORMATION: CDR stemming from rabbit antibody

<400> SEQUENCE: 70

Gln Ala Asn Tyr Ala Tyr Ser Ala Gly Tyr Gly Ala Ala
1               5                   10

<210> SEQ ID NO 71
<211> LENGTH: 14
<212> TYPE: PRT
<213> ORGANISM: Artificial Sequence
<220> FEATURE:
<223> OTHER INFORMATION: CDR stemming from rabbit antibody

<400> SEQUENCE: 71

Gln Asn Asn Tyr His Tyr Ser Ser Ser Thr Asn Gly Gly Thr
1               5                   10

<210> SEQ ID NO 72
<211> LENGTH: 112
<212> TYPE: PRT
<213> ORGANISM: Artificial Sequence
<220> FEATURE:
<223> OTHER INFORMATION: recombinant scFv - VL sequence

<400> SEQUENCE: 72
```

```
Glu Val Val Met Ala Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
                20                  25                  30

Leu Ser Trp Tyr Gln Gln Lys Pro Gly Gln Pro Pro Lys Leu Leu Ile
                35                  40                  45

Tyr Lys Ala Ser Thr Leu Ala Ser Gly Val Pro Ser Arg Phe Lys Gly
    50                  55                  60

Ser Arg Ser Gly Thr Glu Tyr Thr Leu Thr Ile Ser Asp Leu Glu Cys
65                  70                  75                  80

Ala Asp Ala Ala Thr Tyr Tyr Cys Gln Ser Asn Tyr Gly Gly Ser Ser
                85                  90                  95

Ser Asp Tyr Gly Asn Pro Phe Gly Gly Gly Thr Glu Ala Val Val Lys
                100                 105                 110
```

<210> SEQ ID NO 73
<211> LENGTH: 108
<212> TYPE: PRT
<213> ORGANISM: Artificial Sequence
<220> FEATURE:
<223> OTHER INFORMATION: recombinant scFv - VL sequence

<400> SEQUENCE: 73

```
Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Ser Ile Gly Ser Ser
                20                  25                  30

Leu Ala Trp Tyr Gln Gln Lys Pro Gly Gln Arg Pro Lys Leu Leu Ile
                35                  40                  45

Tyr Thr Ala Ala Asn Leu Ala Ser Gly Val Pro Ser Arg Phe Arg Gly
    50                  55                  60

Ser Arg Ser Gly Ala Ala Phe Thr Leu Thr Ile Ser Asp Leu Glu Cys
65                  70                  75                  80

Ala Asp Ala Ala Thr Tyr Tyr Cys Gln Asn Phe Ala Thr Ser Asp Thr
                85                  90                  95

Val Thr Phe Gly Gly Gly Thr Glu Val Val Val Thr
                100                 105
```

<210> SEQ ID NO 74
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 74

```
Ala Val Val Leu Thr Gln Thr Pro Ser Pro Val Ser Ala Ala Val Gly
1               5                   10                  15

Gly Thr Val Ser Ile Ser Cys Gln Ser Ser Gln Ser Val Trp Asn Asn
                20                  25                  30

Asn Arg Leu Ala Trp Phe Gln Gln Lys Ser Gly Gln Pro Pro Lys Leu
                35                  40                  45

Leu Ile Tyr Tyr Ala Ser Thr Leu Ala Ser Gly Val Pro Ser Arg Phe
    50                  55                  60

Lys Gly Ser Gly Ser Gly Thr Glu Phe Thr Leu Thr Ile Ser Asp Val
65                  70                  75                  80

Gln Cys Asp Asp Ala Ala Thr Tyr Tyr Cys Ala Gly Gly Tyr Ser Ser
                85                  90                  95
```

```
Thr Ser Asp Asn Thr Phe Gly Gly Gly Thr Glu Val Val Lys
            100                 105                 110
```

<210> SEQ ID NO 75
<211> LENGTH: 110
<212> TYPE: PRT
<213> ORGANISM: Artificial Sequence
<220> FEATURE:
<223> OTHER INFORMATION: recombinant scFv - VL sequence

<400> SEQUENCE: 75

```
Asp Ile Val Met Thr Gln Thr Pro Ala Ser Val Glu Ala Thr Val Gly
1               5                   10                  15

Gly Thr Ile Thr Ile Asn Cys Gln Ala Ser Glu Asn Ile Asn Ile Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Asn Asn Tyr Ser Tyr Asn Arg
                85                  90                  95

Tyr Gly Ala Pro Phe Gly Gly Thr Glu Val Val Lys
            100                 105                 110
```

<210> SEQ ID NO 76
<211> LENGTH: 110
<212> TYPE: PRT
<213> ORGANISM: Artificial Sequence
<220> FEATURE:
<223> OTHER INFORMATION: recombinant scFv - VL sequence

<400> SEQUENCE: 76

```
Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Trp
            20                  25                  30

Leu Ser Trp Tyr Gln Gln Lys Pro Gly Gln Pro Pro Lys Leu Leu Ile
        35                  40                  45

Tyr Gln Ala Ser Thr Leu Ala Ser Gly Val Pro Pro Arg Ser Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Phe Cys Gln Asn Asn Tyr Gly Phe Arg Ser
                85                  90                  95

Tyr Gly Gly Ala Phe Gly Gly Gly Thr Glu Val Val Val Lys
            100                 105                 110
```

<210> SEQ ID NO 77
<211> LENGTH: 110
<212> TYPE: PRT
<213> ORGANISM: Artificial Sequence
<220> FEATURE:
<223> OTHER INFORMATION: recombinant scFv - VL sequence

<400> SEQUENCE: 77

```
Asp Val Val Met Thr Gln Thr Pro Ser Ser Val Ser Ala Ala Val Gly
1               5                   10                  15
```

Asp Thr Val Thr Ile Asn Cys Gln Ala Ser Glu Ile Ile His Ser Trp
            20                  25                  30

Leu Ala Trp Tyr Gln Gln Lys Pro Gly Gln Pro Lys Leu Leu Ile
        35                  40                  45

Tyr Leu Ala Ser Thr Leu Ala Ser Gly Val Pro Ser Arg Phe Lys Gly
50                  55                  60

Ser Gly Ser Gly Thr Gln Phe Thr Leu Thr Ile Ser Asp Leu Glu Cys
65                  70                  75                  80

Ala Asp Ala Ala Ile Tyr Tyr Cys Gln Asn Val Tyr Leu Ala Ser Thr
                85                  90                  95

Asn Gly Ala Asn Phe Gly Gly Gly Thr Glu Val Val Val Lys
            100                 105                 110

<210> SEQ ID NO 78
<211> LENGTH: 110
<212> TYPE: PRT
<213> ORGANISM: Artificial Sequence
<220> FEATURE:
<223> OTHER INFORMATION: recombinant scFv - VL sequence

<400> SEQUENCE: 78

Asp Val Val Met Thr Gln Thr Pro Ser Ser Val Ser Ala Ala Val Gly
1               5                   10                  15

Asp Thr Val Thr Ile Lys Cys Gln Ala Ser Gln Ser Ile Asn Ile Trp
            20                  25                  30

Leu Ser Trp Tyr Gln Gln Lys Ser Gly Gln Pro Pro Lys Leu Leu Val
        35                  40                  45

Tyr Lys Glu Ser Thr Leu Ala Ser Gly Val Pro Ser Arg Phe Arg Gly
50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Asn Asn Tyr Asp Ser Gly Asn
                85                  90                  95

Asn Gly Phe Pro Phe Gly Gly Gly Thr Glu Val Val Val Lys
            100                 105                 110

<210> SEQ ID NO 79
<211> LENGTH: 110
<212> TYPE: PRT
<213> ORGANISM: Artificial Sequence
<220> FEATURE:
<223> OTHER INFORMATION: recombinant scFv - VL sequence

<400> SEQUENCE: 79

Asp Val Val Met Thr Gln Thr Pro Ser Ser Val Ser Ala Ala Val Gly
1               5                   10                  15

Asp Thr Val Thr Ile Asn Cys Gln Ala Asp Gln Ser Ile Tyr Ile Trp
            20                  25                  30

Leu Ser Trp Tyr Gln Gln Lys Pro Gly Gln Pro Pro Lys Leu Leu Ile
        35                  40                  45

Tyr Lys Ala Ser Thr Leu Glu Ser Gly Val Pro Ser Arg Phe Lys Gly
50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Asn Asn Ala His Tyr Ser Thr
                85                  90                  95

Asn Gly Gly Thr Phe Gly Gly Gly Thr Glu Val Val Val Lys
            100                 105                 110

<210> SEQ ID NO 80
<211> LENGTH: 110
<212> TYPE: PRT
<213> ORGANISM: Artificial Sequence
<220> FEATURE:
<223> OTHER INFORMATION: recombinant scFv - VL sequence

<400> SEQUENCE: 80

Asp Val Val Met Thr Gln Thr Pro Ser Ser Val Ser Ala Ala Val Gly
1               5                   10                  15

Asp Thr Val Thr Ile Lys Cys Gln Ala Ser Gln Asn Ile Arg Ile Trp
            20                  25                  30

Leu Ser Trp Tyr Gln Gln Lys Pro Gly Gln Pro Pro Lys Leu Leu Ile
        35                  40                  45

Tyr Lys Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Asn Ala His Tyr Ser Thr
                85                  90                  95

Asn Gly Gly Thr Phe Gly Gly Gly Thr Glu Val Val Val Lys
            100                 105                 110

<210> SEQ ID NO 81
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 81

Glu Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Asn Ile Trp
            20                  25                  30

Cys Ser Trp Tyr Gln Gln Lys Pro Gly His Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ala Asn Tyr Ala Tyr Ser Ala
                85                  90                  95

Gly Tyr Gly Ala Ala Phe Gly Gly Gly Thr Glu Val Val Val Lys
            100                 105                 110

<210> SEQ ID NO 82
<211> LENGTH: 113
<212> TYPE: PRT
<213> ORGANISM: Artificial Sequence
<220> FEATURE:
<223> OTHER INFORMATION: recombinant scFv - VL sequence

<400> SEQUENCE: 82

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Ser Tyr
            20                  25                  30

```
Leu Ser Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Ser Asn Tyr Gly Gly Ser Ser
                 85                  90                  95

Ser Asp Tyr Gly Asn Pro Phe Gly Gln Gly Thr Lys Leu Thr Val Leu
            100                 105                 110

Gly

<210> SEQ ID NO 83
<211> LENGTH: 109
<212> TYPE: PRT
<213> ORGANISM: Artificial Sequence
<220> FEATURE:
<223> OTHER INFORMATION: recombinant scFv - VL sequence

<400> SEQUENCE: 83

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Gly Ser Ser
                 20                  25                  30

Leu Ala Trp Tyr Gln Gln Lys Pro Gly Lys Ala Pro Lys Leu Leu Ile
        35                  40                  45

Tyr Thr Ala Ala Asn Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Phe Ala Thr Ser Asp Thr
                 85                  90                  95

Val Thr Phe Gly Gln Gly Thr Lys Leu Thr Val Leu Gly
            100                 105

<210> SEQ ID NO 84
<211> LENGTH: 112
<212> TYPE: PRT
<213> ORGANISM: Artificial Sequence
<220> FEATURE:
<223> OTHER INFORMATION: recombinant scFv - VL sequence

<400> SEQUENCE: 84

Glu Ile Val Met Thr Gln Ser Pro Ser Thr Leu Ser Ala Ser Val Gly
 1               5                  10                  15

Asp Arg Val Ile Ile Thr Cys Gln Ser Ser Gln Ser Val Trp Asn Asn
                 20                  25                  30

Asn Arg Leu Ala Trp Tyr Gln Gln Lys Pro Gly Lys Ala Pro Lys Leu
        35                  40                  45

Leu Ile Tyr Tyr Ala Ser Thr Leu Ala Ser Gly Val Pro Ser Arg Phe
 50                  55                  60

Ser Gly Ser Gly Ser Gly Ala Glu Phe Thr Leu Thr Ile Ser Ser Leu
 65                  70                  75                  80

Gln Pro Asp Asp Phe Ala Thr Tyr Tyr Cys Ala Gly Gly Tyr Ser Ser
                 85                  90                  95

Thr Ser Asp Asn Thr Phe Gly Gln Gly Thr Lys Leu Thr Val Leu Gly
            100                 105                 110
```

<210> SEQ ID NO 85
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 85

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asn Ile Asn Ile Trp
            20                  25                  30

Leu Ser Trp Tyr Gln Gln Lys Pro Gly Lys Ala Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Asn Tyr Ser Tyr Asn Arg
                85                  90                  95

Tyr Gly Ala Pro Phe Gly Gln Gly Thr Lys Leu Thr Val Leu Gly
            100                 105                 110

<210> SEQ ID NO 86
<211> LENGTH: 111
<212> TYPE: PRT
<213> ORGANISM: Artifical Sequence
<220> FEATURE:
<223> OTHER INFORMATION: recombinant scFv - VL sequence

<400> SEQUENCE: 86

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Ser Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Asn Tyr Gly Phe Arg Ser
                85                  90                  95

Tyr Gly Gly Ala Phe Gly Gln Gly Thr Lys Leu Thr Val Leu Gly
            100                 105                 110

<210> SEQ ID NO 87
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 87

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile

```
            35                  40                  45

Tyr Leu Ala Ser Thr Leu Ala Ser Gly Val Pro Ser Arg Phe Ser Gly
         50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Val Tyr Leu Ala Ser Thr
                 85                  90                  95

Asn Gly Ala Asn Phe Gly Gln Gly Thr Lys Leu Thr Val Leu Gly
            100                 105                 110

<210> SEQ ID NO 88
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 88

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asn Ile Trp
            20                  25                  30

Leu Ser Trp Tyr Gln Gln Lys Pro Gly Lys Ala Pro Lys Leu Leu Ile
         35                  40                  45

Tyr Lys Glu Ser Thr Leu Ala Ser Gly Val Pro Ser Arg Phe Ser Gly
     50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Asn Tyr Asp Ser Gly Asn
                 85                  90                  95

Asn Gly Phe Pro Phe Gly Gln Gly Thr Lys Leu Thr Val Leu Gly
            100                 105                 110

<210> SEQ ID NO 89
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 89

Glu Ile Val Met Thr Gln Ser Pro Ser Thr Leu Ser Ala Ser Val Gly
 1               5                  10                  15

Asp Arg Val Ile Ile Thr Cys Gln Ala Asp Gln Ser Ile Tyr Ile Trp
            20                  25                  30

Leu Ser Trp Tyr Gln Gln Lys Pro Gly Lys Ala Pro Lys Leu Leu Ile
         35                  40                  45

Tyr Lys Ala Ser Thr Leu Glu Ser Gly Val Pro Ser Arg Phe Ser Gly
     50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Asn Ala His Tyr Ser Thr
                 85                  90                  95

Asn Gly Gly Thr Phe Gly Gln Gly Thr Lys Leu Thr Val Leu Gly
            100                 105                 110

<210> SEQ ID NO 90
<211> LENGTH: 111
```

```
<212> TYPE: PRT
<213> ORGANISM: Artificial Sequence
<220> FEATURE:
<223> OTHER INFORMATION: recombinant scFv - VL sequence

<400> SEQUENCE: 90

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Asn Ile Arg Ile Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Asn Ala His Tyr Ser Thr
                85                  90                  95

Asn Gly Gly Thr Phe Gly Gln Gly Thr Lys Leu Thr Val Leu Gly
            100                 105                 110

<210> SEQ ID NO 91
<211> LENGTH: 112
<212> TYPE: PRT
<213> ORGANISM: Artificial Sequence
<220> FEATURE:
<223> OTHER INFORMATION: recombinant scFv - VL sequence

<400> SEQUENCE: 91

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
            20                  25                  30

Cys Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Ala Asn Tyr Ala Tyr Ser Ala
                85                  90                  95

Gly Tyr Gly Ala Ala Phe Gly Gln Gly Thr Lys Leu Thr Val Leu Gly
            100                 105                 110

<210> SEQ ID NO 92
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 92

Glu Ile Val Leu Thr Gln Ser Pro Ser Ser Leu Ser Ala Ser Val Gly
1               5                   10                  15

Asp Arg Val Thr Ile Thr Cys Gln Ala Ser Glu Ile Ile His Ser Trp
            20                  25                  30

Leu Ala Trp Tyr Gln Gln Arg Pro Gly Lys Ala Pro Lys Leu Leu Ile
        35                  40                  45

Ser Leu Ala Ser Thr Leu Ala Ser Gly Val Pro Ser Arg Phe Ser Gly
```

```
                    50                  55                  60
Ser Gly Ser Gly Thr Asp Phe Thr Phe Thr Ile Ser Ser Leu Gln Pro
 65                  70                  75                  80

Glu Asp Phe Ala Val Tyr Tyr Cys Gln Asn Val Tyr Leu Ala Ser Thr
                 85                  90                  95

Asn Gly Ala Asn Phe Gly Gln Gly Thr Lys Val Glu Ile Lys Arg
            100                 105                 110
```

<210> SEQ ID NO 93
<211> LENGTH: 113
<212> TYPE: PRT
<213> ORGANISM: Artificial Sequence
<220> FEATURE:
<223> OTHER INFORMATION: recombinant scFv - VL sequence

<400> SEQUENCE: 93

```
Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Ser Ser Tyr
                20                  25                  30

Leu Ser Trp Tyr Gln Gln Lys Pro Gly Lys Ala Pro Lys Leu Leu Ile
             35                  40                  45

Tyr Lys Ala Ser Thr Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Ser Asn Tyr Gly Gly Ser Ser
                 85                  90                  95

Ser Asp Tyr Gly Asn Pro Phe Gly Gln Gly Thr Lys Leu Thr Val Leu
            100                 105                 110

Gly
```

<210> SEQ ID NO 94
<211> LENGTH: 109
<212> TYPE: PRT
<213> ORGANISM: Artificial Sequence
<220> FEATURE:
<223> OTHER INFORMATION: recombinant scFv - VL sequence

<400> SEQUENCE: 94

```
Glu Ile Val Met Thr Gln Ser Pro Ser Thr Leu Ser Ala Ser Val Gly
 1               5                  10                  15

Asp Arg Val Ile Ile Lys Cys Gln Ala Ser Gln Ser Ile Gly Ser Ser
                20                  25                  30

Leu Ala Trp Tyr Gln Gln Lys Pro Gly Lys Ala Pro Lys Leu Leu Ile
             35                  40                  45

Tyr Thr Ala Ala Asn Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Phe Ala Thr Ser Asp Thr
                 85                  90                  95

Val Thr Phe Gly Gln Gly Thr Lys Leu Thr Val Leu Gly
            100                 105
```

<210> SEQ ID NO 95
<211> LENGTH: 112
<212> TYPE: PRT

<213> ORGANISM: Artificial Sequence
<220> FEATURE:
<223> OTHER INFORMATION: recombinant scFv - VL sequence

<400> SEQUENCE: 95

```
Glu Ile Val Met Thr Gln Ser Pro Ser Thr Leu Ser Ala Ser Val Gly
1               5                   10                  15
Asp Arg Val Ile Ile Thr Cys Gln Ser Ser Gln Ser Val Trp Asn Asn
            20                  25                  30
Asn Arg Leu Ala Trp Tyr Gln Gln Lys Pro Gly Lys Ala Pro Lys Leu
        35                  40                  45
Leu Ile Tyr Tyr Ala Ser Thr Leu Ala Ser Gly Val Pro Ser Arg Phe
50                  55                  60
Ser Gly Ser Gly Ser Gly Thr Glu Phe Thr Leu Thr Ile Ser Ser Leu
65                  70                  75                  80
Gln Pro Asp Asp Phe Ala Thr Tyr Tyr Cys Ala Gly Gly Tyr Ser Ser
                85                  90                  95
Thr Ser Asp Asn Thr Phe Gly Gly Gly Thr Lys Leu Thr Val Leu Gly
            100                 105                 110
```

<210> SEQ ID NO 96
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 96

```
Glu Ile Val Met Thr Gln Ser Pro Ser Thr Leu Ser Ala Ser Val Gly
1               5                   10                  15
Asp Arg Val Ile Ile Thr Cys Gln Ala Ser Glu Asn Ile Asn Ile Trp
            20                  25                  30
Leu Ser Trp Tyr Gln Gln Lys Pro Gly Lys Ala Pro Lys Leu Leu Ile
        35                  40                  45
Tyr Gln Ala Ser Lys Leu Ala Ser Gly Val Pro Ser Arg Phe Ser Gly
50                  55                  60
Ser Gly Ser Gly Thr Gln Phe Thr Leu Thr Ile Ser Ser Leu Gln Pro
65                  70                  75                  80
Asp Asp Phe Ala Thr Tyr Tyr Cys Gln Asn Asn Tyr Ser Tyr Asn Arg
            85                  90                  95
Tyr Gly Ala Pro Phe Gly Gln Gly Thr Lys Leu Thr Val Leu Gly
            100                 105                 110
```

<210> SEQ ID NO 97
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 97

```
Glu Ile Val Met Thr Gln Ser Pro Ser Thr Leu Ser Ala Ser Val Gly
1               5                   10                  15
Asp Arg Val Ile Ile Thr Cys Gln Ala Ser Gln Ser Ile Ser Ser Trp
            20                  25                  30
Leu Ser Trp Tyr Gln Gln Lys Pro Gly Lys Ala Pro Lys Leu Leu Ile
        35                  40                  45
Tyr Gln Ala Ser Thr Leu Ala Ser Gly Val Pro Ser Arg Phe Ser Gly
50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Asn Tyr Gly Phe Arg Ser
                85                  90                  95

Tyr Gly Gly Ala Phe Gly Gln Gly Thr Lys Leu Thr Val Leu Gly
            100                 105                 110

<210> SEQ ID NO 98
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 98

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110

<210> SEQ ID NO 99
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 99

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
            20                  25                  30

Leu Ser Trp Tyr Gln Gln Lys Pro Gly Lys Ala Pro Lys Leu Leu Ile
        35                  40                  45

Tyr Lys Glu Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Asn Tyr Asp Ser Gly Asn
                85                  90                  95

Asn Gly Phe Pro Phe Gly Gln Gly Thr Lys Leu Thr Val Leu Gly
            100                 105                 110

<210> SEQ ID NO 100
<211> LENGTH: 111
<212> TYPE: PRT
<213> ORGANISM: Artificial Sequence
<220> FEATURE:
<223> OTHER INFORMATION: recombinant scFv - VL sequence -continued

<400> SEQUENCE: 100

Glu Ile Val Met Thr Gln Ser Pro Ser Thr Leu Ser Ala Ser Val Gly
1               5                   10                  15

Asp Arg Val Ile Ile Thr Cys Gln Ala Asp Gln Ser Ile Tyr Ile Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Asn Asn Ala His Tyr Ser Thr
                85                  90                  95

Asn Gly Gly Thr Phe Gly Gln Gly Thr Lys Leu Thr Val Leu Gly
            100                 105                 110

<210> SEQ ID NO 101
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 101

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Asn Ile Arg Ile Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Asn Ala His Tyr Ser Thr
                85                  90                  95

Asn Gly Gly Thr Phe Gly Gln Gly Thr Lys Leu Thr Val Leu Gly
            100                 105                 110

<210> SEQ ID NO 102
<211> LENGTH: 112
<212> TYPE: PRT
<213> ORGANISM: Artificial Sequence
<220> FEATURE:
<223> OTHER INFORMATION: recombinant scFv - VL sequence

<400> SEQUENCE: 102

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

-continued

```
Asp Asp Phe Ala Thr Tyr Tyr Cys Gln Ala Asn Tyr Ala Tyr Ser Ala
                85                  90                  95

Gly Tyr Gly Ala Ala Phe Gly Gln Gly Thr Lys Leu Thr Val Leu Gly
            100                 105                 110

<210> SEQ ID NO 103
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 103

Glu Ile Val Met Thr Gln Ser Pro Ser Ser Leu Ser Ala Ser Val Gly
1               5                   10                  15

Asp Arg Val Thr Ile Thr Cys Gln Ala Ser Glu Ile Ile His Ser Trp
            20                  25                  30

Leu Ala Trp Tyr Gln Gln Arg Pro Gly Lys Ala Pro Lys Leu Leu Ile
        35                  40                  45

Ser Leu Ala Ser Thr Leu Ala Ser Gly Val Pro Ser Arg Phe Ser Gly
    50                  55                  60

Ser Gly Ser Gly Thr Gln Phe Thr Phe Thr Ile Ser Ser Leu Gln Pro
65                  70                  75                  80

Glu Asp Phe Ala Val Tyr Tyr Cys Gln Asn Val Tyr Leu Ala Ser Thr
                85                  90                  95

Asn Gly Ala Asn Phe Gly Gln Gly Thr Lys Val Glu Ile Lys Arg
            100                 105                 110

<210> SEQ ID NO 104
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 104

Asp Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110

<210> SEQ ID NO 105
<211> LENGTH: 111
<212> TYPE: PRT
<213> ORGANISM: Artificial Sequence
<220> FEATURE:
<223> OTHER INFORMATION: recombinant scFv - VL sequence

<400> SEQUENCE: 105
```

-continued

Glu Val Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
            35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110

<210> SEQ ID NO 106
<211> LENGTH: 112
<212> TYPE: PRT
<213> ORGANISM: Artificial Sequence
<220> FEATURE:
<223> OTHER INFORMATION: recombinant scFv - VL sequence

<400> SEQUENCE: 106

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
            20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Ala Asn Tyr Ala Tyr Ser Ala
                85                  90                  95

Gly Tyr Gly Ala Ala Phe Gly Gly Gly Thr Lys Leu Thr Val Leu Gly
            100                 105                 110

<210> SEQ ID NO 107
<211> LENGTH: 128
<212> TYPE: PRT
<213> ORGANISM: Artificial Sequence
<220> FEATURE:
<223> OTHER INFORMATION: recombinant scFv - VH sequence

<400> SEQUENCE: 107

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Pro Phe Ser Ser Gly Tyr
            20                  25                  30

Trp Val Cys Trp Val Arg Gln Ala Pro Gly Lys Gly Leu Glu Trp Ile
            35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Asn Asn Tyr Tyr Ile Tyr Thr Asp Gly Tyr Ala Tyr
            100                 105                 110

Ala Gly Leu Glu Leu Trp Gly Pro Gly Ile Leu Val Thr Val Ser Ser
        115                 120                 125

<210> SEQ ID NO 108
<211> LENGTH: 128
<212> TYPE: PRT
<213> ORGANISM: Artificial Sequence
<220> FEATURE:
<223> OTHER INFORMATION: recombinant scFv - VH sequence

<400> SEQUENCE: 108

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Trp Ile Cys Trp Val Arg Gln Ala Pro Gly Lys Gly Leu Glu Trp Ile
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Asn Asn Tyr Tyr Ile Tyr Thr Asp Gly Tyr Ala Tyr
            100                 105                 110

Ala Gly Leu Glu Leu Trp Gly Pro Gly Ile Leu Val Thr Val Ser Ser
        115                 120                 125

<210> SEQ ID NO 109
<211> LENGTH: 117
<212> TYPE: PRT
<213> ORGANISM: Artificial Sequence
<220> FEATURE:
<223> OTHER INFORMATION: recombinant scFv - VH sequence

<400> SEQUENCE: 109

Gln Ser Leu Glu Glu Ser Gly Gly Asp Leu Val Gln Pro Gly Ala Ser
1               5                   10                  15

Leu Thr Leu Thr Cys Lys Val Ser Gly Phe Ser Leu Asn Thr Asn Tyr
            20                  25                  30

Trp Met Cys Trp Val Arg Gln Ala Pro Gly Lys Gly Leu Glu Trp Ile
        35                  40                  45

Gly Cys Met Tyr Thr Gly Ser Tyr Asn Arg Ala Tyr Tyr Ala Ser Trp
    50                  55                  60

Ala Lys Gly Arg Phe Thr Ser Ser Lys Thr Ser Ser Thr Thr Val Thr
65                  70                  75                  80

Leu Glu Met Thr Ser Leu Thr Ala Ala Asp Thr Ala Thr Tyr Phe Cys
                85                  90                  95

Ala Lys Gly Ser Asn Trp Tyr Ser Asp Leu Trp Gly Pro Gly Thr Leu
            100                 105                 110

Val Thr Val Ser Ser
            115

<210> SEQ ID NO 110
<211> LENGTH: 124
<212> TYPE: PRT

<213> ORGANISM: Artificial Sequence
<220> FEATURE:
<223> OTHER INFORMATION: recombinant scFv - VH sequence

<400> SEQUENCE: 110

```
Gln Glu Arg Leu Val Glu Ser Gly Gly Leu Val Gln Pro Glu Gly
1               5                   10                  15

Ser Leu Thr Leu Thr Cys Lys Ala Ser Gly Phe Ser Phe Ser Arg Ser
            20                  25                  30

Tyr Tyr Ile Tyr Trp Val Arg Gln Ala Pro Gly Lys Gly Leu Glu Trp
        35                  40                  45

Ile Ala Cys Ile Asp Ala Gly Ser Ser Gly Ile Leu Val Tyr Ala Asn
50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
            85                  90                  95

Cys Ala Arg Gly Asp Ala Ser Tyr Gly Val Asp Ser Phe Met Leu Pro
            100                 105                 110

Leu Trp Gly Pro Gly Thr Leu Val Thr Val Ser Ser
        115                 120
```

<210> SEQ ID NO 111
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 111

```
Gln Ser Leu Glu Glu Ser Gly Gly Leu Val Gln Pro Glu Gly Ser
1               5                   10                  15

Leu Thr Leu Thr Cys Lys Ala Ser Gly Phe Ser Phe Thr Thr Thr Asp
            20                  25                  30

Tyr Met Cys Trp Val Arg Gln Ala Pro Gly Lys Gly Leu Glu Trp Ile
        35                  40                  45

Gly Cys Ile Leu Ala Gly Asp Gly Ser Thr Tyr Tyr Ala Asn Trp Ala
    50                  55                  60

Lys Gly Arg Phe Thr Gly Ser Lys Thr Ser Ser Thr Thr Val Asp Leu
65                  70                  75                  80

Lys Met Thr Gly Leu Thr Ala Ala Asp Thr Ala Thr Tyr Phe Cys Ala
            85                  90                  95

Arg Ser Asp Pro Ala Ser Ser Trp Ser Phe Ala Leu Trp Gly Pro Gly
            100                 105                 110

Thr Leu Val Thr Val Ser Ser
        115
```

<210> SEQ ID NO 112
<211> LENGTH: 117
<212> TYPE: PRT
<213> ORGANISM: Artificial Sequence
<220> FEATURE:
<223> OTHER INFORMATION: recombinant scFv - VH sequence

<400> SEQUENCE: 112

```
Gln Ser Leu Glu Glu Ser Gly Gly Arg Leu Val Thr Pro Gly Thr Pro
1               5                   10                  15

Leu Thr Leu Thr Cys Thr Ala Ser Gly Ile Asp Phe Ser Gly Ala Tyr
            20                  25                  30
```

```
Tyr Met Gly Trp Val Arg Gln Ala Pro Gly Lys Gly Leu Glu Trp Ile
            35                  40                  45

Gly Tyr Ile Asp Tyr Asp Gly Asp Arg Tyr Tyr Ala Ser Trp Ala Lys
50                  55                  60

Gly Arg Phe Thr Ile Ser Lys Thr Ser Thr Val Asp Leu Lys Ile
65                  70                  75                  80

Thr Ser Pro Thr Thr Glu Asp Thr Ala Thr Tyr Phe Cys Ala Arg Ser
                85                  90                  95

Asp Tyr Ser Ser Gly Trp Gly Thr Asp Ile Trp Gly Pro Gly Thr Leu
                100                 105                 110

Val Thr Val Ser Leu
            115

<210> SEQ ID NO 113
<211> LENGTH: 117
<212> TYPE: PRT
<213> ORGANISM: Artificial Sequence
<220> FEATURE:
<223> OTHER INFORMATION: recombinant scFv - VH sequence

<400> SEQUENCE: 113

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Thr Asp Tyr Tyr
            20                  25                  30

Tyr Met Thr Trp Val Arg Leu Ala Pro Gly Lys Gly Leu Glu Tyr Ile
            35                  40                  45

Gly Phe Ile Asp Pro Asp Asp Pro Tyr Tyr Ala Thr Trp Ala Lys
50                  55                  60

Gly Arg Phe Thr Ile Ser Arg Thr Ser Thr Val Asn Leu Lys Met
65                  70                  75                  80

Thr Ser Pro Thr Thr Glu Asp Thr Ala Thr Tyr Phe Cys Ala Gly Gly
                85                  90                  95

Asp His Asn Ser Gly Trp Gly Leu Asp Ile Trp Gly Pro Gly Thr Leu
                100                 105                 110

Val Thr Val Ser Leu
            115

<210> SEQ ID NO 114
<211> LENGTH: 116
<212> TYPE: PRT
<213> ORGANISM: Artificial Sequence
<220> FEATURE:
<223> OTHER INFORMATION: recombinant scFv - VH sequence

<400> SEQUENCE: 114

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Tyr Tyr Tyr
            20                  25                  30

Met Ser Trp Val Arg Gln Ala Pro Gly Lys Gly Leu Glu Trp Ile Gly
            35                  40                  45

Ile Ile Gly Pro Gly Asp Tyr Thr Asp Tyr Ala Ser Trp Ala Lys Gly
50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Gly Arg Gly Asp
```

```
                    85                  90                  95

Asp Asn Ser Gly Trp Gly Glu Asp Ile Trp Gly Pro Gly Thr Leu Val
              100                 105                 110

Thr Val Ser Leu
        115

<210> SEQ ID NO 115
<211> LENGTH: 116
<212> TYPE: PRT
<213> ORGANISM: Artificial Sequence
<220> FEATURE:
<223> OTHER INFORMATION: recombinant scFv - VH sequence

<400> SEQUENCE: 115

Gln Ser Val Glu Glu Ser Gly Gly Arg Leu Val Thr Pro Gly Ala Pro
1               5                   10                  15

Leu Thr Leu Thr Cys Ser Val Ser Gly Phe Ser Leu Ser Asp Tyr Tyr
            20                  25                  30

Met Cys Trp Val Arg Gln Ala Pro Gly Lys Gly Leu Gln Trp Ile Gly
        35                  40                  45

Cys Leu Asp Tyr Phe Gly Ser Thr Asp Asp Ala Ser Trp Ala Lys Gly
50                  55                  60

Arg Phe Thr Ile Ser Lys Thr Ser Thr Ala Val Asp Leu Lys Ile Thr
65                  70                  75                  80

Ser Pro Thr Thr Glu Asp Thr Ala Thr Tyr Phe Cys Ala Arg Thr Asp
                85                  90                  95

Asp Ser Arg Gly Trp Gly Leu Asn Ile Trp Gly Pro Gly Thr Leu Val
              100                 105                 110

Thr Val Ser Leu
        115

<210> SEQ ID NO 116
<211> LENGTH: 116
<212> TYPE: PRT
<213> ORGANISM: Artificial Sequence
<220> FEATURE:
<223> OTHER INFORMATION: recombinant scFv - VH sequence

<400> SEQUENCE: 116

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Cys Trp Val Arg Gln Ala Pro Gly Lys Gly Leu Glu Trp Ile Gly
        35                  40                  45

Cys Leu Asp Tyr Val Gly Asp Thr Asp Tyr Ala Ser Trp Ala Lys Gly
50                  55                  60

Arg Phe Thr Ile Ser Lys Ala Ser Thr Thr Val Asp Leu Lys Ile Thr
65                  70                  75                  80

Ser Leu Thr Thr Glu Asp Thr Ala Thr Tyr Phe Cys Ala Arg Thr Asp
                85                  90                  95

Asp Ser Arg Gly Trp Gly Leu Asn Ile Trp Gly Pro Gly Thr Leu Val
              100                 105                 110

Thr Val Ser Leu
        115

<210> SEQ ID NO 117
<211> LENGTH: 118
```

<212> TYPE: PRT
<213> ORGANISM: Artificial Sequence
<220> FEATURE:
<223> OTHER INFORMATION: recombinant scFv - VH sequence

<400> SEQUENCE: 117

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Thr Tyr Tyr
            20                  25                  30

Met Asn Trp Val Arg Gln Ala Pro Gly Lys Gly Leu Glu Trp Ile Gly
        35                  40                  45

Ile Ile Ala Pro Asp Asp Thr Thr Tyr Tyr Ala Ser Trp Ala Lys Ser
50                  55                  60

Arg Ser Thr Ile Thr Arg Asp Thr Asn Glu Asn Thr Val Thr Leu Lys
65                  70                  75                  80

Met Thr Ser Leu Thr Thr Glu Asp Thr Ala Thr Tyr Phe Cys Ala Arg
                85                  90                  95

Ser Gly Asp Thr Thr Ala Trp Gly Ala Asp Ile Trp Gly Pro Gly Thr
            100                 105                 110

Leu Val Thr Val Ser Leu
        115

<210> SEQ ID NO 118
<211> LENGTH: 130
<212> TYPE: PRT
<213> ORGANISM: Artificial Sequence
<220> FEATURE:
<223> OTHER INFORMATION: recombinant scFv - VH sequence

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Gly
            20                  25                  30

Tyr Trp Val Cys Trp Val Arg Gln Ala Pro Gly Lys Gly Leu Glu Trp
        35                  40                  45

Val Ser Cys Ile Tyr Ala Gly Ser Ser Gly Ser Thr Tyr Tyr Ala Ser
50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Asn Asn Tyr Tyr Ile Tyr Thr Asp Gly Gly Tyr
            100                 105                 110

Ala Tyr Ala Gly Leu Glu Leu Trp Gly Gln Gly Thr Leu Val Thr Val
        115                 120                 125

Ser Ser
    130

<210> SEQ ID NO 119
<211> LENGTH: 130
<212> TYPE: PRT
<213> ORGANISM: Artificial Sequence
<220> FEATURE:
<223> OTHER INFORMATION: recombinant scFv - VH sequence

<400> SEQUENCE: 119

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Ser Phe Ser Ser Gly
            20                  25                  30

Tyr Trp Ile Cys Trp Val Arg Gln Ala Pro Gly Lys Gly Leu Glu Trp
            35                  40                  45

Val Ser Cys Ile Tyr Ala Gly Ser Ser Gly Ser Thr Tyr Tyr Ala Ser
        50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Ala Lys Gly Asn Asn Tyr Tyr Ile Tyr Thr Asp Gly Gly Tyr
                100                 105                 110

Ala Tyr Ala Gly Leu Glu Leu Trp Gly Gln Gly Thr Leu Val Thr Val
            115                 120                 125

Ser Ser
    130
```

<210> SEQ ID NO 120
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Thr Asn
            20                  25                  30

Tyr Trp Met Cys Trp Val Arg Gln Ala Pro Gly Lys Gly Leu Glu Trp
            35                  40                  45

Val Ser Cys Met Tyr Thr Gly Ser Tyr Asn Arg Ala Tyr Tyr Ala Ser
        50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Ala Lys Gly Ser Asn Trp Tyr Ser Asp Leu Trp Gly Gln Gly
                100                 105                 110

Thr Leu Val Thr Val Ser Ser
            115
```

<210> SEQ ID NO 121
<211> LENGTH: 125
<212> TYPE: PRT
<213> ORGANISM: Artificial Sequence
<220> FEATURE:
<223> OTHER INFORMATION: recombinant scFv - VH sequence

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Arg Ser
            20                  25                  30

Tyr Tyr Ile Tyr Trp Val Arg Gln Ala Pro Gly Lys Gly Leu Glu Trp
            35                  40                  45
```

```
Val Ser Cys Ile Asp Ala Gly Ser Ser Gly Ile Leu Val Tyr Ala Asn
    50                  55                  60

Trp Ala Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Lys Gly Asp Ala Ser Tyr Gly Val Asp Ser Phe Met Leu
            100                 105                 110

Pro Leu Trp Gly Gln Gly Thr Leu Val Thr Val Ser Ser
        115                 120                 125

<210> SEQ ID NO 122
<211> LENGTH: 121
<212> TYPE: PRT
<213> ORGANISM: Artificial Sequence
<220> FEATURE:
<223> OTHER INFORMATION: recombinant scFv - VH sequence

<400> SEQUENCE: 122

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Thr Thr Thr
                20                  25                  30

Asp Tyr Met Cys Trp Val Arg Gln Ala Pro Gly Lys Gly Leu Glu Trp
            35                  40                  45

Val Ser Cys Ile Leu Ala Gly Asp Gly Ser Thr Tyr Tyr Ala Asn Trp
    50                  55                  60

Ala Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                85                  90                  95

Cys Ala Lys Ser Asp Pro Ala Ser Ser Trp Ser Phe Ala Leu Trp Gly
            100                 105                 110

Gln Gly Thr Leu Val Thr Val Ser Ser
        115                 120

<210> SEQ ID NO 123
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 123

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ile Asp Phe Ser Gly Ala
                20                  25                  30

Tyr Tyr Met Gly Trp Val Arg Gln Ala Pro Gly Lys Gly Leu Glu Trp
            35                  40                  45

Val Ser Tyr Ile Asp Tyr Asp Gly Asp Arg Tyr Tyr Ala Ser Trp Ala
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Asp Tyr Ser Ser Gly Trp Gly Thr Asp Ile Trp Gly Gln
            100                 105                 110
```

Gly Thr Leu Val Thr Val Ser Ser
        115             120

<210> SEQ ID NO 124
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Tyr Met Thr Trp Val Arg Gln Ala Pro Gly Lys Gly Leu Glu Trp
        35                  40                  45

Val Ser Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Asp His Asn Ser Gly Trp Gly Leu Asp Ile Trp Gly Gln
            100                 105                 110

Gly Thr Leu Val Thr Val Ser Ser
        115             120

<210> SEQ ID NO 125
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Tyr Tyr
            20                  25                  30

Tyr Met Ser Trp Val Arg Gln Ala Pro Gly Lys Gly Leu Glu Trp Val
        35                  40                  45

Ser Ile Ile Gly Pro Gly Asp Tyr Thr Asp Tyr Ala Ser Trp Ala Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Lys Gly Asp Asp Asn Ser Gly Trp Gly Glu Asp Ile Trp Gly Gln Gly
            100                 105                 110

Thr Leu Val Thr Val Ser Ser
        115

<210> SEQ ID NO 126
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asp Tyr
            20                  25                  30

Tyr Met Cys Trp Val Arg Gln Ala Pro Gly Lys Gly Leu Glu Trp Val
        35                  40                  45

Ser Cys Leu Asp Tyr Phe Gly Ser Thr Asp Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Asp Asp Ser Arg Gly Trp Gly Leu Asn Ile Trp Gly Gln Gly
            100                 105                 110

Thr Leu Val Thr Val Ser Ser
        115

<210> SEQ ID NO 127
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Tyr Met Cys Trp Val Arg Gln Ala Pro Gly Lys Gly Leu Glu Trp Val
        35                  40                  45

Ser Cys Leu Asp Tyr Val Gly Asp Thr Asp Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Asp Asp Ser Arg Gly Trp Gly Leu Asn Ile Trp Gly Gln Gly
            100                 105                 110

Thr Leu Val Thr Val Ser Ser
        115

<210> SEQ ID NO 128
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Thr Tyr
            20                  25                  30

Tyr Met Asn Trp Val Arg Gln Ala Pro Gly Lys Gly Leu Glu Trp Val
        35                  40                  45

Ser Ile Ile Ala Pro Asp Asp Thr Thr Tyr Tyr Ala Ser Trp Ala Lys
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Lys Ser Gly Asp Thr Thr Ala Trp Gly Ala Asp Ile Trp Gly Gln Gly
            100                 105                 110

Thr Leu Val Thr Val Ser Ser
            115

<210> SEQ ID NO 129
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 129

Gln Val Gln Leu Val Gln Thr Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Ser Phe Ile Asp Pro Asp Asp Pro Tyr Tyr Ala Thr Trp Ala
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Leu Tyr Tyr Cys
             85                  90                  95

Ala Lys Gly Asp His Asn Ser Gly Trp Gly Leu Asp Ile Trp Gly Gln
            100                 105                 110

Gly Thr Leu Val Thr Val Ser Ser
            115                 120

<210> SEQ ID NO 130
<211> LENGTH: 130
<212> TYPE: PRT
<213> ORGANISM: Artificial Sequence
<220> FEATURE:
<223> OTHER INFORMATION: recombinant scFv - VH sequence

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Pro Phe Ser Ser Gly
            20                  25                  30

Tyr Trp Val Cys Trp Val Arg Gln Ala Pro Gly Lys Gly Leu Glu Trp
        35                  40                  45

Val Gly Cys Ile Tyr Ala Gly Ser Ser Gly Ser Thr Tyr Tyr Ala Ser
 50                  55                  60

Trp Ala Lys Gly Arg Phe Thr Ile Ser Lys Asp Thr Ser Lys Asn Thr
 65                  70                  75                  80

Val Tyr Leu Gln Met Asn Ser Leu Arg Ala Glu Asp Thr Ala Val Tyr
             85                  90                  95

Tyr Cys Ala Arg Gly Asn Asn Tyr Tyr Ile Tyr Thr Asp Gly Gly Tyr

```
            100                 105                 110
Ala Tyr Ala Gly Leu Glu Leu Trp Gly Gln Gly Thr Leu Val Thr Val
        115                 120                 125

Ser Ser
    130

<210> SEQ ID NO 131
<211> LENGTH: 130
<212> TYPE: PRT
<213> ORGANISM: Artificial Sequence
<220> FEATURE:
<223> OTHER INFORMATION: recombinant scFv - VH sequence

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Phe Ser Ser Gly
            20                  25                  30

Tyr Trp Ile Cys Trp Val Arg Gln Ala Pro Gly Lys Gly Leu Glu Trp
        35                  40                  45

Val Gly Cys Ile Tyr Ala Gly Ser Ser Gly Ser Thr Tyr Tyr Ala Ser
50                  55                  60

Trp Ala Lys Gly Arg Phe Thr Ile Ser Lys Asp Thr Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Gly Asn Asn Tyr Tyr Ile Tyr Thr Asp Gly Gly Tyr
            100                 105                 110

Ala Tyr Ala Gly Leu Glu Leu Trp Gly Gln Gly Thr Leu Val Thr Val
        115                 120                 125

Ser Ser
    130

<210> SEQ ID NO 132
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Ser Leu Asn Thr Asn
            20                  25                  30

Tyr Trp Met Cys Trp Val Arg Gln Ala Pro Gly Lys Gly Leu Glu Trp
        35                  40                  45

Val Gly Cys Met Tyr Thr Gly Ser Tyr Asn Arg Ala Tyr Tyr Ala Ser
50                  55                  60

Trp Ala Lys Gly Arg Phe Thr Ser Ser Lys Asp Thr Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Lys Gly Ser Asn Trp Tyr Ser Asp Leu Trp Gly Gln Gly
            100                 105                 110

Thr Leu Val Thr Val Ser Ser
        115
```

```
<210> SEQ ID NO 133
<211> LENGTH: 125
<212> TYPE: PRT
<213> ORGANISM: Artificial Sequence
<220> FEATURE:
<223> OTHER INFORMATION: recombinant scFv - VH sequence

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Lys Ala Ser Gly Phe Ser Phe Ser Arg Ser
            20                  25                  30

Tyr Tyr Ile Tyr Trp Val Arg Gln Ala Pro Gly Lys Gly Leu Glu Trp
        35                  40                  45

Val Gly Cys Ile Asp Ala Gly Ser Ser Gly Ile Leu Val Tyr Ala Asn
    50                  55                  60

Trp Ala Lys Gly Arg Phe Thr Ile Ser Lys Asp Thr Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Gly Asp Ala Ser Tyr Gly Val Asp Ser Phe Met Leu
            100                 105                 110

Pro Leu Trp Gly Gln Gly Thr Leu Val Thr Val Ser Ser
        115                 120                 125

<210> SEQ ID NO 134
<211> LENGTH: 121
<212> TYPE: PRT
<213> ORGANISM: Artificial Sequence
<220> FEATURE:
<223> OTHER INFORMATION: recombinant scFv - VH sequence

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Lys Ala Ser Gly Phe Ser Phe Thr Thr Thr
            20                  25                  30

Asp Tyr Met Cys Trp Val Arg Gln Ala Pro Gly Lys Gly Leu Glu Trp
        35                  40                  45

Val Gly Cys Ile Leu Ala Gly Asp Gly Ser Thr Tyr Tyr Ala Asn Trp
    50                  55                  60

Ala Lys Gly Arg Phe Thr Gly Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Ser Asp Pro Ala Ser Ser Trp Ser Phe Ala Leu Trp Gly
            100                 105                 110

Gln Gly Thr Leu Val Thr Val Ser Ser
        115                 120

<210> SEQ ID NO 135
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 135

Glu Val Gln Leu Val Glu Ser Gly Gly Gly Leu Val Gln Pro Gly Gly
```

```
  1               5                  10                 15
Ser Leu Arg Leu Ser Cys Thr Ala Ser Gly Ile Asp Phe Ser Gly Ala
                20                 25                 30

Tyr Tyr Met Gly Trp Val Arg Gln Ala Pro Gly Lys Gly Leu Glu Trp
            35                 40                 45

Val Gly Tyr Ile Asp Tyr Asp Gly Arg Tyr Tyr Ala Ser Trp Ala
    50                 55                 60

Lys Gly Arg Phe Thr Ile Ser Lys Asp Thr Ser Lys Asn Thr Val Tyr
 65                 70                 75                 80

Leu Gln Met Asn Ser Leu Arg Ala Glu Asp Thr Ala Val Tyr Tyr Cys
                85                 90                 95

Ala Arg Ser Asp Tyr Ser Ser Gly Trp Gly Thr Asp Ile Trp Gly Gln
                   100                105                110

Gly Thr Leu Val Thr Val Ser Ser
            115                120
```

<210> SEQ ID NO 136
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 136

```
Glu Val Gln Leu Val Glu Ser Gly Gly Gly Leu Val Gln Pro Gly Gly
 1               5                  10                 15

Ser Leu Arg Leu Ser Cys Thr Ala Ser Gly Phe Ser Leu Thr Asp Tyr
                20                 25                 30

Tyr Tyr Met Thr Trp Val Arg Gln Ala Pro Gly Lys Gly Leu Glu Trp
            35                 40                 45

Val Gly Phe Ile Asp Pro Asp Asp Pro Tyr Tyr Ala Thr Trp Ala
    50                 55                 60

Lys Gly Arg Phe Thr Ile Ser Arg Asp Thr Ser Lys Asn Thr Val Tyr
 65                 70                 75                 80

Leu Gln Met Asn Ser Leu Arg Ala Glu Asp Thr Ala Val Tyr Tyr Cys
                85                 90                 95

Ala Gly Gly Asp His Asn Ser Gly Trp Gly Leu Asp Ile Trp Gly Gln
                   100                105                110

Gly Thr Leu Val Thr Val Ser Ser
            115                120
```

<210> SEQ ID NO 137
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 137

```
Glu Val Gln Leu Val Glu Ser Gly Gly Gly Leu Val Gln Pro Gly Gly
 1               5                  10                 15

Ser Leu Arg Leu Ser Cys Thr Ala Ser Gly Phe Ser Leu Ser Tyr Tyr
                20                 25                 30

Tyr Met Ser Trp Val Arg Gln Ala Pro Gly Lys Gly Leu Glu Trp Val
            35                 40                 45

Gly Ile Ile Gly Pro Gly Asp Tyr Thr Asp Tyr Ala Ser Trp Ala Lys
    50                 55                 60
```

```
Gly Arg Phe Thr Ile Ser Lys Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Gly Asp Asp Asn Ser Gly Trp Gly Glu Asp Ile Trp Gly Gln Gly
            100                 105                 110

Thr Leu Val Thr Val Ser Ser
            115

<210> SEQ ID NO 138
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 138

Glu Val Gln Leu Val Glu Ser Gly Gly Gly Leu Val Gln Pro Gly Gly
 1               5                  10                  15

Ser Leu Arg Leu Ser Cys Ser Val Ser Gly Phe Ser Leu Ser Asp Tyr
                20                  25                  30

Tyr Met Cys Trp Val Arg Gln Ala Pro Gly Lys Gly Leu Glu Trp Val
            35                  40                  45

Gly Cys Leu Asp Tyr Phe Gly Ser Thr Asp Asp Ala Ser Trp Ala Lys
        50                  55                  60

Gly Arg Phe Thr Ile Ser Lys Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Thr Asp Asp Ser Arg Gly Trp Gly Leu Asn Ile Trp Gly Gln Gly
            100                 105                 110

Thr Leu Val Thr Val Ser Ser
            115

<210> SEQ ID NO 139
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 139

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ser Leu Ser Ser Tyr
                20                  25                  30

Tyr Met Cys Trp Val Arg Gln Ala Pro Gly Lys Gly Leu Glu Trp Val
            35                  40                  45

Gly Cys Leu Asp Tyr Val Gly Asp Thr Asp Tyr Ala Ser Trp Ala Lys
        50                  55                  60

Gly Arg Phe Thr Ile Ser Lys Asp Ala Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Thr Asp Asp Ser Arg Gly Trp Gly Leu Asn Ile Trp Gly Gln Gly
            100                 105                 110

Thr Leu Val Thr Val Ser Ser
            115
```

<210> SEQ ID NO 140
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Tyr Met Ser Trp Val Arg Gln Ala Pro Gly Lys Gly Leu Glu Trp Val
        35                  40                  45

Gly Ile Leu Asp Tyr Val Gly Asp Thr Asp Tyr Ala Ser Trp Ala Lys
    50                  55                  60

Gly Arg Phe Thr Ile Ser Lys Asp Ala Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Asp Asp Ser Arg Gly Trp Gly Leu Asn Ile Trp Gly Gln Gly
            100                 105                 110

Thr Leu Val Thr Val Ser Ser
        115

<210> SEQ ID NO 141
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Asn Thr Tyr
            20                  25                  30

Tyr Met Asn Trp Val Arg Gln Ala Pro Gly Lys Gly Leu Glu Trp Val
        35                  40                  45

Gly Ile Ile Ala Pro Asp Asp Thr Thr Tyr Tyr Ala Ser Trp Ala Lys
    50                  55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ser Gly Asp Thr Thr Ala Trp Gly Ala Asp Ile Trp Gly Gln Gly
            100                 105                 110

Thr Leu Val Thr Val Ser Ser
        115

<210> SEQ ID NO 142
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 142

Gln Val Gln Leu Val Gln Thr Gly Gly Gly Leu Val Gln Pro Gly Gly
1               5                   10                  15

Ser Leu Arg Leu Ser Cys Thr Ala Ser Gly Phe Ser Leu Thr Asp Tyr
                20                  25                  30

Tyr Tyr Met Thr Trp Val Arg Gln Ala Pro Gly Lys Gly Leu Glu Trp
            35                  40                  45

Val Gly Phe Ile Asp Pro Asp Asp Pro Tyr Tyr Ala Thr Trp Ala
50                      55                  60

Lys Gly Arg Phe Thr Ile Ser Arg Asp Thr Ser Lys Asn Thr Val Tyr
65                      70                  75                  80

Leu Gln Met Asn Ser Leu Arg Ala Glu Asp Thr Ala Leu Tyr Tyr Cys
                85                  90                  95

Ala Gly Gly Asp His Asn Ser Gly Trp Gly Leu Asp Ile Trp Gly Gln
                100                 105                 110

Gly Thr Leu Val Thr Val Ser Ser
        115                 120

<210> SEQ ID NO 143
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 143

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Ser Leu Ser Asp Tyr
                20                  25                  30

Tyr Met Cys Trp Val Arg Gln Ala Pro Gly Lys Gly Leu Glu Trp Val
            35                  40                  45

Ser Cys Leu Asp Tyr Phe Gly Ser Thr Asp Asp Ala Ser Trp Ala Lys
50                      55                  60

Gly Arg Phe Thr Ile Ser Arg Asp Asn Ser Lys Asn Thr Leu Tyr Leu
65                      70                  75                  80

Gln Met Asn Ser Leu Arg Ala Glu Asp Thr Ala Thr Tyr Tyr Cys Ala
                85                  90                  95

Lys Thr Asp Asp Ser Arg Gly Trp Gly Leu Asn Ile Trp Gly Gln Gly
                100                 105                 110

Thr Thr Val Thr Val Ser Ser
        115

<210> SEQ ID NO 144
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 144

Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Ser Leu Thr Asp Tyr
                20                  25                  30

Tyr Tyr Met Thr Trp Val Arg Gln Ala Pro Gly Lys Gly Leu Glu Trp
            35                  40                  45

Val Gly Phe Ile Asp Pro Asp Asp Pro Tyr Tyr Ala Thr Trp Ala
50                      55                  60

```
Lys Gly Arg Phe Thr Ile Ser Arg Asp Thr Ser Lys Asn Thr Val Tyr
 65                  70                  75                  80

Leu Gln Met Asn Ser Leu Arg Ala Glu Asp Thr Ala Thr Tyr Tyr Cys
                 85                  90                  95

Ala Gly Gly Asp His Asn Ser Gly Trp Gly Leu Asp Ile Trp Gly Gln
            100                 105                 110

Gly Thr Thr Val Thr Val Ser Ser
        115                 120

<210> SEQ ID NO 145
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 145

Glu Val Gln Leu Val Glu Ser Gly Gly Gly Ser Val Gln Pro Gly Gly
 1               5                  10                  15

Ser Leu Arg Leu Ser Cys Thr Val Ser Gly Phe Ser Leu Asn Thr Tyr
                20                  25                  30

Tyr Met Asn Trp Val Arg Gln Ala Pro Gly Lys Gly Leu Glu Trp Val
             35                  40                  45

Gly Ile Ile Ala Pro Asp Thr Thr Tyr Tyr Ala Ser Trp Ala Lys
         50                  55                  60

Ser Arg Ser Thr Ile Ser Arg Asp Thr Ser Lys Asn Thr Val Tyr Leu
 65                  70                  75                  80

Gln Met Asn Ser Leu Arg Ala Glu Asp Thr Ala Thr Tyr Tyr Cys Ala
                 85                  90                  95

Arg Ser Gly Asp Thr Thr Ala Trp Gly Ala Asp Ile Trp Gly Gln Gly
            100                 105                 110

Thr Thr Val Thr Val Ser Ser
        115

<210> SEQ ID NO 146
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 146

Gln Val Gln Leu Val Gln Thr Gly Gly Gly Ser Val Gln Pro Gly Gly
 1               5                  10                  15

Ser Leu Arg Leu Ser Cys Thr Ala Ser Gly Phe Ser Leu Thr Asp Tyr
                20                  25                  30

Tyr Tyr Met Thr Trp Val Arg Gln Ala Pro Gly Lys Gly Leu Glu Trp
             35                  40                  45

Val Gly Phe Ile Asp Pro Asp Asp Pro Tyr Tyr Ala Thr Trp Ala
         50                  55                  60

Lys Gly Arg Phe Thr Ile Ser Arg Asp Thr Ser Lys Asn Thr Val Tyr
 65                  70                  75                  80

Leu Gln Met Asn Ser Leu Arg Ala Glu Asp Thr Ala Thr Tyr Tyr Cys
                 85                  90                  95

Ala Gly Gly Asp His Asn Ser Gly Trp Gly Leu Asp Ile Trp Gly Gln
            100                 105                 110

Gly Thr Thr Val Thr Val Ser Ser
```

<210> SEQ ID NO 147
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 147

```
Val Gln Leu Val Glu Ser Gly Gly Leu Val Gln Pro Gly Gly Ser
1               5                   10                  15

Leu Arg Leu Ser Cys Thr Ala Ser Gly Phe Ser Leu Thr Asp Tyr Tyr
            20                  25                  30

Tyr Met Thr Trp Val Arg Gln Ala Pro Gly Lys Gly Leu Glu Trp Val
        35                  40                  45

Gly Phe Ile Asp Pro Asp Asp Pro Tyr Tyr Ala Thr Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Gly Gly Asp His Asn Ser Gly Trp Gly Leu Asp Ile Trp Gly Gln Gly
            100                 105                 110

Thr Leu Val Thr Val Ser Ser
            115
```

<210> SEQ ID NO 148
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 148

```
Glu Gln Gln Leu Val Glu Ser Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
            115                 120
```

<210> SEQ ID NO 149
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Leu Ala Pro Gly Lys Gly Leu Glu Trp
            35                  40                  45

Val Gly Phe Ile Asp Pro Asp Asp Pro Tyr Tyr Ala Thr Trp Ala
        50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
                100                 105                 110

Gly Thr Leu Val Thr Val Ser Ser
            115                 120

<210> SEQ ID NO 150
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Tyr
            35                  40                  45

Val Gly Phe Ile Asp Pro Asp Asp Pro Tyr Tyr Ala Thr Trp Ala
        50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
                100                 105                 110

Gly Thr Leu Val Thr Val Ser Ser
            115                 120

<210> SEQ ID NO 151
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
            35                  40                  45

Ile Gly Phe Ile Asp Pro Asp Asp Pro Tyr Tyr Ala Thr Trp Ala

```
                50                  55                  60
Lys Gly Arg Phe Thr Ile Ser Arg Asp Thr Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Gly Gly Asp His Asn Ser Gly Trp Gly Leu Asp Ile Trp Gly Gln
                100                 105                 110

Gly Thr Leu Val Thr Val Ser Ser
            115                 120

<210> SEQ ID NO 152
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 152

Glu Val Gln Leu Val Glu Ser Gly Gly Gly Leu Val Gln Pro Gly Gly
  1               5                  10                  15

Ser Leu Arg Leu Ser Cys Thr Ala Ser Gly Phe Ser Leu Thr Asp Tyr
                 20                  25                  30

Tyr Tyr Met Thr Trp Val Arg Gln Ala Pro Gly Lys Gly Leu Glu Trp
             35                  40                  45

Val Gly Phe Ile Asp Pro Asp Asp Pro Tyr Tyr Ala Thr Trp Ala
         50                  55                  60

Lys Gly Arg Phe Thr Ile Ser Arg Ala Thr Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Gly Gly Asp His Asn Ser Gly Trp Gly Leu Asp Ile Trp Gly Gln
                100                 105                 110

Gly Thr Leu Val Thr Val Ser Ser
            115                 120

<210> SEQ ID NO 153
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 153

Glu Val Gln Leu Val Glu Ser Gly Gly Gly Leu Val Gln Pro Gly Gly
  1               5                  10                  15

Ser Leu Arg Leu Ser Cys Thr Ala Ser Gly Phe Ser Leu Thr Asp Tyr
                 20                  25                  30

Tyr Tyr Met Thr Trp Val Arg Gln Ala Pro Gly Lys Gly Leu Glu Trp
             35                  40                  45

Val Gly Phe Ile Asp Pro Asp Asp Pro Tyr Tyr Ala Thr Trp Ala
         50                  55                  60

Lys Gly Arg Phe Thr Ile Ser Arg Asp Thr Ser Lys Ala Thr Val Tyr
 65                  70                  75                  80

Leu Gln Met Asn Ser Leu Arg Ala Glu Asp Thr Ala Val Tyr Tyr Cys
                 85                  90                  95

Ala Gly Gly Asp His Asn Ser Gly Trp Gly Leu Asp Ile Trp Gly Gln
                100                 105                 110
```

-continued

```
Gly Thr Leu Val Thr Val Ser Ser
        115                 120

<210> SEQ ID NO 154
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Phe Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 155
<211> LENGTH: 119
<212> TYPE: PRT
<213> ORGANISM: Artificial Sequence
<220> FEATURE:
<223> OTHER INFORMATION: recombinant scFv - VH sequence

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Gly Gly Asp His Asn Ser Gly Trp Gly Leu Asp Ile Trp Gly Gln Gly
            100                 105                 110

Thr Leu Val Thr Val Ser Ser
        115

<210> SEQ ID NO 156
<211> LENGTH: 119
<212> TYPE: PRT
<213> ORGANISM: Artificial Sequence
<220> FEATURE:
<223> OTHER INFORMATION: recombinant scFv - VH sequence
```

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Thr Val Tyr Leu
65                  70                  75                  80

Gln Met Asn Ser Leu Arg Ala Glu Asp Thr Ala Val Tyr Tyr Cys Ala
                85                  90                  95

Gly Gly Asp His Asn Ser Gly Trp Gly Leu Asp Ile Trp Gly Gln Gly
            100                 105                 110

Thr Leu Val Thr Val Ser Ser
        115

<210> SEQ ID NO 157
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 158
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Gly Asp His Asn Ser Gly Trp Gly Leu Asp Ile Trp Gly Gln
             100                 105                 110

Gly Thr Leu Val Thr Val Ser Ser
             115                 120

<210> SEQ ID NO 159
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 159

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ser Leu Thr Asp Tyr
                 20                  25                  30

Tyr Tyr Met Thr Trp Val Arg Gln Ala Pro Gly Lys Gly Leu Glu Trp
             35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Gly Gly Asp His Asn Ser Gly Trp Gly Leu Asp Ile Trp Gly Gln
             100                 105                 110

Gly Thr Leu Val Thr Val Ser Ser
             115                 120

<210> SEQ ID NO 160
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 160

Glu Val Gln Leu Val Glu Ser Gly Gly Gly Ser Val Gln Pro Gly Gly
 1               5                  10                  15

Ser Leu Arg Leu Ser Cys Thr Ala Ser Gly Phe Ser Leu Thr Asp Tyr
                 20                  25                  30

Tyr Tyr Met Thr Trp Val Arg Gln Ala Pro Gly Lys Gly Leu Glu Trp
             35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Thr Tyr Tyr Cys
                 85                  90                  95

Ala Gly Gly Asp His Asn Ser Gly Trp Gly Leu Asp Ile Trp Gly Gln
             100                 105                 110

```
Gly Thr Thr Val Thr Val Ser Ser
        115                 120

<210> SEQ ID NO 161
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 161

Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Gly Gly Asp His Asn Ser Gly Trp Gly Leu Asp Ile Trp Gly Gln
            100                 105                 110

Gly Thr Thr Val Thr Val Ser Ser
        115                 120

<210> SEQ ID NO 162
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 162

Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Ala Tyr
65                  70                  75                  80

Leu Gln Met Asn Ser Leu Arg Ala Glu Asp Thr Ala Thr Tyr Tyr Cys
                85                  90                  95

Ala Gly Gly Asp His Asn Ser Gly Trp Gly Leu Asp Ile Trp Gly Gln
            100                 105                 110

Gly Thr Thr Val Thr Val Ser Ser
        115                 120

<210> SEQ ID NO 163
<211> LENGTH: 120
<212> TYPE: PRT
<213> ORGANISM: Artificial Sequence
<220> FEATURE:
<223> OTHER INFORMATION: recombinant scFv - VH sequence
```

```
<400> SEQUENCE: 163

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 164
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 165
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 165

Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45
```

Val Gly Phe Ile Asp Pro Asp Asp Pro Tyr Tyr Ala Thr Trp Ala
        50                  55                  60

Lys Gly Arg Phe Thr Ile Ser Arg Asp Asn Ser Lys Asn Thr Ala Tyr
 65                  70                  75                  80

Leu Gln Met Asn Ser Leu Arg Ala Glu Asp Thr Ala Thr Tyr Tyr Cys
                85                  90                  95

Ala Gly Gly Asp His Asn Ser Gly Trp Gly Leu Asp Ile Trp Gly Gln
                100                 105                 110

Gly Thr Thr Val Thr Val Ser Ser
        115                 120

<210> SEQ ID NO 166
<211> LENGTH: 120
<212> TYPE: PRT
<213> ORGANISM: Artificial Sequence
<220> FEATURE:
<223> OTHER INFORMATION: recombinant scFv - VH sequence

<400> SEQUENCE: 166

Glu Val Gln Leu Val Glu Ser Gly Gly Gly Ser Val Gln Pro Gly Gly
 1               5                  10                  15

Ser Leu Arg Leu Ser Cys Thr Ala Ser Gly Phe Ser Leu Thr Asp Tyr
                20                  25                  30

Tyr Tyr Met Thr Trp Val Arg Gln Ala Pro Gly Lys Gly Leu Glu Trp
            35                  40                  45

Val Gly Phe Ile Asp Pro Asp Asp Pro Tyr Tyr Ala Thr Trp Ala
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Gly Gly Asp His Asn Ser Gly Trp Gly Leu Asp Ile Trp Gly Gln
                100                 105                 110

Gly Thr Thr Val Thr Val Ser Ser
        115                 120

<210> SEQ ID NO 167
<211> LENGTH: 231
<212> TYPE: PRT
<213> ORGANISM: Artificial
<220> FEATURE:
<223> OTHER INFORMATION: recombinant scFv - VL acceptor sequence
<220> FEATURE:
<221> NAME/KEY: MISC_FEATURE
<222> LOCATION: (24)..(73)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least three and up to 50 amino acids can be present

<400> SEQUENCE: 167

Glu Ile Val Met Thr Gln Ser Pro Ser Thr Leu Ser Ala Ser Val Gly
 1               5                  10                  15

Asp Arg Val Ile Ile Thr Cys Xaa Xaa Xaa Xaa Xaa Xaa Xaa Xaa
                20                  25                  30

```
Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 168
<211> LENGTH: 231
<212> TYPE: PRT
<213> ORGANISM: Artificial
<220> FEATURE:
<223> OTHER INFORMATION: recombinant scFv - VL acceptor sequence
<220> FEATURE:
<221> NAME/KEY: MISC_FEATURE
<222> LOCATION: (24)..(73)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least three and up to 50 amino acids can be present

<400> SEQUENCE: 168

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80
```

-continued

```
Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Gly Val Pro Ser Arg Phe
        130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 169
<211> LENGTH: 232
<212> TYPE: PRT
<213> ORGANISM: Artificial
<220> FEATURE:
<223> OTHER INFORMATION: recombinant scFv - VH acceptor sequence
<220> FEATURE:
<221> NAME/KEY: MISC_FEATURE
<222> LOCATION: (26)..(75)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least three and up to 50 amino acids can be present

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Ser Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125
```

```
Xaa Xaa Xaa Xaa Xaa Xaa Xaa Xaa Xaa Xaa Arg Phe Thr Ile Ser
        130                 135                 140

Arg Asp Asn Ser Lys Asn Thr Leu Tyr Leu Gln Met Asn Ser Leu Arg
145                 150                 155                 160

Ala Glu Asp Thr Ala Val Tyr Tyr Cys Ala Lys Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 170
<211> LENGTH: 231
<212> TYPE: PRT
<213> ORGANISM: Artificial
<220> FEATURE:
<223> OTHER INFORMATION: recombinant scFv - VH acceptor sequence
<220> FEATURE:
<221> NAME/KEY: MISC_FEATURE
<222> LOCATION: (26)..(75)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least three and up to 50 amino acids can be present

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Thr Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Arg Phe Thr Ile Ser
    130                 135                 140

Arg Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175
```

```
Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
        210                 215                 220

Gly Thr Leu Val Thr Val Ser
225                 230

<210> SEQ ID NO 171
<211> LENGTH: 232
<212> TYPE: PRT
<213> ORGANISM: Artificial
<220> FEATURE:
<223> OTHER INFORMATION: recombinant scFv - VH acceptor sequence
<220> FEATURE:
<221> NAME/KEY: MISC_FEATURE
<222> LOCATION: (26)..(75)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least three and up to 50 amino acids can be present

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Thr Val Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Arg Phe Thr Ile Ser
        130                 135                 140

Lys Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa
            165                 170                 175

Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
        210                 215                 220
```

```
Gly Thr Leu Val Thr Val Ser Ser
225                 230

<210> SEQ ID NO 172
<211> LENGTH: 483
<212> TYPE: PRT
<213> ORGANISM: Artificial
<220> FEATURE:
<223> OTHER INFORMATION: recombinant scFv - acceptor sequence
<220> FEATURE:
<221> NAME/KEY: MISC_FEATURE
<222> LOCATION: (24)..(73)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (423)..(472)
<223> OTHER INFORMATION: X can be any naturally occurring amino acid.
      at least three and up to 50 amino acids can be present

<400> SEQUENCE: 172

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190
```

```
Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
        210                 215                 220

Thr Lys Leu Thr Val Leu Gly Gly Gly Gly Ser Gly Gly Gly
225                 230                 235                 240

Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Ala Ala Ser Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Ser Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa
        370                 375                 380

Xaa Xaa Xaa Xaa Xaa Xaa Arg Phe Thr Ile Ser Arg Asp Asn Ser Lys
385                 390                 395                 400

Asn Thr Leu Tyr Leu Gln Met Asn Ser Leu Arg Ala Glu Asp Thr Ala
                405                 410                 415

Val Tyr Tyr Cys Ala Lys Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 173
<211> LENGTH: 483
<212> TYPE: PRT
<213> ORGANISM: Artificial
<220> FEATURE:
<223> OTHER INFORMATION: recombinant scFv - acceptor sequence
<220> FEATURE:
<221> NAME/KEY: MISC_FEATURE
<222> LOCATION: (24)..(73)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least three and up to 50 amino acids can be present
```

```
<220> FEATURE:
<221> NAME/KEY: MISC_FEATURE
<222> LOCATION: (277)..(326)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (423)..(472)
<223> OTHER INFORMATION: X can be any naturally occurring amino acid.
      at least three and up to 50 amino acids can be present

<400> SEQUENCE: 173

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Gly Val Pro Ser Arg Phe
        130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Phe Gly Gln Gly
        210                 215                 220

Thr Lys Leu Thr Val Leu Gly Gly Gly Gly Ser Gly Gly Gly
225                 230                 235                 240

Ser Gly Gly Gly Gly Ser Gly Gly Gly Ser Glu Val Gln Leu Val
            245                 250                 255

Glu Ser Gly Gly Gly Leu Val Gln Pro Gly Gly Ser Leu Arg Leu Ser
            260                 265                 270

Cys Thr Ala Ser Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
```

```
                325                 330                 335
Glu Trp Val Gly Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa Xaa Xaa Xaa Xaa Xaa
                370                 375                 380

Xaa Xaa Xaa Xaa Xaa Xaa Arg Phe Thr Ile Ser Arg Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa
                435                 440                 445

Xaa Xaa Xaa Xaa Xaa Xaa Xaa Xaa Xaa Xaa Xaa Xaa Xaa Xaa
                450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 174
<211> LENGTH: 483
<212> TYPE: PRT
<213> ORGANISM: Artificial
<220> FEATURE:
<223> OTHER INFORMATION: recombinant scFv - acceptor sequence
<220> FEATURE:
<221> NAME/KEY: MISC_FEATURE
<222> LOCATION: (24)..(73)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (423)..(472)
<223> OTHER INFORMATION: X can be any naturally occurring amino acid.
      at least three and up to 50 amino acids can be present

<400> SEQUENCE: 174

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa
                35                  40                  45
```

-continued

```
Xaa Xaa Xaa Xaa Xaa Xaa Xaa Xaa Xaa Xaa Xaa Xaa Xaa Xaa
    50                  55                  60
Xaa Xaa Xaa Xaa Xaa Xaa Xaa Xaa Trp Tyr Gln Gln Lys Pro Gly
65                  70                  75                  80
Lys Ala Pro Lys Leu Leu Ile Tyr Xaa Xaa Xaa Xaa Xaa Xaa Xaa
                85                  90                  95
Xaa Xaa Xaa Xaa Xaa Xaa Xaa Xaa Xaa Xaa Xaa Xaa Xaa Xaa Xaa
                100                 105                 110
Xaa Xaa Xaa Xaa Xaa Xaa Xaa Xaa Xaa Xaa Xaa Xaa Xaa Xaa Xaa
                115                 120                 125
Xaa Xaa Xaa Xaa Xaa Xaa Xaa Xaa Xaa Gly Val Pro Ser Arg Phe
                130                 135                 140
Ser Gly Ser Gly Ser Gly Thr Glu Phe Thr Leu Thr Ile Ser Ser Leu
145                 150                 155                 160
Gln Pro Asp Asp Phe Ala Thr Tyr Tyr Cys Xaa Xaa Xaa Xaa Xaa
                165                 170                 175
Xaa Xaa Xaa Xaa Xaa Xaa Xaa Xaa Xaa Xaa Xaa Xaa Xaa Xaa Xaa
                180                 185                 190
Xaa Xaa Xaa Xaa Xaa Xaa Xaa Xaa Xaa Xaa Xaa Xaa Xaa Xaa Xaa
                195                 200                 205
Xaa Xaa Xaa Xaa Xaa Xaa Xaa Xaa Xaa Xaa Xaa Phe Gly Gln Gly
                210                 215                 220
Thr Lys Leu Thr Val Leu Gly Gly Gly Gly Ser Gly Gly Gly Gly
225                 230                 235                 240
Ser Gly Gly Gly Gly Ser Gly Gly Gly Gly Ser Glu Val Gln Leu Val
                245                 250                 255
Glu Ser Gly Gly Gly Leu Val Gln Pro Gly Gly Ser Leu Arg Leu Ser
                260                 265                 270
Cys Thr Val Ser Xaa Xaa Xaa Xaa Xaa Xaa Xaa Xaa Xaa Xaa
                275                 280                 285
Xaa Xaa Xaa Xaa Xaa Xaa Xaa Xaa Xaa Xaa Xaa Xaa Xaa Xaa Xaa
                290                 295                 300
Xaa Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Trp Val Arg Gln Ala Pro Gly Lys Gly Leu
                325                 330                 335
Glu Trp Val Gly Xaa Xaa Xaa Xaa Xaa Xaa Xaa Xaa Xaa Xaa Xaa
                340                 345                 350
Xaa Xaa Xaa Xaa Xaa Xaa Xaa Xaa Xaa Xaa Xaa Xaa Xaa Xaa Xaa
                355                 360                 365
Xaa Xaa Xaa Xaa Xaa Xaa Xaa Xaa Xaa Xaa Xaa Xaa Xaa Xaa Xaa
                370                 375                 380
Xaa Xaa Xaa Xaa Xaa Xaa Arg Phe Thr Ile Ser Lys Asp Thr Ser Lys
385                 390                 395                 400
Asn Thr Val Tyr Leu Gln Met Asn Ser Leu Arg Ala Glu Asp Thr Ala
                405                 410                 415
Val Tyr Tyr Cys Ala Arg Xaa Xaa Xaa Xaa Xaa Xaa Xaa Xaa Xaa
                420                 425                 430
Xaa Xaa Xaa Xaa Xaa Xaa Xaa Xaa Xaa Xaa Xaa Xaa Xaa Xaa Xaa
                435                 440                 445
Xaa Xaa Xaa Xaa Xaa Xaa Xaa Xaa Xaa Xaa Xaa Xaa Xaa Xaa Xaa
                450                 455                 460
```

Xaa Xaa Xaa Xaa Xaa Xaa Xaa Trp Gly Gln Gly Thr Leu Val Thr
465                 470                 475                 480

Val Ser Ser

<210> SEQ ID NO 175
<211> LENGTH: 248
<212> TYPE: PRT
<213> ORGANISM: Artificial Sequence
<220> FEATURE:
<223> OTHER INFORMATION: recombinant scFv

<400> SEQUENCE: 175

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Gly Ser Ser
            20                  25                  30

Leu Ala Trp Tyr Gln Gln Lys Pro Gly Lys Ala Pro Lys Leu Leu Ile
        35                  40                  45

Tyr Thr Ala Ala Asn Leu Ala Ser Gly Val Pro Ser Arg Phe Ser Gly
    50                  55                  60

Ser Arg Ser Gly Ala Glu Phe Thr Leu Thr Ile Ser Ser Leu Gln Pro
65                  70                  75                  80

Asp Asp Phe Ala Thr Tyr Tyr Cys Gln Asn Phe Ala Thr Ser Asp Thr
                85                  90                  95

Val Thr Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Lys Ala Ser Gly Phe Ser Leu Asn Thr
145                 150                 155                 160

Asn Tyr Trp Met Cys Trp Val Arg Gln Ala Pro Gly Lys Gly Leu Glu
                165                 170                 175

Trp Val Gly Cys Met Tyr Thr Gly Ser Tyr Asn Arg Ala Tyr Tyr Ala
            180                 185                 190

Ser Trp Ala Lys Gly Arg Phe Thr Ser Ser Lys Asp Thr Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Lys Gly Ser Asn Trp Tyr Ser Asp Leu Trp Gly Gln
225                 230                 235                 240

Gly Thr Leu Val Thr Val Ser Ser
                245

<210> SEQ ID NO 176
<211> LENGTH: 251
<212> TYPE: PRT
<213> ORGANISM: Artificial Sequence
<220> FEATURE:
<223> OTHER INFORMATION: recombinant scFv

<400> SEQUENCE: 176

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
            20                  25                  30

```
Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ala Asn Tyr Ala Tyr Ser Ala
                85                  90                  95

Gly Tyr Gly Ala Ala Phe Gly Gln Gly Thr Lys Leu Thr Val Leu Gly
            100                 105                 110

Gly Gly Gly Gly Ser Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Thr Val Ser Gly Phe Ser
145                 150                 155                 160

Leu Asn Thr Tyr Tyr Met Asn Trp Val Arg Gln Ala Pro Gly Lys Gly
                165                 170                 175

Leu Glu Trp Val Gly Ile Ile Ala Pro Asp Asp Thr Thr Tyr Tyr Ala
            180                 185                 190

Ser Trp Ala Lys Ser Arg Ser Thr Ile Ser Arg Asp Thr Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Arg Ser Gly Asp Thr Thr Ala Trp Gly Ala Asp Ile
225                 230                 235                 240

Trp Gly Gln Gly Thr Leu Val Thr Val Ser Ser
                245                 250

<210> SEQ ID NO 177
<211> LENGTH: 250
<212> TYPE: PRT
<213> ORGANISM: Artificial Sequence
<220> FEATURE:
<223> OTHER INFORMATION: recombinant scFv

<400> SEQUENCE: 177

Glu Ile Val Met Thr Gln Ser Pro Ser Thr Leu Ser Ala Ser Val Gly
1               5                   10                  15

Asp Arg Val Ile Ile Thr Cys Gln Ala Asp Gln Ser Ile Tyr Ile Trp
            20                  25                  30

Leu Ser Trp Tyr Gln Gln Lys Pro Gly Lys Ala Pro Lys Leu Leu Ile
            35                  40                  45

Tyr Lys Ala Ser Thr Leu Glu Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Asn Ala His Tyr Ser Thr
                85                  90                  95

Asn Gly Gly Thr Phe Gly Gln Gly Thr Lys Leu Thr Val Leu Gly Gly
            100                 105                 110

Gly Gly Ser Gly Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140
```

```
Pro Gly Gly Ser Leu Arg Leu Ser Cys Ala Ala Ser Gly Phe Ser Leu
145                 150                 155                 160

Ser Asp Tyr Tyr Met Cys Trp Val Arg Gln Ala Pro Gly Lys Gly Leu
                165                 170                 175

Glu Trp Val Ser Cys Leu Asp Tyr Phe Gly Ser Thr Asp Asp Ala Ser
            180                 185                 190

Trp Ala Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
210                 215                 220

Tyr Cys Ala Lys Thr Asp Asp Ser Arg Gly Trp Gly Leu Asn Ile Trp
225                 230                 235                 240

Gly Gln Gly Thr Leu Val Thr Val Ser Ser
                245                 250
```

<210> SEQ ID NO 178
<211> LENGTH: 251
<212> TYPE: PRT
<213> ORGANISM: Artificial Sequence
<220> FEATURE:
<223> OTHER INFORMATION: recombinant scFv

<400> SEQUENCE: 178

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
                20                  25                  30

Leu Ala Trp Tyr Gln Gln Lys Pro Gly Lys Ala Pro Lys Leu Leu Ile
            35                  40                  45

Tyr Leu Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
                100                 105                 110

Gly Gly Gly Ser Gly Gly Gly Gly Ser Gly Gly Gly Gly Ser Gly Gly
            115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Ala Ala Ser Gly Phe Ser Leu
145                 150                 155                 160

Thr Asp Tyr Tyr Met Thr Trp Val Arg Gln Ala Pro Gly Lys Gly
                165                 170                 175

Leu Glu Trp Val Ser Phe Ile Asp Pro Asp Asp Pro Tyr Tyr Ala
            180                 185                 190

Thr Trp Ala Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
210                 215                 220

Tyr Tyr Cys Ala Lys Gly Asp His Asn Ser Gly Trp Gly Leu Asp Ile
225                 230                 235                 240

Trp Gly Gln Gly Thr Leu Val Thr Val Ser Ser
                245                 250
```

-continued

```
<210> SEQ ID NO 179
<211> LENGTH: 251
<212> TYPE: PRT
<213> ORGANISM: Artificial Sequence
<220> FEATURE:
<223> OTHER INFORMATION: recombinant scFv

<400> SEQUENCE: 179
```

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Ser Gly Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Thr Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250

```
<210> SEQ ID NO 180
<211> LENGTH: 251
<212> TYPE: PRT
<213> ORGANISM: Artificial Sequence
<220> FEATURE:
<223> OTHER INFORMATION: recombinant scFv

<400> SEQUENCE: 180
```

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

```
Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Val Tyr Leu Ala Ser Thr
                 85                  90                  95

Asn Gly Ala Asn Phe Gly Gln Gly Thr Lys Leu Thr Val Leu Gly Gly
            100                 105                 110

Gly Gly Gly Ser Gly Gly Gly Ser Gly Gly Gly Ser Gly Gly
        115                 120                 125

Gly Gly Ser Glu Val Gln Leu Val Glu Ser Gly Gly Leu Val Gln
        130                 135                 140

Pro Gly Gly Ser Leu Arg Leu Ser Cys Thr Ala Ser Gly Phe Ser Leu
145                 150                 155                 160

Thr Asp Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Thr Ser Lys Asn
        195                 200                 205

Thr Val Tyr Leu Gln Met Asn Ser Leu Arg Ala Glu Asp Thr Ala Val
        210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250

<210> SEQ ID NO 181
<211> LENGTH: 20
<212> TYPE: PRT
<213> ORGANISM: Artificial Sequence
<220> FEATURE:
<223> OTHER INFORMATION: synthetic linker sequence

<400> SEQUENCE: 181

Gly Gly Gly Gly Ser Gly Gly Gly Ser Gly Gly Gly Gly Ser Gly
1               5                   10                  15

Gly Gly Gly Ser
            20

<210> SEQ ID NO 182
<211> LENGTH: 5
<212> TYPE: PRT
<213> ORGANISM: Artificial Sequence
<220> FEATURE:
<223> OTHER INFORMATION: synthetic peptide

<400> SEQUENCE: 182

Gly Gly Gly Gly Ser
1               5

<210> SEQ ID NO 183
<211> LENGTH: 13
<212> TYPE: PRT
<213> ORGANISM: Artificial Sequence
<220> FEATURE:
<223> OTHER INFORMATION: synthetic peptide

<400> SEQUENCE: 183

Lys Phe Met Asp Val Tyr Gln Arg Ser Tyr Cys His Pro
1               5                   10
```

```
<210> SEQ ID NO 184
<211> LENGTH: 14
<212> TYPE: PRT
<213> ORGANISM: Artificial Sequence
<220> FEATURE:
<223> OTHER INFORMATION: synthetic peptide

<400> SEQUENCE: 184

Lys Phe Met Asp Val Tyr Gln Arg Ser Tyr Cys Lys Leu His
1               5                   10
```

STABLE AND SOLUBLE ANTIBODIES INHIBITING VEGF

RELATED INFORMATION

The present application is a divisional of 14/741,430 filed Jun. 16, 2015, now U.S. Pat. No. 9,873,737; which is a divisional of 13/708,575 filed Dec. 7, 2012, now U.S. Pat. No. 9,090,684; which is a divisional of 13/000,423 filed Jun. 25, 2009, now U.S. Pat. No. 8,349,322; which is a 371 application, which claims priority from PCT/CH2009/000220, of 25 Jun. 2009, which claims priority to U.S. 61/133,212 filed on Jun. 25, 2008, to U.S. 61/075,697 of 25 Jun. 2008, to U.S. 61/155,041 of 24 Feb. 2009, and to U.S. 61/075,692 of 25 Jun. 2008.

The contents of any patents, patent applications, and references cited throughout this specification are hereby incorporated by reference in their entireties.

BACKGROUND OF THE INVENTION

Angiogenesis is implicated in the pathogenesis of a variety of disorders including solid tumors, intraocular neovascular syndromes such as proliferative retinopathies or age-related macular degeneration (AMD), rheumatoid arthritis, and psoriasis (Folkman et al. J. Biol. Chem. 267:10931-10934 (1992); Klagsbrun et al. Annu. Rev. Physiol. 53:217-239 (1991); and Garner A, Vascular diseases. In: Pathobiology of ocular disease. A dynamic approach. Garner A, Klintworth G K, Eds. 2nd Edition Marcel Dekker, NY, pp 1625-1710 (1994)). In solid tumors, angiogenesis and growth of new vasculture permits survival of the tumor, and a correlation has been demonstrated between the density of microvessels in tumor sections and patient survival in breast and other cancers (Weidner et al. N Engl J Med 324:1-6 (1991); Horak et al. Lancet 340:1120-1124 (1992); and Macchiarini et al. Lancet 340:145-146 (1992)).

Vascular endothelial growth factor (VEGF) is a known regulator of angiogenesis and neovascularization, and has been shown to be a key mediator of neovascularization associated with tumors and intraocular disorders (Ferrara et al. Endocr. Rev. 18:4-25 (1997)). The VEGF mRNA is overexpressed in many human tumors, and the concentration of VEGF in eye fluids are highly correlated to the presence of active proliferation of blood vessels in patients with diabetic and other ischemia-related retinopathies (Berkman et al., J Clin Invest 91:153-159 (1993); Brown et al. Human Pathol. 26:86-91 (1995); Brown et al. Cancer Res. 53:4727-4735 (1993); Mattern et al. Brit. J. Cancer. 73:931-934 (1996); and Dvorak et al. Am J. Pathol. 146:1029-1039 (1995); Aiello et al. N. Engl. J. Med. 331:1480-1487 (1994)). In addition, recent studies have shown the presence of localized VEGF in choroidal neovascular membranes in patients affected by AMD (Lopez et al. Invest. Ophtalmo. Vis. Sci. 37:855-868 (1996)). Anti-VEGF neutralizing antibodies can be used to suppress the growth of a variety of human tumor cell lines in nude mice and also inhibit intraocular angiogenesis in models of ischemic retinal disorders (Kim et al. Nature 362:841-844 (1993); Warren et al. J. Clin. Invest 95:1789-1797 (1995); Borgstrom et al. Cancer Res. 56:4032-4039 (1996); and Melnyk et al. Cancer Res. 56:921-924 (1996)) (Adamis et al. Arch. Opthalmol. 114: 66-71 (1996)).

Thus, there is a need for anti-VEGF monoclonal antibodies capable of being used for the treatment of solid tumors and various neovascular intraocular diseases.

SUMMARY OF THE INVENTION

The invention provides soluble and stable anti-VEGF immunobinders comprising CDRs from rabbit monoclonal antibodies. Said antibodies are designed for the diagnosis and/or treatment of VEGF-mediated disorders. The hybridomas, nucleic acids, vectors and host cells for expression of the recombinant antibodies of the invention, methods for isolating them and the use of said antibodies in medicine are also disclosed.

BRIEF DESCRIPTION OF THE DRAWINGS

FIG. 1a shows the data obtained for 511max: Ka (1/Ms): 6.59E+05; SE (ka): 1.10E+03; kd(1/s): 4.40E-05; SE(kd): 6.30E-07; KD(M): 6.67E-11. FIG. 1b shows the data obtained for 578max: Ka (1/Ms): 7.00E+05; SE (ka): 1.40E+03; kd(1/s): 3.07E-04; SE(kd): 8.50E-07; KD(M): 4.39E-10.

FIG. 2a shows the data obtained for human VEGF165: Ka (1/Ms): 7.00E+05; SE (ka): 1.40E+03; kd(1/s): 3.07E-04; SE(kd): 8.50E-07; KD(M): 4.39E-10. FIG. 2b shows the data obtained for mouse VEGF164: Ka (1/Ms): 1.03E+06; SE (ka): 2.30E+03; kd(1/s): 4.40E-04; SE(kd): 9.40E-07; KD(M): 4.29E-10. FIG. 2c shows the data obtained for rat VEGF164: Ka (1/Ms): 8.83E+05; SE (ka): 2.50E+03; kd(1/s): 5.28E-04; SE(kd): 1.20E-06; KD(M): 5.98E-10.

FIG. 3a shows the data obtained for human VEGF165: Ka (1/Ms): 7.00E+05; SE (ka): 1.4E+03; kd(1/s): 3.07E-04; SE(kd): 8.50E-07; KD(M): 4.39E-10. FIG. 3b shows the data obtained for human VEGF121: Ka (1/Ms): 5.87E+05; SE (ka): 1.20E+03; kd(1/s): 5.58E-04; SE(kd): 9.60E-07; KD(M): 9.50E-11. FIG. 3c shows the data obtained for human VEGF110: Ka (1/Ms): 5.23E+05; SE (ka): 1.30E+03; kd(1/s): 7.22E-04; SE(kd): 8.10E-07; KD(M): 1.38E-09.

FIG. 4a shows the data obtained for 578max: Ka (1/Ms): 7.00E+05; SE (ka): 1.40E+03; kd(1/s): 3.07E-04; SE(kd): 8.50E-07; KD(M): 4.39E-10. FIG. 4b shows the data obtained for 578minmax: Ka (1/Ms): 8.06E+05; SE (ka): 2.10E+03; kd(1/s): 5.04E-04; SE(kd): 1.10E-06; KD(M): 6.25E-10. FIG. 4c shows the data obtained for 578wt-His: Ka (1/Ms): 8.45E+05; SE (ka): 1.60E+03; kd(1/s): 1.69E-04; SE(kd): 7.60E-07; KD(M): 2.00E-10.

FIG. 5a: 578minmax (ESBA903): Tm=71.1° C.; FIG. 5b: 578minmax_DHP (#961): Tm=70.2° C.; FIG. 5c: 578max (821): Tm=70.4° C.

FIG. 7a: 578max (#821). The V50 was 27.24% FIG. 7b: 578minmax (ESBA903). The V50 was 28.13. FIG. 7c: 578minmax_DHP (#961). The V50was 32.36%.

FIG. 8*a*: Comparison of Lucentis and 511max (#802) in VEGFR2 competition ELISA. $R^2$ of Lucentis: 0.9417; $R^2$ of ESBA802: 0.9700. EC50 of Lucentis: 7.137 nM; EC50 of #802: 0.8221 nM. FIG. 8*b*: Comparison of Lucentis and 578max (#821). in VEGFR2 competition ELISA. FIG. 8*c*: Comparison of Lucentis, 511maxC-his and 534max in HUVEC assay. $R^2$ of Lucentis 0.9399; $R^2$ of EP511maxC-his: 0.9313, $R^2$ of EP534max: 0.7391. EC50 of Lucentis: 0.08825 nM, EC50 of 511maxC-his: 0.7646 nM, EC50 of 534max: 63.49 nM. FIG. 8*d*: Comparison of Lucentis, 578min and 578max in HUVEC assay. $R^2$ of Lucentis: 0.9419, $R^2$ of EP578min: 0.8886, $R^2$ of EP578max: 0.9274. EC50 of Lucentis: 0.1529 nM, EC50 of 578min: 1.528 nM, EC50 of 578max: 0.1031 nM.

FIG. 10*a* illustrates the data obtained for mouse VEGF. The EC50 was 0.1196 nM for V1253 and 0.06309 nM for 578minmax, whereas the $R^2$ was 0.02744 for Lucentis, 0.9348 for V1253 and 0.9767 for EP578minmax. Lucentis did not inhibit HUVEC proliferation induced by mouse VEGF. FIG. 10*b* illustrates the data obtained for rat VEGF. The EC50 was 1.597 nM for V1253 and 0.06974 nM for 578minmax, whereas the $R^2$ was 00.7664 for V1253 and 0.6635 for 578minmax.

FIG. 12*a* shows the results obtained for #803 (511max). The EC50 was 5.990 nM and had a statistical spread between 2.060 and 17.41 nM whereas the $R^2$ was 0.5800. FIG. 12*b* shows the results obtained for ESBA903 (578minmax). The EC50 was 3.989 and had a statistical spread between 1.456 and 10.93 nM whereas the $R^2$ was 0.3920. FIG. 12*c* shows the area of dye leakage for Lucentis. The EC50 could not be calculated for Lucentis due to the poor fit of the curve.

FIG. 13*a* illustrates the anti-permeability efficacy of Avastin upon VEGF induced retinal vascular leakage in rats—dose response. Avastin inhibits hVEGF-induced retinal vascular permeability. Premixed before injection. Approximately equimolar, 3 fold, or 10 fold excess. *$p<0.05$ (VEGF s. BSA), $p<0.05$ (Avastin treated vs. VEGF). FIG. 13***b* shows the anti-permeability efficacy of ESBA903 upon VEGF induced retinal vascular leakage in rats. Dose response (pre-mixed, ivt). Complete inhibition of hVEGF-induced retinal vascular permeability by ESBA903. Premixed before injection. Approximately equimolar, 3 fold, or 10 fold excess. *$p<0.05$ (VEGF s. BSA), **$p<0.05$ (ESBA903 treated vs. VEGF).

DETAILED DESCRIPTION

The invention provides soluble and stable anti-VEGF imunobinders comprising CDRs from rabbit monoclonal antibodies. Said imunobinders are designed for the diagnosis and/or treatment of VEGF-mediated disorders. The hybridomas, nucleic acids, vectors and host cells for expression of the recombinant antibodies of the invention, methods for isolating them and the use of said antibodies in medicine are also disclosed.

Definitions

In order that the present invention may be more readily understood, certain terms will be defined as follows. Additional definitions are set forth throughout the detailed description.

The term "VEGF" refers to the 165-amino acid vascular endothelial cell growth factor, and related 121-, 189-, and 206-amino acid vascular endothelial cell growth factors, as described by Leung et al., Science 246:1306 (1989), and Houck et al., Mol. Endocrin. 5:1806 (1991) together with the naturally occurring allelic and processed forms of those growth factors.

The term "VEGF receptor" or "VEGFr" refers to a cellular receptor for VEGF, ordinarily a cell-surface receptor found on vascular endothelial cells, as well as variants thereof which retain the ability to bind hVEGF. One example of a VEGF receptor is the fms-like tyrosine kinase (flt), a transmembrane receptor in the tyrosine kinase family. DeVries et al., Science 255:989 (1992); Shibuya et al., Oncogene 5:519 (1990). The flt receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the flk-1 receptor (also referred to as KDR). Matthews et al., Proc. Nat. Acad. Sci. 88:9026 (1991); Terman et al., Oncogene 6:1677 (1991); Terman et al., Biochem. Biophys. Res. Commun. 187:1579 (1992). Binding of VEGF to the flt receptor results in the formation of at least two high molecular weight complexes, having an apparent molecular weight of 205,000 and 300,000 Daltons. The 300,000 Dalton complex is believed to be a dimer comprising two receptor molecules bound to a single molecule of VEGF.

The term "rabbit" as used herein refers to an animal belonging to the family of the leporidae.

The term "antibody" as used herein is a synonym for "immunoglobulin." Antibodies according to the present invention may be whole immunoglobulins or fragments thereof, comprising at least one variable domain of an immunoglobulin, such as single variable domains, Fv (Skerra A. and Pluckthun, A. (1988) *Science* 240:1038-41), scFv (Bird, R. E. et al. (1988) *Science* 242:423-26; Huston, J. S. et al. (1988) *Proc. Natl. Acad. Sci. USA* 85:5879-83), Fab, (Fab')2 or other fragments well known to a person skilled in the art.

Figure 15:
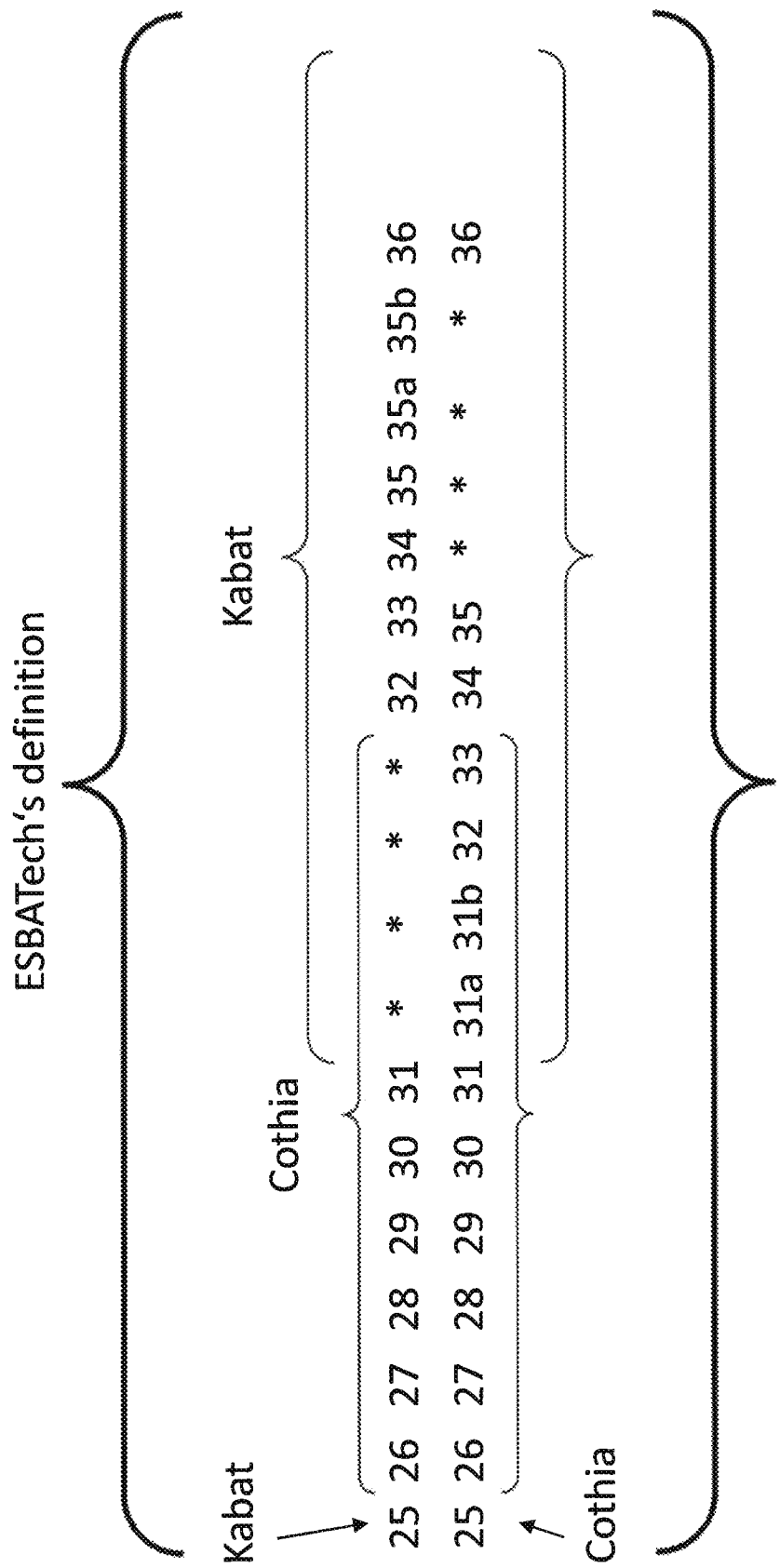
FIG. 15 illustrates the definition of CDR1 of VH as used herein.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the following residues (Kabat numbering): It starts with position 26 and ends prior to position 36. This is basically a fusion of CDR H1 as differently defined by Kabat and Chotia (see also FIG. 15 for illustration).

The term "antibody framework", or sometimes only "framework", as used herein refers to the part of the variable domain, either VL or VH, which serves as a scaffold for the antigen binding loops (CDRs) of this variable domain. In essence it is the variable domain without the CDRs. The term "single chain antibody", "single chain Fv" or "scFv" is intended to refer to a molecule comprising an antibody heavy chain variable domain (or region; $V_H$) and an antibody light chain variable domain (or region; $V_L$) connected by a linker. Such scFv molecules can have the general structures: $NH_2$-$V_L$-linker-$V_H$-COOH or $NH_2$-$V_H$-linker-$V_L$-COOH.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared ×100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment can be provided using, for instance, the method of Needleman et al. (1970) *J. Mol. Biol.* 48: 443-453, implemented conveniently by computer programs such as the Align program (DNAstar, Inc.). The percent identity between two amino acid sequences can also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (Accelrys, Inc., San Diego, Calif.), using either a Blossum 62 matrix or a PAM250 matrix, and a gap weight of 16, 14, 12, 10, 8, 6, or 4 and a length weight of 1, 2, 3, 4, 5, or 6.

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared ×100. For instance, if 6 of 10 of the positions in two sequences are matched and 2 of 10 positions contain conservative substitutions, then the two sequences have 80% positive similarity.

As used herein, the term "conservative sequence modifications" is intended to refer to amino acid modifications that do not negatively affect or alter the binding characteristics of the antibody containing the amino acid sequence. Such conservative sequence modifications include nucleotide and amino acid substitutions, additions and deletions. For example, modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-VEGF antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

"Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability can be exhibited at the single residue level, multiple residue level, multiple residue with gaps etc. Residues can exhibit conservation of the identical residue or can be conserved at the class level. Examples of amino acid classes include polar but uncharged R groups (Serine, Threonine, Asparagine and Glutamine); positively charged R groups (Lysine, Arginine, and Histidine); negatively charged R groups (Glutamic acid and Aspartic acid); hydrophobic R groups (Alanine, Isoleucine, Leucine, Methionine, Phenylalanine, Tryptophan, Valine and Tyrosine); and special amino acids (Cysteine, Glycine and Proline). Other classes are known to one of skill in the art and may be defined using structural determinations or other data to assess substitutability. In that sense, a substitutable amino acid can refer to any amino acid which can be substituted and maintain functional conservation at that position.

It will be recognized, however, that amino acids of the same class may vary in degree by their biophysical properties. For example, it will be recognized that certain hydrophobic R groups (e.g., Alanine, Serine, or Threonine) are more hydrophilic (i.e., of higher hydrophilicity or lower hydrophobicity) than other hydrophobic R groups (e.g., Valine or Leucine). Relative hydrophilicity or hydrophobicity can be determined using art-recognized methods (see, e.g., Rose et al., *Science*, 229: 834-838 (1985) and Cornette et al., *J. Mol. Biol.*, 195: 659-685 (1987)).

As used herein, when one amino acid sequence (e.g., a first $V_H$ or $V_L$ sequence) is aligned with one or more additional amino acid sequences (e.g., one or more VH or VL sequences in a database), an amino acid position in one sequence (e.g., the first $V_H$ or $V_L$ sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "multiplicity" of sequences), and typically refers to a collection of tens, hundreds or even thousands of antibody amino acid sequences. An antibody database can store amino acid sequences of, for example, a collection of antibody $V_H$ regions, antibody $V_L$ regions or both, or can store a collection of scFv sequences comprised of $V_H$ and $V_L$ regions. Preferably, the database is stored in a searchable, fixed medium, such as on a computer within a searchable computer program. In one embodiment, the antibody database is a database comprising or consisting of germline antibody sequences. In another embodiment, the antibody database is a database comprising or consisting of mature (i.e., expressed) antibody sequences (e.g., a Kabat database of mature antibody sequences, e.g., a KBD database). In yet another embodiment, the antibody database comprises or consists of functionally selected sequences (e.g., sequences selected from a QC assay).

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, Fundamental Immunology (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a single domain antibody such as a Dab fragment (Ward et al., (1989) *Nature* 341:544-546), which consists of a $V_H$ or $V_L$ domain, a Camelid (see Hamers-Casterman, et al., Nature 363:446-448 (1993), and Dumoulin, et al., Protein Science 11:500-515 (2002)) or a Shark antibody (e.g., shark Ig-NARs Nanobodies®); and (vii) a nanobody, a heavy chain region containing the variable domain and two constant domains.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is stability (e.g., thermal stability). In another embodiment, the functional property is solubility (e.g., under cellular conditions). In yet another embodiment, the functional property is non-aggregation. In still another embodiment, the functional property is protein expression (e.g., in a prokaryotic cell). In yet another embodiment the functional property is a refolding efficiency following an inclusion body solubilization in a corresponding purification process. In certain embodiments, antigen binding affinity is not a functional property desired for improvement.

The term "epitope" or "antigenic determinant" refers to a site on an antigen (e.g., on VEGF) to which an immunoglobulin or antibody specifically binds. An epitope typically includes at least 3, 4, 5, 6, 7, 8, 9, 10, 11, 12, 13, 14 or 15 consecutive or non-consecutive amino acids in a unique spatial conformation. See, e.g., *Epitope Mapping Protocols in Methods in Molecular Biology*, Vol. 66, G. E. Morris, Ed. (1996).

The terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower.

The term "$K_D$," or "$K_d$" refers to the dissociation equilibrium constant of a particular antibody-antigen interaction. Typically, the antibodies of the invention bind to VEGF with a dissociation equilibrium constant ($K_D$) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

The terms "neutralizes VEGF," "inhibits VEGF," and "blocks VEGF" are used interchangeably to refer to the ability of an antibody of the invention to prevent VEGF from interacting with one or more VEGF receptors such as VEGFR-1 and/or VEGFR-2, and, for example, triggering signal transduction.

A "recombinant immunobinder" as used herein refers to an immunobinder being produced by expression from recombinant DNA.

A "chimeric" immunobinder as used herein has a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies. Humanized antibody as used herein is a subset of chimeric antibodies.

"Humanized antibodies" as used herein are immunobinders that have been synthesized using recombinant DNA technology to circumvent immune response to foreign antigens. Humanization is a well-established technique for reducing the immunogenicity of monoclonal antibodies of xenogenic sources. This involves the choice of an acceptor framework, preferably a human acceptor framework, the extent of the CDRs from the donor immunobinder to be inserted into the acceptor framework and the substitution of residues from the donor framework into the acceptor framework. A general method for grafting CDRs into human acceptor frameworks has been disclosed by Winter in U.S. Pat. No. 5,225,539, which is hereby incorporated by reference in its entirety. U.S. Pat. No. 6,407,213 the teachings of which are incorporated by reference in its entirety, discloses a number of amino acid positions of the framework where a substitution from the donor immunobinder is preferred.

The term "nucleic acid molecule," refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector," refers to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

The term "host cell" refers to a cell into which an expression vector has been introduced. Host cells can include bacterial, microbial, plant or animal cells. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. Suitable microbes include *Saccharomyces cerevisiae* and *Pichia pastoris*. Suitable animal host cell lines include CHO (Chinese Hamster Ovary lines) and NS0 cells.

The terms "treat," "treating," and "treatment," refer to therapeutic or preventative measures described herein. The methods of "treatment" employ administration to a subject, in need of such treatment, an antibody of the present invention, for example, a subject having a VEGF-mediated disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "VEGF-mediated disorder" refers to any disorder, the onset, progression or the persistence of the symptoms or disease states of which requires the participation of VEGF. Exemplary VEGF-mediated disorders include, but are not limited to, age-related macular degeneration, neovascular glaucoma, diabetic retinopathy, retinopathy of prematurity, retrolental fibroplasia, breast carcinomas, lung carcinomas, gastric carcinomas, esophageal carcinomas, colorectal carcinomas, liver carcinomas, ovarian carcinomas, the comas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), Meigs' syndrome, rheumatoid arthritis, psoriasis and atherosclerosis.

The term "effective dose" or "effective dosage" refers to an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "subject" refers to any human or non-human animal. For example, the methods and compositions of the present invention can be used to treat a subject with a VEGF-mediated disorder.

The term "Min-graft" or "min" as used herein refers to a humanized variable domain that was generated by grafting of rabbit CDRs from a rabbit variable domain into a naturally occurring human acceptor framework (FW 1.4, SEQ ID No. 172). No changes in the framework regions are made. The framework itself was preselected for desirable functional properties (solubility and stability).

The term "Max-graft" or "max" as used herein refers to a humanized variable domain that was generated by grafting of rabbit CDRs from a rabbit variable domain into the "rabbitized", human acceptor framework "RabTor" (rFW1.4, SEQ ID No. 173), or into a derivative thereof referred to as rFW1.4(v2) (SEQ ID No. 174). The "RabTor" framework was prepared by incorporating conserved rabbit residues (other wise which are rather variable in other species) at framework positions generally involved in rabbit variable domain structure and stability, with the aim to generate a universally applicable framework that accepts virtually any set of rabbit CDRs without the need to graft donor framework residues other than at positions that are different in their presumable progenitor sequence, e.g. that were altered during somatic hypermutation and thus, possibly contribute to antigen binding. The presumable progenitor sequence is defined to be the closest rabbit germline counterpart and in case the closest germline counterpart could can not be established, the rabbit subgroup consensus or the consensus of rabbit sequences with a high percentage of similarity.

The term "Min-Max" or "minmax" as used herein refers to a humanized variable domain comprising of a "Min-graft" variable light chain combined with a "Max-graft" variable heavy chain.

The term "Max-Min" or "maxmin" as used herein refers to a humanized variable domain comprising of a "Max-graft" variable light chain combined with a "Min-graft" variable heavy chain.

Different nomenclatures were used for the generated immunobinders. These are typically identified by a number (e.g. #578). In those cases where a prefix such as EP or Epi was used (e.g. EP 578 which is identical to Epi 578), the same immunobinder is thereby indicated. Occasionally, an immunobinder received a second designation which is identified by the prefix "ESBA". For example ESBA903 designates the same immunobinder as 578minmax or EP578minmax or Epi578minmax.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending on the specific embodiment, selected definitions, embodiments or ranges may not apply.

Anti-VEGF Immunobinders

In one aspect, the present invention provides immunobinders that bind VEGF and thus are suitable to block the function of VEGF in vivo. The CDRs of these immunobinders are derived from rabbit anti-VEGF monoclonal antibodies which were obtained from rabbits that were immunized with human VEGF and/or a fragment thereof (SEQ ID No.1). To our knowledge, this is the first time that monoclonal anti-VEGF antibodies were obtained from rabbits and characterized in detail. Surprisingly, the affinities (Kd) were found to be extraordinarily high.

In certain embodiments, the invention provides an immunobinder, which specifically binds VEGF, comprising at least one of a CDRH1, a CDRH2, a CDRH3, a CDRL1, a CDRL2, or a CDRL3 amino acid sequence. Exemplary CDR amino acid sequences for use in the immunobinders of the invention are set forth in SEQ ID Nos: 2-72 (Tables 1-6).

TABLE 1

CDR H1 amino acid sequences of anti-VEGF immunobinders of the invention.

| Sequence Identifier | CDR-H1 | SEQ. ID No. |
| --- | --- | --- |
| 60-11-4 | GFPFSSGYWVC | 2 |
| 60-11-6 | GFSFSSGYWIC | 3 |
| 435 | GFSLNTNYWMC | 4 |
| 453 | GFSFSRSYYIY | 5 |
| 375 | GFSFTTTDYMC | 6 |
| 610 | GIDFSGAYYMG | 7 |
| 578 | GFSLTDYYYMT | 8 |
| 534 | GFSLSYYYMS | 9 |
| 567 | GFSLSDYYMC | 10 |
| 509 | GFSLSSYYMC | 11 |

TABLE 1-continued

CDR H1 amino acid sequences of anti-VEGF immunobinders of the invention.

| Sequence Identifier | CDR-H1 | SEQ. ID No. |
| --- | --- | --- |
| 511 | GFSLNTYYMN | 12 |
| 509maxII | GFSLSSYYMS | 13 |
| Consensus | GFSLSSGYYMC | 14 |

TABLE 2

CDR H2 amino acid sequences of anti VEGF immunobinders of the invention.

| Sequence Identifier | CDR-H2 | SEQ. ID No. |
| --- | --- | --- |
| 60 | CIYAGSSGSTYYASWAKG | 15 |
| 435 | CMYTGSYNRAYYASWAKG | 16 |
| 453 | CIDAGSSGILVYANWAKG | 17 |
| 375 | CILAGDGSTYYANWAKG | 18 |
| 610 | YIDYDGDRYYASWAKG | 19 |
| 578 | FIDPDDDPYYATWAKG | 20 |
| 534 | IIGPGDYTDYASWAKG | 21 |
| 567 | CLDYFGSTDDASWAKG | 22 |
| 509 | CLDYVGDTDYASWAKG | 23 |
| 511 | IIAPDDTTYYASWAKS | 24 |
| 509maxII | ILDYVGDTDYASWAKG | 25 |
| Consensus | CIDAGSDGDTYYASWAKG | 26 |

TABLE 3

CDR H3 amino acid sequences of anti VEGF immunobinders of the invention.

| Sequence Identifier | CDR-H3 | SEQ. ID No. |
| --- | --- | --- |
| 60 | GNNYYIYTDGGYAYAGLEL | 27 |
| 435 | GSNWYSDL | 28 |
| 453 | GDASYGVDSFMLPL | 29 |
| 375 | SDPASSWSFAL | 30 |
| 610 | SDYSSGWGTDI | 31 |
| 578 | GDHNSGWGLDI | 32 |
| 534 | GDDNSGWGEDI | 33 |
| 567 | TDDSRGWGLNI | 34 |
| 509 | TDDSRGWGLNI | 35 |
| 511 | SGDTTAWGADI | 36 |
| Consensus | GDDSSGYTDGGYAYWGLDI | 37 |

TABLE 4

CDR L1 amino acid sequences of anti-VEGF immunobinders of the invention.

| Sequence Identifier | CDR-L1 | SEQ. ID No. |
|---|---|---|
| 60 | QASQSISSYLS | 38 |
| 435 | QASQSIGSSLA | 39 |
| 453 | QSSQSVWNNNRLA | 40 |
| 375 | QASENINIWLS | 41 |
| 610 | QASQSISSWLS | 42 |
| 578 | QASEIIHSWLA | 43 |
| 534 | QASQSINIWLS | 44 |
| 567 | QADQSIYIWLS | 45 |
| 509 | QASQNIRIWLS | 46 |
| 511 | QASQSINIWCS | 47 |
| 511max | QASQSINIWLS | 48 |
| Consensus | QASQSININNWLS | 49 |

TABLE 5

CDR L2 amino acid sequences of anti-VEGF immunobinders of the invention.

| Sequence Identifier | CDR-L2 | SEQ. ID No. |
|---|---|---|
| 60 | KASTLAS | 50 |
| 435 | TAANLAS | 51 |
| 453 | YASTLAS | 52 |
| 375 | QASKLAS | 53 |
| 610 | QASTLAS | 54 |
| 578 | LASTLAS | 55 |
| 534 | KESTLAS | 56 |
| 567 | KASTLES | 57 |
| 509 | KASTLES | 58 |
| 511 | RASTLAS | 59 |
| Consensus | KASTLAS | 60 |

TABLE 6

CDR L3 amino acid sequences of anti-VEGF immunobinders of the invention.

| Sequence Identifier | CDR-L3 | SEQ. ID No. |
|---|---|---|
| 60 | QSNYGGSSSDYGNP | 61 |
| 435 | QNFATSDTVT | 62 |
| 453 | AGGYSSTSDNT | 63 |
| 375 | QNNYSYNRYGAP | 64 |
| 610 | QNNYGFRSYGGA | 65 |

TABLE 6-continued

CDR L3 amino acid sequences of anti-VEGF immunobinders of the invention.

| Sequence Identifier | CDR-L3 | SEQ. ID No. |
|---|---|---|
| 578 | QNVYLASTNGAN | 66 |
| 534 | QNNYDSGNNGFP | 67 |
| 567 | QNNAHYSTNGGT | 68 |
| 509 | QNNAHYSTNGGT | 69 |
| 511 | QANYAYSAGYGAA | 70 |
| Consensus | QNNYHYSSSTNGGT | 71 |

In one embodiment, the invention provides an immunobinder comprising at least one CDR having at least 75% similarity, preferably at least 75% identity, more preferably at least 80%, 85%, 90% 95%, even more preferably 100% identity to a consensus sequence of the group consisting of SEQ ID NO: 14, SEQ ID NO: 26, SEQ ID NO: 37, SEQ ID NO: 49, SEQ ID NO: 60 and SEQ ID NO: 71. Preferably, the VH of said immunobinder comprise the CDRs of the group consisting of SEQ ID NO: 14, SEQ ID NO: 26 and SEQ ID NO: 37 and/or the CDRs of the VL of said immunobinder comprise CDRs of the group consisting of SEQ ID NO: 49, SEQ ID NO: 60 and SEQ ID NO: 71. Preferably, the CDR is selected from the group consisting of SEQ ID NO: 2 to SEQ ID NO: 13, SEQ ID NO: 15 to SEQ ID NO: 25, SEQ ID NO: 27 to SEQ ID NO: 36, SEQ ID NO: 38 to SEQ ID NO: 48, SEQ ID NO: 50 to SEQ ID NO: 59 and SEQ ID NO: 61 to SEQ ID NO: 70.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 2, SEQ ID NO: 3, SEQ ID NO: 15, SEQ ID NO: 27, SEQ ID NO: 38, SEQ ID NO: 50 and SEQ ID NO: 61. Preferably, the VH of said immunobinder comprise the CDRs of the group consisting of SEQ ID NO: 2, SEQ ID NO: 15 and SEQ ID NO: 27 and/or the CDRs of the VL of said immunobinder comprise CDRs of the group consisting of SEQ ID NO: 38, SEQ ID NO: 50 and SEQ ID NO: 61. In another preferred embodiment, the VH of said immunobinder comprise the CDRs of the group consisting of SEQ ID NO: 3, SEQ ID NO: 15 and SEQ ID NO: 27 and/or the CDRs of the VL of said immunobinder comprise CDRs of the group consisting of SEQ ID NO: 38, SEQ ID NO: 50 and SEQ ID NO: 61.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 4, SEQ ID NO: 16, SEQ ID NO: 28, SEQ ID NO: 39, SEQ ID NO: 51, and SEQ ID NO: 62. Preferably, the VH of said immunobinder comprise the CDRs of the group consisting of SEQ ID NO: 4, SEQ ID NO: 16, SEQ ID NO: 28 and/or the CDRs of the VL of said immunobinder comprise CDRs of the group consisting of SEQ ID NO: 39, SEQ ID NO: 51, and SEQ ID NO: 62.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 5, SEQ ID NO: 17, SEQ ID NO: 29, SEQ ID NO: 40, SEQ ID NO: 52 and SEQ ID NO: 63. Preferably, the VH of said immunobinder comprise the CDRs of the group consisting of SEQ ID NO: 5, SEQ ID NO: 17, SEQ ID NO: 29 and/or the CDRs of the VL of said immunobinder comprise CDRs of the group consisting of SEQ ID NO: 40, SEQ ID NO: 52 and SEQ ID NO: 63.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 6, SEQ ID NO: 18, SEQ ID NO: 30, SEQ ID NO: 41, SEQ ID NO: 53 and SEQ ID NO: 64. Preferably, the VH of said immunobinder comprise the CDRs of the group consisting of SEQ ID NO: 6, SEQ ID NO: 18 and SEQ ID NO: 30 and/or the CDRs of the VL of said immunobinder comprise CDRs of the group consisting of SEQ ID NO: 41, SEQ ID NO: 53 and SEQ ID NO: 64.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 7, SEQ ID NO: 19, SEQ ID NO: 31, SEQ ID NO: 42, SEQ ID NO: 54 and SEQ ID NO: 65. Preferably, the VH of said immunobinder comprise the CDRs of the group consisting of SEQ ID NO: 7, SEQ ID NO: 19 and SEQ ID NO: 31 and/or the CDRs of the VL of said immunobinder comprise CDRs of the group consisting of SEQ ID NO: 42, SEQ ID NO: 54 and SEQ ID NO: 65.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 8, SEQ ID NO: 20, SEQ ID NO: 32, SEQ ID NO: 43, SEQ ID NO: 55 and SEQ ID NO: 66. Preferably, the VH of said immunobinder comprise the CDRs of the group consisting of SEQ ID NO: 8, SEQ ID NO: 20 and SEQ ID NO: 32 and/or the CDRs of the VL of said immunobinder comprise CDRs of the group consisting of SEQ ID NO: 43, SEQ ID NO: 55 and SEQ ID NO: 66.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 9, SEQ ID NO: 21, SEQ ID NO: 33, SEQ ID NO: 44, SEQ ID NO: 56 and SEQ ID NO: 67. Preferably, the VH of said immunobinder comprise the CDRs of the group consisting of SEQ ID NO: 9, SEQ ID NO: 21 and SEQ ID NO: 33 and/or the CDRs of the VL of said immunobinder comprise CDRs of the group consisting of SEQ ID NO: 44, SEQ ID NO: 56 and SEQ ID NO: 67.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 10, SEQ ID NO: 22, SEQ ID NO: 34, SEQ ID NO: 45, SEQ ID NO: 57 and SEQ ID NO: 68. Preferably, the VH of said immunobinder comprise the CDRs of the group consisting of SEQ ID NO: 10, SEQ ID NO: 22 and SEQ ID NO: 34 and/or the CDRs of the VL of said immunobinder comprise CDRs of the group consisting of SEQ ID NO: 45, SEQ ID NO: 57 and SEQ ID NO: 68

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 11, SEQ ID NO: 13, SEQ ID NO: 23, SEQ ID NO: 25, SEQ ID NO: 35, SEQ ID NO: 46, SEQ ID NO: 58 and SEQ ID NO: 69. Preferably, the VH of said immunobinder comprise the CDRs of the group consisting of SEQ ID NO: 11, SEQ ID NO: 23 and SEQ ID NO: 35 and/or the CDRs of the VL of said immunobinder comprise CDRs of the group consisting of SEQ ID NO: 46, SEQ ID NO: 58 and SEQ ID NO: 69. Alternatively, the VH of said immunobinder comprise the CDRs of the group consisting of SEQ ID NO: 13, SEQ ID NO: 25 and SEQ ID NO: 35 and/or the CDRs of the VL of said immunobinder comprise CDRs of the group consisting of SEQ ID NO: 46, SEQ ID NO: 58 and SEQ ID NO: 69.

In another embodiment, the invention provides an immunobinder comprising at least one CDR having at least 75% similarity, preferably at least 75% identity, more preferably at least 80%, 85%, 90% 95%, even more preferably 100% identity to a sequence of the group consisting of SEQ ID NO: 12, SEQ ID NO: 24, SEQ ID NO: 36, SEQ ID NO: 47, SEQ ID NO: 48, SEQ ID NO: 59, and SEQ ID NO: 70. Preferably, the VH of said immunobinder comprise the CDRs of the group consisting of SEQ ID NO: 12, SEQ ID NO: 24 and SEQ ID NO: 36. Additionally or alternatively, the VL of said immunobinder comprise CDRs of the group consisting of SEQ ID NO: 47, SEQ ID NO: 48, SEQ ID NO: 59, and SEQ ID NO: 70, e.g. SEQ ID NO: 47, SEQ ID NO: 59, and SEQ ID NO: 70; or SEQ ID NO: 48, SEQ ID NO: 59, and SEQ ID NO: 70.

In a much preferred embodiment, the immunobinder disclosed herein neutralizes human VEGF and is cross-reactive with rat/mouse VEGF or a portion thereof.

The immunobinder can comprise an antibody or any alternative binding scaffold capable of accommodating CDRs. The CDRs set forth in SEQ ID Nos: 2-72 can be grafted onto any suitable binding scaffold using any art recognized methods (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.). However, it is preferred that the immunobinders disclosed herein are humanized, and thus suitable for therapeutic applications.

In the case of antibodies, the rabbit CDRs set forth in SEQ ID Nos: 2-72 may be grafted into the framework regions of any antibody from any species. However, it has previously been discovered that antibodies or antibody derivatives comprising the frameworks identified in the so called "quality control" screen (WO0148017) are characterised by a generally high stability and/or solubility and thus may also be useful in the context of extracellular applications such as neutralizing human VEGF. Moreover, it has further been discovered that one particular combination of these VL (variable light chain) and VH (variable heavy chain) soluble and stable frameworks is particularly suited to accommodating rabbit CDRs. Accordingly, in one embodiment, the CDRs set forth in SEQ ID Nos: 2-72 are grafted into the human antibody frameworks derived by "quality control" screening disclosed in EP1479694. The amino acid sequences of exemplary frameworks for use in the invention are set forth in SEQ ID Nos: 172 to 174. It was surprisingly found that upon grafting into said framework or its derivatives, loop conformation of a large variety of rabbit CDRs could be fully maintained, largely independent of the sequence of the donor framework. Moreover, said framework or its derivatves containing different rabbit CDRs are well expressed and produced contrary to the rabbit wild type single chains and still almost fully retain the affinity of the original donor rabbit antibodies.

Thus, in a preferred embodiment, the CDRs and/or CDR motifs disclosed herein are present in a heavy chain variable region framework sequence having at least 80% sequence identity, more preferably at least 85%, 90% 95%, even more preferably 100% identity to the sequence of SEQ ID NO: 169. In a preferred embodiment, the heavy chain variable region framework sequence comprises SEQ ID NO: 170 or SEQ ID NO: 171.

In a preferred embodiment, the CDRs and/or CDR motifs disclosed herein are present in a light chain variable region framework sequence having at least 85% sequence identity, more preferably at least 90%, 95%, even more preferably 100% identity to the sequence of SEQ ID NO: 167, more preferably comprising SEQ ID NO: 167 or SEQ ID NO: 168.

In rabbit antibodies, CDRs can contain cysteine residues that become disulphide linked to cysteine residues in the antibody framework. Accordingly, it may be necessary, when grafting rabbit CDRs containing cysteine residues into non-rabbit framework regions to introduce cysteine residues in the non-rabbit framework by, for example, mutagenesis to facilitate the stabilization of rabbit CDR through a disulphide linkage.

In other embodiments, the invention provides an immunobinder, which specifically binds VEGF, comprising at least one of a VL or a VH amino acid sequence. Exemplary VL or VH amino acid sequences for use in the immunobinders of the invention are set forth in SEQ ID Nos: 72-106 and 107-166, respectively.

In a preferred embodiment, the invention provides an immunobinder comprising a VH having at least 80%, more preferably at least 85%, 90%, 95%, most preferably 100% identity to a sequence selected from the group consisting of SEQ ID NO: 107, SEQ ID NO: 108, SEQ ID NO: 118, SEQ ID NO: 119, SEQ ID NO: 130 and SEQ ID NO: 131 (VH 60-11-4, VH 60-11-6, VH 60-11-4min, VH 60-11-6min, VH 60-11-4max and VH 60-11-6max, respectively);

and/or a VL having at least 80%, more preferably at least 85%, 90%, 95%, most preferably 100% identity to a sequence selected from the group consisting of SEQ ID NO: 72, SEQ ID NO:82 and SEQ ID NO: 93 (VL 60, VL 60min, VL 60max, respectively).

In another preferred embodiment, the invention provides an immunobinder comprising a VH having at least 80%, more preferably at least 85%, 90%, 95%, most preferably 100% identity to a sequence selected from the group consisting of SEQ ID NO: 109, SEQ ID NO: 120 and SEQ ID NO: 132 (VH 435, VH 435min and VH 435max, respectively);

and/or a VL having at least 80%, more preferably at least 85%, 90%, 95%, most preferably 100% identity to a sequence selected from the group consisting of SEQ ID NO: 73, SEQ ID NO: 83 and SEQ ID NO:94 (VL 435, VL 435min and VL 435max, respectively).

Preferably, said immunobinder has at least 80%, more preferably at least 85%, 90%, 95%, most preferably 100% identity to SEQ ID NO: 175 (435max).

In another preferred embodiment, the invention provides an immunobinder comprising a VH having at least 80%, more preferably at least 85%, 90%, 95%, most preferably 100% identity to a sequence selected from the group consisting of SEQ ID NO: 110, SEQ ID NO: 121 and SEQ ID NO: 133 (VH 453, VH 453min and VH 453max, respectively);

and/or a VL having at least 80%, more preferably at least 85%, 90%, 95%, most preferably 100% identity to a sequence selected from the group consisting of SEQ ID NO: 74, SEQ ID NO:84 and SEQ ID NO: 95(VL 453, VL 453min and VL 453max, respectively).

In another preferred embodiment, the invention provides an immunobinder comprising a VH having at least 80%, more preferably at least 85%, 90%, 95%, most preferably 100% identity to a sequence selected from the group consisting of SEQ ID NO: 111, SEQ ID NO: 122 and SEQ ID NO: 134 (VH 375, VH 375min and VH 375max, respectively);

and/or a VL having at least 80%, more preferably at least 85%, 90%, 95%, most preferably 100% identity to a sequence selected from the group consisting of SEQ ID NO: 75, SEQ ID NO: 85 and SEQ ID NO:96 (VL 375, VL 375min and VL 375max, respectively).

In another preferred embodiment, the invention provides an immunobinder comprising a VH having at least 80%, more preferably at least 85%, 90%, 95%, most preferably 100% identity to a sequence selected from the group consisting of SEQ ID NO: 112, SEQ ID NO: 123 and 135 (VH 610, VH 610min and VH 610max, respectively);

and/or a VL having at least 80%, more preferably at least 85%, 90%, 95%, most preferably 100% identity to a sequence selected from the group consisting of SEQ ID NO: 76, SEQ ID NO: 86 and SEQ ID NO: 97 (VL 610, VL 610min and VL 610max, respectively).

In another preferred embodiment, the invention provides an immunobinder comprising a VH having at least 80%, more preferably at least 85%, 90%, 95%, most preferably 100% identity to a sequence selected from the group consisting of SEQ ID NO: 113, SEQ ID NO: 124, SEQ ID NO: 129, SEQ ID NO: 136, SEQ ID NO: 142, SEQ ID NO: 144, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO:154, SEQ ID NO: 155, SEQ ID NO: 156, SEQ ID NO:157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165 and SEQ ID NO: 166 (VH 578 and variants thereof);

and/or a VL having at least 80%, more preferably at least 85%, 90%, 95%, most preferably 100% identity to a sequence selected from the group consisting of SEQ ID NO: 77, SEQ ID NO: 87, SEQ ID NO: 92, SEQ ID NO: 98, SEQ ID NO: 103, SEQ ID NO: 104 and SEQ ID NO: 105 (VL 578 and variants thereof).

Preferably, said immunobinder has at least 80%, more preferably at least 85%, 90%, 95%, most preferably 100% identity to SEQ ID NO: 178 (578min), SEQ ID NO: 179 (578max) or SEQ ID NO: 180 (578minmax).

In another preferred embodiment, the invention provides an immunobinder comprising a VH having at least 80%, more preferably at least 85%, 90%, 95%, most preferably 100% identity to a sequence selected from the group consisting of SEQ ID NO: 114, SEQ ID NO: 125 and SEQ ID NO: 137 (VH 534, VH 534min and VH 534max, respectively);

and/or a VL having at least 80%, more preferably at least 85%, 90%, 95%, most preferably 100% identity to a sequence selected from the group consisting of SEQ ID NO: 78, SEQ ID NO: 88 and SEQ ID NO: 99 (VL 534, VL 534min and VL 534max, respectively).

In another preferred embodiment, the invention provides an immunobinder comprising a VH having at least 80%, more preferably at least 85%, 90%, 95%, most preferably 100% identity to a sequence selected from the group consisting of SEQ ID NO: 115, SEQ ID NO: 126, SEQ ID NO:138 and SEQ ID NO: 143 (VH 567, VH 567min and VH 567max, respectively);

and/or a VL having at least 80%, more preferably at least 85%, 90%, 95%, most preferably 100% identity to a sequence selected from the group consisting of SEQ ID NO: 79, SEQ ID NO:89 and SEQ ID NO: 100 (VL 567, VL 567min and VL 567max, respectively).

Preferably, said immunobinder has at least 80%, more preferably at least 85%, 90%, 95%, most preferably 100% identity to SEQ ID NO: 177 (567min).

In another preferred embodiment, the invention provides an immunobinder comprising a VH having at least 80%, more preferably at least 85%, 90%, 95%, most preferably 100% identity to a sequence selected from the group consisting of SEQ ID NO: 116, SEQ ID NO: 127, SEQ ID NO:139 and SEQ ID NO: 140 (VH 509, VH 509min, VH 509max and VH 509maxII, respectively);

and/or a VL having at least 80%, more preferably at least 85%, 90%, 95%, most preferably 100% identity to a sequence selected from the group consisting of SEQ ID NO: 80, SEQ ID NO: 90 and SEQ ID NO: 101 (VL 509, VL 509min and VL 509max, respectively).

In another preferred embodiment, the invention provides an immunobinder comprising a VH having at least 80%, more preferably at least 85%, 90%, 95%, most preferably 100% identity to a sequence selected from the group consisting of SEQ ID NO: 117, SEQ ID NO: 128, SEQ ID NO: 141 and SEQ ID NO: 145 (VH 511, VH 511min, VH 511max and VH 511maxDHP, respectively);

and/or a VL having at least 80%, more preferably at least 85%, 90%, 95%, most preferably 100% identity to a sequence selected from the group consisting of SEQ ID NO: 81, SEQ ID NO: 91, SEQ ID NO: 102 and SEQ ID NO: 106 (VL 511, VL 511min, VL 511max and VL 511minC41L, respectively).

Preferably, said immunobinder has at least 80%, more preferably at least 85%, 90%, 95%, most preferably 100% identity to SEQ ID NO: 176 (511_max).

In certain embodiments, the invention further provides an immunobinder, which specifically binds VEGF, comprising an amino acid sequence with substantial similarity to an amino acid sequence set forth in SEQ ID Nos: 2-166 and in SEQ ID Nos: 175-180, and wherein the immunobinder essentially retains or improves the desired functional properties of the anti-VEGF immunobinder of the invention. Preferred percentage similarities include, but are not limited to, at least 50%, 60%, 70%, 75%, 80%, 85%, 90% or 95% identity.

In certain embodiments, the invention further provides an immunobinder, which specifically binds VEGF, comprising an amino acid sequence with substantial identity to an amino acid sequence set forth in SEQ ID Nos: 2-166 and in SEQ ID Nos. 175-180, and wherein the immunobinder retains or improves the desired functional properties of the anti-VEGF immunobinder of the invention. Preferred percentage identities include, but are not limited to, at least 50%, 60%, 70%, 75%, 80%, 85%, 90% or 95% identity.

In certain embodiments, the invention further provides an immunobinder, which specifically binds VEGF, comprising an amino acid sequence with conservative substitutions relative to an amino acid sequence set forth in SEQ ID Nos: 2-166 and in SEQ ID Nos. 175-180, and wherein the immunobinder retains or improves the desired functional properties of the anti-VEGF immunobinder of the invention.

In some embodiments, the invention provides immunobinders that bind specifically to human VEGF and cross react with VEGF molecules of other species, for example, mouse VEGF, rat VEGF, rabbit VEGF or guinea pig VEGF. In a particular embodiment the anti-VEGF immunobinder can bind specifically to human and rat/mouse VEGF.

In some embodiments, the invention provides immunobinders that bind specifically to human VEGF and do not cross react with VEGF molecules of other species, for example, mouse VEGF, rat VEGF, rabbit VEGF or guinea pig VEGF.

In some embodiments, the invention provides immunobinders that bind specifically to human VEGF and wherein the immunobinders are affinity matured.

In one embodiment, antibodies and antibody fragments of the present invention are single chain antibodies (scFv) or Fab fragments. In the case of scFv antibodies, a selected VL domain can be linked to a selected VH domain in either orientation by a flexible linker. A suitable state of the art linker consists of repeated GGGGS (SEQ ID NO: 182) amino acid sequences or variants thereof. In a preferred embodiment of the present invention a $(GGGGS)_4$ linker of the amino acid sequence set forth in SEQ ID NO: 181, but variants of 1-3 repeats are also possible (Holliger et al. (1993), Proc. Natl. Acad. Sci. USA 90:6444-6448). Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. Immunother. 50:51-59. The arrangement can be either VL-linker-VH or VH-linker-VL, with the former orientation being the preferred one. However, single VH or VL domain antibodies are also contemplated. In the case of Fab fragments, selected light chain variable domains VL are fused to the constant region of a human Ig kappa chain, while the suitable heavy chain variable domains VH are fused to the first (N-terminal) constant domain CH1 of a human IgG. At the C-terminus of the constant domain or at other sites of the variable or constant domain, an inter-chain disulfide bridge may be formed. Alternatively, the two chains may also be linked by a flexible linker resulting in a single chain Fab antibody.

The antibodies or antibody derivatives of the present invention can have affinities to human VEGF with dissociation constants $K_d$ in a range of $10^{-14}$M to $10^{-5}$M. In a preferred embodiment of the present invention the $K_d$ is ≤1 nM. The affinity of an antibody for an antigen can be determined experimentally using a suitable method (Berzofsky et al. "Antibody-Antigen Interactions", in *Fundamental Immunology*, Paul, W. E., Ed, Raven Press: New York, N.Y. (1992); Kuby, J. *Immunology*, W. H. Freeman and Company: New York, N.Y.) and methods described therein.

The company Epitomics sells an anti-VEGF antibody which is a rabbit monoclonal antibody (VEGF (C-term) Rabbit Antibody, Cat.no. 1909-1). Said antibody is directed against residues on the C-terminus of human VEGF and therefore not able to neutralize VEGF. Hence, said antibody is not suitable for therapeutic applications. Moreover, said monoclonal IgG is not a humanized antibody but is a natural rabbit full-length immunoglobulin. In addition, it was shown that this antibody does not recognize the native form of VEGF.

Immunobinders that Bind the Same Epitopes on VEGF

In another aspect, the invention provides antibodies that bind to an epitope on VEGF recognized by an antibody comprising any one of the amino acid sequences set forth in SEQ ID No 2-211. Such antibodies can be identified based upon their ability to cross-compete with an antibody comprising any one or more of the amino acid sequences set forth in SEQ ID No 2-211 in standard VEGF-binding assays including, but not limited, to ELISA. The ability of a test antibody to inhibit the binding to human VEGF of an antibody comprising any one or more of the amino acid sequences set forth in SEQ ID No 2-211 demonstrates that the test antibody can cross-compete thus interact with an overlapping epitope on human VEGF as an antibody comprising any one or more of the amino acid sequences set forth in SEQ ID No 2-211.

Additionally or alternatively, such antibodies can be also identified using standard epitope mapping techniques to determine if they bind to the same peptide immunogens. Structural modeling techniques may also be employed to further define the precise molecular determinants to the antibody/VEGF interaction, including, but not limited to, NMR, X-ray crystallography, computer based modeling, or protein tomography (Banyay et al., 2004 ASSAY and Drug Development Technologies (2), 5, Page 516-567). Indeed, the crystal structure of VEGF has been solved and the surface amino acid residues involved in VEGFr binding are known (Fuh, et al., 2006, J. Biol. Chem., 281, 6625-6631). Accordingly, given the amino acid sequence of the peptide immunogen and the structural knowledge of VEGF available in the art, it is well within the skill in art to identify antibodies that bind to an epitope on VEGF recognized by the antibodies comprising any one or more of the amino acid sequences set forth in SEQ ID No 2-211.

In some embodiments, antibodies that bind to an epitope on VEGF recognized by an antibody comprising any one or more of the amino acid sequences set forth in SEQ ID No 2-211 bind to VEGF with an affinity of at least $10^7$ $M^{-1}$, for example, at least $10^7 M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$ or at least $10^{13}$ $M^{-1}$.

In some embodiments, antibodies that bind to an epitope on VEGF recognized by an antibody comprising any one or more of the amino acid sequences set forth in SEQ ID No 2-211 bind specifically to human VEGF and do not cross react with VEGF molecules of other species, for example, mouse VEGF, rat VEGF, rabbit VEGF, or guinea pig VEGF.

In some embodiments, antibodies that bind to an epitope on VEGF recognized by an antibody comprising any one or more of the amino acid sequences set forth in SEQ ID No 2-211 cross react with VEGF molecules of other species, for example, mouse VEGF, rat VEGF, or rabbit VEGF.

Optimized Variants

The antibodies of the invention may be further optimized for enhanced functional properties, e.g., for enhanced solubility and/or stability.

In certain embodiments, the antibodies of the invention are optimized according to the "functional consensus" methodology disclosed in PCT Application Serial No. PCT/EP2008/001958, entitled "Sequence Based Engineering and Optimization of Single Chain Antibodies", filed on Mar. 12, 2008, which is incorporated herein by reference. For example, the VEGF immunobinders of the invention can be compared with a database of functionally-selected scFvs to identify amino acid residue positions that are either more or less tolerant of variability than the corresponding position(s) in the VEGF immunobinder, thereby indicating that such identified residue position(s) may be suitable for engineering to improve functionality such as stability and/or solubility.

Exemplary framework positions for substitution are described in PCT Application No. PCT/CH2008/000285, entitled "Methods of Modifying Antibodies, and Modified Antibodies with Improved Functional Properties", filed on Jun. 25, 2008, and PCT Application No. PCT/CH2008/000284, entitled "Sequence Based Engineering and Optimization of Single Chain Antibodies", filed on Jun. 25, 2008. For example, one or more of the following substitutions may be introduced at an amino acid position (AHo numbering is referenced for each of the amino acid position listed below) in the heavy chain variable region of an immunobinder of the invention:

(a) Q or E at amino acid position 1;
(b) Q or E at amino acid position 6;
(c) T, S or A at amino acid position 7, more preferably T or A, even more preferably T;
(d) A, T, P, V or D, more preferably T, P, V or D, at amino acid position 10,
(e) L or V, more preferably L, at amino acid position 12,
(f) V, R, Q, M or K, more preferably V, R, Q or M at amino acid position 13;
(g) R, M, E, Q or K, more preferably R, M, E or Q, even more preferably R or E, at amino acid position 14;
(h) L or V, more preferably L, at amino acid position 19;
(i) R, T, K or N, more preferably R, T or N, even more preferably N, at amino acid position 20;
(j) I, F, L or V, more preferably I, F or L, even more preferably I or L, at amino acid position 21;
(k) R or K, more preferably K, at amino acid position 45;
(l) T, P, V, A or R, more preferably T, P, V or R, even more preferably R, at amino acid position 47;
(m) K, Q, H or E, more preferably K, H or E, even more preferably K, at amino acid position 50;
(n) M or I, more preferably I, at amino acid position 55;
(o) K or R, more preferably K, at amino acid position 77;
(p) A, V, L or I, more preferably A, L or I, even more preferably A, at amino acid position 78;
(q) E, R, T or A, more preferably E, T or A, even more preferably E, at amino acid position 82;
(r) T, S, I or L, more preferably T, S or L, even more preferably T, at amino acid position 86;
(s) D, S, N or G, more preferably D, N or G, even more preferably N, at amino acid position 87;
(t) A, V, L or F, more preferably A, V or F, even more preferably V, at amino acid position 89;
(u) F, S, H, D or Y, more preferably F, S, H or D, at amino acid position 90;
(v) D, Q or E, more preferably D or Q, even more preferably D, at amino acid position 92;
(w) G, N, T or S, more preferably G, N or T, even more preferably G, at amino acid position 95;
(x) T, A, P, F or S, more preferably T, A, P or F, even more preferably F, at amino acid position 98;
(y) R, Q, V, I, M, F, or L, more preferably R, Q, I, M, F or L, even more preferably Y, even more preferably L, at amino acid position 103; and
(z) N, S or A, more preferably N or S, even more preferably N, at amino acid position 107.

Additionally or alternatively, one or more of the following substitutions can be introduced into the light chain variable region of an immunobinder of the invention:

(aa) Q, D, L, E, S, or I, more preferably L, E, S or I, even more preferably L or E, at amino acid position 1;
(bb) S, A, Y, I, P or T, more preferably A, Y, I, P or T, even more preferably P or T at amino acid position 2;
(cc) Q, V, T or I, more preferably V, T or I, even more preferably V or T, at amino acid position 3;
(dd) V, L, I or M, more preferably V or L, at amino acid position 4;
(ee) S, E or P, more preferably S or E, even more preferably S, at amino acid position 7;
(ff) T or I, more preferably I, at amino acid position 10;
(gg) A or V, more preferably A, at amino acid position 11;
(hh) S or Y, more preferably Y, at amino acid position 12;
(ii) T, S or A, more preferably T or S, even more preferably T, at amino acid position 14;
(jj) S or R, more preferably S, at amino acid position 18;
(kk) T or R, more preferably R, at amino acid position 20;
(ll) R or Q, more preferably Q, at amino acid position 24;
(mm) H or Q, more preferably H, at amino acid position 46;
(nn) K, R or I, more preferably R or I, even more preferably R, at amino acid position 47;
(oo) R, Q, K, E, T, or M, more preferably Q, K, E, T or M, at amino acid position 50;
(pp) K, T, S, N, Q or P, more preferably T, S, N, Q or P, at amino acid position 53;
(qq) I or M, more preferably M, at amino acid position 56;
(rr) H, S, F or Y, more preferably H, S or F, at amino acid position 57;
(ss) I, V or T, more preferably V or T, R, even more preferably T, at amino acid position 74;
(tt) R, Q or K, more preferably R or Q, even more preferably R, at amino acid position 82;
(uu) L or F, more preferably F, at amino acid position 91;
(vv) G, D, T or A, more preferably G, D or T, even more preferably T, at amino acid position 92;
(xx) S or N, more preferably N, at amino acid position 94;
(yy) F, Y or S, more preferably Y or S, even more preferably S, at amino acid position 101; and
(zz) D, F, H, E, L, A, T, V, S, G or I, more preferably H, E, L, A, T ,V, S, G or I, even more preferably A or V, at amino acid position 103.

The AHo numbering system is described further in Honegger, A. and Pluckthun, A. (2001) *J. Mol. Biol.* 309: 657-670). Alternatively, the Kabat numbering system as described further in Kabat et al. (Kabat, E. A., et al. (1991) Sequences of Proteins of Immunological Interest, Fifth Edition, U.S. Department of Health and Human Services, NIH Publication No. 91-3242) may be used. Conversion tables for the two different numbering systems used to identify amino acid residue positions in antibody heavy and light chain variable regions are provided in A. Honegger, J.Mol.Biol. 309 (2001) 657-670.

In other embodiments, the immunobinders of the invention comprise one or more of the solubility and/or stability enhancing mutations described in U.S. Provisional Application Ser. No. 61/075,692, entitled "Solubility Optimization of Immunobinders," filed on Jun. 25, 2008. In certain preferred embodiments, the immunobinder comprises a solubility enhancing mutation at an amino acid position selected from the group of heavy chain amino acid positions consisting of 12, 103 and 144 (AHo Numbering convention). In one preferred embodiment, the immunobinder comprises one or more substitutions selected from the group consisting of: (a) Serine (S) at heavy chain amino acid position 12; (b) Serine (S) or Threonine (T) at heavy chain amino acid position 103; and (c) Serine (S) or Threonine (T) at heavy chain amino acid position 144. In another embodiment, the immunobinder comprises the following substitutions: (a) Serine (S) at heavy chain amino acid position 12; (b) Serine (S) or Threonine (T) at heavy chain amino acid position 103; and (c) Serine (S) or Threonine (T) at heavy chain amino acid position 144.

Hybridomas Expressing Rabbit Anti-VEGF Antibodies

In another aspect, the invention provides a hybridoma expressing a monoclonal antibody comprising any one or more of the amino acid sequences set forth in SEQ ID Nos 72-81. Methods for generating hybridomas from Rabbit B-cells are well known in the art and are disclosed, for example, in U.S. patent application 2005/0033031.

Production of Anti-VEGF Immunobinders

The antibodies or antibody derivatives of the present invention may be generated using routine techniques in the field of recombinant genetics. Knowing the sequences of the polypeptides, the cDNAs encoding them can be generated by gene synthesis. These cDNAs can be cloned into suitable vector plasmids. Once the DNA encoding a VL and/or a VH domain are obtained, site directed mutagenesis, for example by PCR using mutagenic primers, can be performed to obtain various derivatives. The best "starting" sequence can be chosen depending on the number of alterations desired in the VL and/or VH sequences.

Methods for incorporating or grafting CDRs into framework regions include those set forth in, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al, as well as those disclosed in U.S. Provisional Application Ser. No. 61/075,697, entitled "Humanization of Rabbit Antibodies Using Universal Antibody Frameworks," filed on Jun. 25, 2008.

Standard cloning and mutagenesis techniques well known to the person skilled in the art can be used to attach linkers, shuffle domains or construct fusions for the production of Fab fragments. Basic protocols disclosing the general methods of this invention are described in *Molecular Cloning, A Laboratory Manual* (Sambrook & Russell, 3$^{rd}$ ed. 2001) and in *Current Protocols in Molecular Biology* (Ausubel et al., 1999).

The DNA sequence harboring a gene encoding a scFv polypeptide, or in the case of Fab fragments, encoding either two separate genes or a bi-cistronic operon comprising the two genes for the VL-Cκ and the VH-CH1 fusions are cloned in a suitable expression vector, preferably one with an inducible promoter. Care must be taken that in front of each gene an appropriate ribosome binding site is present that ensures translation. It is to be understood that the antibodies of the present invention comprise the disclosed sequences rather than they consist of them. For example, cloning strategies may require that a construct is made from which an antibody with one or a few additional residues at the N-terminal end are present. Specifically, the methionine derived from the start codon may be present in the final protein in cases where it has not been cleaved posttranslationally. Most of the constructs for scFv antibodies give rise to an additional alanine at the N-terminal end. In a preferred embodiment of the present invention, an expression vector for periplasmic expression in *E. coli* is chosen (Krebber, 1997). Said vector comprises a promoter in front of a cleavable signal sequence. The coding sequence for the antibody peptide is then fused in frame to the cleavable signal sequence. This allows the targeting of the expressed polypeptide to the bacterial periplasm where the signal sequence is cleaved. The antibody is then folded. In the case of the Fab fragments, both the VL-Cκ and the VH—CH1 fusions peptides must be linked to an export signal. The covalent S—S bond is formed at the C-terminal cysteines after the peptides have reached the periplasm. If cytoplasmic expression of antibodies is preferred, said antibodies usually can be obtained at high yields from inclusion bodies, which can be easily separated from other cellular fragments and protein. In this case the inclusion bodies are solubilized in a denaturing agent such as, e.g., guanidine hydrochloride (GndHCl) and then refolded by renaturation procedures well known to those skilled in the art.

Plasmids expressing the scFv or Fab polypeptides are introduced into a suitable host, preferably a bacterial, yeast or mammalian cell, most preferably a suitable E. coli strain as for example JM83 for periplasmic expression or BL21 for expression in inclusion bodies. The polypeptide can be harvested either from the periplasm or form inclusion bodies and purified using standard techniques such as ion exchange chromatography, reversed phase chromatography, affinity chromatography and/or gel filtration known to the person skilled in the art.

The antibodies or antibody derivatives of the present invention can be characterized with respect to yield, solubility and stability in vitro. Binding capacities towards VEGF, preferably towards human VEGF, can be tested in vitro by ELISA or surface plasmon resonance (BIACore), using recombinant human VEGF as described in WO9729131, the latter method also allowing to determine the $k_{off}$ rate constant, which should preferably be less than $10^{-3}s^{-1}$. $K_d$ values of ≤10 nM are preferred.

Aside from antibodies with strong binding affinity for human VEGF, it is also desirable to select anti-VEGF antibodies which have other beneficial properties from a therapeutic perspective. For example, the antibody may be one which inhibits HUVEC cell growth in response to VEGF (see Example 3). In one embodiment, the antibody may be able to inhibit HUVEC cell proliferation in response to a near maximally effective concentration of VEGF (0.08 nM). Preferably, the antibody has an effective dose 50 (ED50) value of no more than about 5 nM, preferably no more than about 1 nM, preferably no more than about 1 nM, preferably no more than about 0.5 nM and most preferably no more than about 0.06 nM, for inhibiting VEGF-induced proliferation of endothelial cells in this "endothelial cell growth assay", i.e., at these concentrations the antibody is able to inhibit VEGF-induced endothelial cell growth in vitro by, e.g., 50% or more.

Bispecific Molecules

In another aspect, the present invention features bispecific molecules comprising an anti-VEGF antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, tumor specific or pathogen specific antigens, peptide or binding mimetic, such that a bispecific molecule results. Accordingly, the present invention includes bispecific molecules comprising at least one first binding molecule having specificity for VEGF and a second binding molecule having specificity for one or more additional target epitope.

In one embodiment, the bispecific molecules of the invention comprise a binding specificity at least one antibody, or an antibody fragment thereof, including, e.g., an Fab, Fab', F(ab')₂, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-l-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding, for example, via the C-terminus hinge regions of the two heavy chains or other sites, whether naturally occurring or introduced artificially. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')₂ or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Further, a bispecfic molecule may be a scFv that specifically binds to first target, wherein the VH and VL of said scFv are linked with a flexible linker comprising a domain providing specific binding to a second target. Suitable linkers are described in U.S. Provisional Application No. 60/937,820. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or by immunoblot assay. Each of these assays generally detects the presence of protein-antibody complexes of particular interest by employing a labeled reagent (e.g., an antibody) specific for the complex of interest. For example, the VEGF-antibody complexes can be detected using e.g., an enzyme-linked antibody or antibody fragment which recognizes and specifically binds to the antibody-VEGF complexes. Alternatively, the complexes can be detected using any of a variety of other immunoassays. For example, the antibody can be radioactively labeled and used in a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Immunoconjugates

In another aspect, the present invention features an anti-VEGF antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for being used diagnostically or therapeutically include, but are not limited to, iodine$^{131}$, indium$^{111}$, yttrium$^{90}$ and lutetium$^{177}$. Methods for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies'84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

Uses of Anti-VEGF Antibodies

For therapeutic applications, the anti-VEGF antibodies of the invention are administered to a mammal, preferably a human, in a pharmaceutically acceptable dosage form such as those discussed herein, including those that may be administered to a human intravenously, as a bolus or by continuous infusion over a period of time, by topical, intraocular, intramuscular, intraperitoneal, intra-cerebrospinal, subcutaneous, intra-articular, intrasynovial, intrathecal, oral, or inhalation routes. The antibodies also are suitably administered by intra tumoral, peritumoral, intralesional, or perilesional routes, to exert local as well as systemic therapeutic effects. The intraperitoneal route is expected to be particularly useful, for example, in the treatment of ovarian tumors.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

The anti-VEGF antibodies are useful in the treatment of VEGF-mediated diseases as described herein. For example, age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VEGF antibodies of the present invention are especially useful in reducing the severity of AMD. The progress of this therapy is easily monitored by conventional techniques including opthalmoscopy, ocular fundus microscopy, and ocular computer tomography.

All FDA approved doses and regimes suitable for use with Lucentis are considered. Other doses and regimes are described in U.S. Provisional Application Ser. No. 61/075,641, entitled "Improved Immunobinder Formulations And Methods For Adminstration", filed Jun. 25, 2008, and U.S. Provisional Application No. 61/058,504, which are expressly incorporated herein.

According to another embodiment of the invention, the effectiveness of the antibody in preventing or treating disease may be improved by administering the antibody serially or in combination with another agent that is effective for those purposes, such as tumor necrosis factor (TNF), an antibody capable of inhibiting or neutralizing the angiogenic activity of acidic or basic fibroblast growth factor (FGF) or hepatocyte growth factor (HGF), an antibody capable of inhibiting or neutralizing the coagulant activities of tissue factor, protein C, or protein S (see Esmon et al., PCT Patent Publication No. WO 91/01753, published 21 Feb. 1991), an antibody capable of binding to HER2 receptor (see Hudziak et al., PCT Patent Publication No. WO 89/06692, published 27 Jul. 1989), or one or more conventional therapeutic agents such as, for example, alkylating agents, photocoagulants (such as verteporfin), folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Also, the antibody is suitably administered serially or in combination with radiological treatments, whether involving irradiation or administration of radioactive substances.

The antibodies of the invention may be used as affinity purification agents. In this process, the antibodies are immobilized on a solid phase such a Sephadex resin or filter paper, using methods well known in the art. The immobilized antibody is contacted with a sample containing the VEGF protein (or fragment thereof) to be purified, and thereafter the support is washed with a suitable solvent that will remove substantially all the material in the sample except the VEGF protein, which is bound to the immobilized antibody. Finally, the support is washed with another suitable solvent, such as glycine buffer, pH 5.0, that will release the VEGF protein from the antibody.

Anti-VEGF antibodies may also be useful in diagnostic assays for VEGF protein, e.g., detecting its expression in specific cells, tissues, or serum. Such diagnostic methods may be useful in cancer diagnosis.

For diagnostic applications, the antibody typically will be labeled with a detectable moiety. Numerous labels are available which can be generally grouped into the following categories:

(a) Radioisotopes, such as $^{111}$In, $^{99}$Tc, $^{14}$C, $^{131}$I, $^{125}$I, $^{3}$H, $^{32}$P or $^{35}$S. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981). Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) .beta.-D-galactosidase (.beta.-D-Gal) with a chromogenic substrate (e.g., P-nitrophenyl-.beta.-D-galactosidase) or fluorogenic substrate 4-methylumbelliferyl-.beta.-D-galactosidase.

In another embodiment of the invention, the anti-VEGF antibody need not be labeled, and the presence thereof can be detected using a labeled antibody which binds to the VEGF antibody.

The antibodies of the present invention may be employed in any known assay method, such as competitive binding assays, direct and indirect sandwich assays, and immunoprecipitation assays. Zola, Monoclonal Antibodies: A Manual of Techniques, pp.147-158 (CRC Press, Inc. 1987).

Competitive binding assays rely on the ability of a labeled standard to compete with the test sample analyte for binding with a limited amount of antibody. The amount of VEGF protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

The antibody of the present invention can be provided in a kit, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Pharmaceutical Preparations

In one aspect the invention provides pharmaceutical formulations comprising anti-VEGF antibodies for the treatment of VEGF-mediated diseases. The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the antibody or antibody derivative therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 week and/or stable at about 2-8° C. for at least 3 months to 2 years. Furthermore, the formulation is preferably stable following freezing (to, e.g., -70° C.) and thawing of the formulation.

An antibody or antibody derivative "retains its physical stability" in a pharmaceutical formulation if it meets the defined release specifications for aggregation, degradation, precipitation and/or denaturation upon visual examination of color and/or clarity, or as measured by UV light scattering or by size exclusion chromatography, or other suitable art recognized methods.

An antibody or antibody derivative "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody or antibody derivative "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. -20° C.) such that it destabilizes the antibody in the formulation. Non-reducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 8.0; preferably from about 5.5 to about 7. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody or antibody derivative refers to an amount effective in the prevention or treatment of a disorder for the treatment of which the antibody or antibody derivative is effective. A "disease/disorder" is any condition that would benefit from treatment with the antibody or antibody derivative. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The present invention also provides pharmaceutical compositions comprising one or more antibodies or antibody derivative compounds, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an antibody or antibody derivative prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, intraocular, oral, nasal, rectal or parenteral administration. In certain embodiments, compositions in a form suitable for topical use, for example, as eye drops, are preferred. Other forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

The pharmaceutical composition may be prepared as a sterile injectable aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of an antibody or antibody derivative contained within a sustained release formulation depends upon, for example, the site of implantation, the rate and expected duration of release and the nature of the disease/disorder to be treated or prevented.

Antibody or antibody derivatives provided herein are generally administered in an amount that achieves a concentration in a body fluid (e.g., blood, plasma, serum, CSF, synovial fluid, lymph, cellular interstitial fluid, tears or urine) that is sufficient to detectably bind to VEGF and prevent or inhibit VEGF-mediated diseases/disorders. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5-20 fold higher than intravenous doses. The amount of antibody or antibody derivative that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to an antibody or antibody derivative directed to VEGF. Packaged pharmaceutical compositions may include a container holding a effective amount of at least one antibody or antibody derivative as described herein and instructions (e.g., labeling) indicating that the contained composition is to be used for treating a disease/disorder responsive to one antibody or antibody derivative following administration in the patient.

The antibodies or antibody derivatives of the present invention can also be chemically modified. Preferred modifying groups are polymers, for example an optionally substituted straight or branched chain polyalkene, polyalkenylene, or polyoxyalkylene polymer or a branched or unbranched polysaccharide. Such effector group may increase the half-live of the antibody in vivo. Particular examples of synthetic polymers include optionally substituted straight or branched chain poly(ethyleneglycol) (PEG), poly(propyleneglycol), poly(vinylalcohol) or derivatives thereof. Particular naturally occurring polymers include lactose, amylose, dextran, glycogen or derivatives thereof. The size of the polymer may be varied as desired, but will generally be in an average molecular weight range from 500 Da to 50000 Da. For local application where the antibody is designed to penetrate tissue, a preferred molecular weight of the polymer is around 5000 Da. The polymer molecule can be attached to the antibody, in particular to the C-terminal end of the Fab fragment heavy chain via a covalently linked hinge peptide as described in WO0194585. Regarding the attachment of PEG moieties, reference is made to "Poly (ethyleneglycol) Chemistry, Biotechnological and Biomedical Applications", 1992, J. Milton Harris (ed), Plenum Press, New York and "Bioconjugation Protein Coupling Techniques for the Biomedical Sciences", 1998, M. Aslam and A. Dent, Grove Publishers, New York.

After preparation of the antibody or antibody derivative of interest as described above, the pharmaceutical formulation comprising it is prepared. The antibody to be formulated has not been subjected to prior lyophilization and the formulation of interest herein is an aqueous formulation. Preferably the antibody or antibody derivative in the formulation is an antibody fragment, such as an scFv. The therapeutically effective amount of antibody present in the formulation is determined by taking into account the desired dose volumes and mode(s) of administration, for example. From about 0.1 mg/ml to about 50 mg/ml, preferably from about 0.5 mg/ml to about 40 mg/ml and most preferably from about 10 mg/ml to about 20 mg/ml is an exemplary antibody concentration in the formulation.

An aqueous formulation is prepared comprising the antibody or antibody derivative in a pH-buffered solution The buffer of this invention has a pH in the range from about 4.5 to about 8.0, preferably from about 5.5 to about 7. Examples of buffers that will control the pH within this range include acetate (e.g. sodium acetate), succinate (such as sodium succinate), gluconate, histidine, citrate and other organic acid buffers. The buffer concentration can be from about 1 mM to about 50 mM, preferably from about 5 mM to about 30 mM, depending, for example, on the buffer and the desired isotonicity of the formulation.

A polyol, which acts as a tonicifier and may stabilize the antibody, is included in the formulation. In preferred embodiments, the formulation does not contain a tonicifying amount of a salt such as sodium chloride, as this may cause the antibody or antibody derivative to precipitate and/or may result in oxidation at low pH. In preferred embodiments, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% whv, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to the antibody or antibody derivative formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, the formulation contains the above-identified agents (i.e. antibody or antibody derivative, buffer, polyol and surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are non-toxic to recipients at the dosages and concentrations employed and include: additional buffering agents, co-solvents, antioxidants including ascorbic acid and methionine, chelating agents such as EDTA, metal complexes (e.g. Zn-protein complexes), biodegradable polymers such as polyesters, and/or salt-forming counterions such as sodium.

The formulations to be used for in vivo administration must be sterile. This is readily accomplished by filtration through sterile filtration membranes, prior to, or following, preparation of the formulation.

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In preferred embodiments, the formulation is administered to the mammal by topical application of eye drops to the ocular surface. For such purposes, the formulation may applied using an eye drop applicator, for example.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody or antibody derivative is suitably administered to the patent at one time or over a series of treatments and may be administered to the patent at any time from diagnosis onwards. The antibody or antibody derivative may be administered as the sole treatment or in conjunction with other drugs or therapies useful in treating the condition in question.

As a general proposition, the therapeutically effective amount of the antibody or antibody derivative administered will be in the range of about 0.1 to about 50 mg/kg of patent body weight whether by one or more administrations, with the typical range of antibody used being about 0.3 to about 20 mg/kg, more preferably about 0.3 to about 15 mg/kg, administered daily, for example. However, other dosage regimens may be useful. The progress of this therapy is easily monitored by conventional techniques.

FDA approved doeses and regimes suitable for use with Lucentis are considered.

Other doses and regimes are described in U.S. Provisional Application Ser. No. 61/075,641, entitled "Improved Immunobinder Formulations And Methods For Adminstration", filed Jun. 25, 2008, which is expressly incorporated herein.

Articles of Manufacture

In another embodiment of the invention, an article of manufacture is provided comprising a container which holds the aqueous pharmaceutical formulation of the present invention and optionally provides instructions for its use. Suitable containers include, for example, bottles, vials, eye drop applicators and syringes. The container may be formed from a variety of materials such as glass or plastic. An exemplary container is a 3-20 cc single use glass or plastic vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

Exemplification

The present disclosure is further illustrated by the following examples, which should not be construed as further limiting. The contents of all figures and all references, patents and published patent applications cited throughout this application are expressly incorporated herein by reference in their entireties.

Throughout the examples, the following materials and methods were used unless otherwise stated.

General Materials and Methods

In general, the practice of the present invention employs, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Thermostability Measurements

Attenuated total reflectance Fourier transform IR (FTIR-ATR) spectra were obtained for various single chains and derivative molecules using the FT-IR Bio-ATR cell in a Tensor Bruker. The molecules were concentrated up to 3 mg/ml and dialyzed overnight at 4° C. against PBS, pH 6.5 and the buffer flow through was collected as blank. The denaturation profiles were obtained by thermo challenging the molecules with a broad range of temperatures in 5° C. steps (25 to 95° C.). All spectra manipulations were performed using OPUS software. The main buffer and transient atmospheric ($CO_2$ and $H_2O$) background were substracted from the protein spectrum. The resulting protein spectrum was then baseline corrected and the protein amide I spectra was determined from the width of the widest resolvable peak in the expected region. Second derivative spectra were obtained for the amide I band spectra using a third degree polynomial function with a smoothing function. Changes in protein structure were estimated by amide I second derivative analysis using a linear calibration curve for the initial curve-fit calculations assuming 0% denaturation for the 3 lower measurements and 100% denaturation for the 3 higher measurements. The denaturation profiles were used to approximate midpoints of the thermal unfolding transitions (TM) for every variant applying the Boltzmann sigmoidal model.

Solubility Measurements

Relative solubility of various scFv molecules was measured after enhancing protein aggregation and precipitation in presence of ammonium sulfate. Ammonium sulfate was added to the protein in aqueous solutions to yield increments of 5% of saturation in the final mixture salt-protein. The precipitation in the dynamic range was determined empirically and the saturation intervals reduced in this range to 2.5% intervals saturation in the final mixture. After ammonium sulfate addition, samples were gently mixed and centrifuged 30 minutes at 6000rpm. The remaining protein in supernatants was recovered for each ammonium sulfate percentage of saturation. Solubility curves were determined by measuring the protein concentration in the supernatant by UV-VIS measurements using NanoDrop™ 1000 Spectrophotometer. Measurements of remaining soluble protein in supernatants were normalized and used to estimate midpoints of relative solubility for every variant applying the Boltzmann sigmoidal model.

Short Term Stability Test

The scFv molecules were examined after two weeks incubation at 40° C. for the presence of soluble aggregates and degradation products. Proteins with a concentration of 10 mg/ml were dialyzed overnight at 4° C. against PBS with a broad range of pHs (3.5, 4.5, 5.5, 6.5, 7.0, 7.5 and 8.5). Control molecules with the same concentration in standard buffer PBS (pH 6.5) were stored at −80° C. during the 2 weeks period. Determination of degradation bands by SDS-PAGE was done at t=0 and t=14d time points and soluble aggregates were assessed in the SEC-HPLC. Determination of remaining activity after 2 weeks at 40° C. was done using Biacore.

EXAMPLE 1

Immunization Strategy for Generating Anti-VEGF Antibodies

In this example, an immunization strategy is described which used a novel antigenic VEGF-derived peptide, to generate antibodies capable of recognizing human, mouse and rabbit VEGFA.

From alanine-scanning mutagenesis studies performed at Genentech the residues of VEGFA that are crucial for high affinity interaction with VEGFr are known (Fuh, G. et al, (2006) *J. Biol. Chem.* 281, 6625-6631). Although the receptor-binding site probably represents a conformational epitope, most of the crucial residues lie on an alpha helix, on the first 10 amino acids of mature VEGFA.

Rabbit VEGFA contains three amino acids changes in this alpha helix, when compared to the human sequence; in contrast, mouse VEGFA is identical to human in this region. Thus, for the generation of mouse-human cross-reactive antibodies, rabbit presents a suitable species for immunization. In addition, rabbit immunization can lead to Abs with higher affinity than mouse immunization.

As outlined above, interaction with residues on the N-terminal alpha helix of VEGFA seems to be most crucial for binding to VEGFR1. Therefore, this 10 amino acid long stretch can be used as an epitope for immunization. Alternatively, full length VEGFA can be injected, however, other peptide stretches on VEGFA are more immunogenic, thus lowering the chance to raise neutralizing antibodies. This hypothesis is supported by the fact that two different peptides, both lying close to the C-terminus of VEGFA are potentially immunogenic as predicted by the method of Johnson and Wolf. This method predicts only minor immunogenic potential for the N-terminal alpha helix. Therefore, immunization with the peptide constituting the alpha helix only, can be more straightforward than immunization with full-length VEGFA. The probability to elicit a strong immune response can be further increased by fusion or chemical coupling of the peptide to Keyhole Limpet Hemocyanin (KLH).

Four immunization strategies were performed as follows
A. Pre-Immunization of rabbits with full-length human VEGFA$_{165}$ to enhance the probability to obtain conformational binders. Second boost with peptide from aa stretch 16-KFMDVYQRSYCHP-2 (SEQ ID NO: 183) (underline: receptor interaction; double underline, divergent in rabbit, Cys is involved in disulfide bond according to crystal structure). The Cys contained in the peptided sequence could be used for coupling to KLH and would therefore not be exposed as free Cys. The final peptide would look as follows: KFMDVYQRSY-Cys-KLH (SEQ ID NO: 184).
B. Pre-Immunization of mice with full-length VEGFA$_{165}$ to enhance the probability to obtain conformational binders. Second boost with peptide from aa stretch 16-KFMDVY-QRSYCHP-28 (SEQ ID NO: 183) Cys is involved in disulfide bond according to crystal structure). The Cys contained in the peptided sequence can be used for coupling to KLH and would therefore not be exposed as free Cys. The final peptide would look as follows: KFM-DVYQRSY-Cys-KLH (SEQ ID NO: 184)
C. Pre-immunization of rabbits/mice with peptide from aa stretch 16-KFMDVYQRSYCHP-28 (SEQ ID NO: 183) (final peptide: KFMDVYQRSY-Cys-KLH; SEQ ID NO: 184). Second boost with full-length VEGFA$_{165}$ to enhance the probability to obtain conformational binders.
D. Immunization with full length VEGFA$_{165}$ in rabbits.

EXAMPLE 2

CDR Grafting and Functional Humanization of Monoclonal Rabbit Anti-VEGF Antibodies.

Grafting of Rabbit CDRs

Unlike traditional humanization methods which employ the human antibody acceptor framework that shares the greatest sequence homology with the non-human donor antibody, the rabbit CDRs were grafted into either framework FW1.4 (SEQ ID No. 172) to generate a Min-graft or into the "rabbitized" framework rFW1.4 (SEQ ID No. 173) or its variant rFW1.4(v2) (SEQ ID No. 174) to generate a Max-graft. Both frameworks were selected primarily for desirable functional properties (solubility and stability), structural suitability to accommodate a large variety of rabbit CDRs and reasonable homology to the rabbit variable domain consensus sequence. Framework rFW1.4 is a derivative of FW1.4 that was further engineered with the aim to serve as universal acceptor framework for virtually any set of rabbit CDRs. Although the stable and soluble framework sequence FW1.4 exhibits high homology to rabbit antibodies, it is not the most homologous sequence available.

Identification of Residues Potentially Involved in Binding

For each rabbit variable domain sequence, the nearest rabbit germline counterpart was identified. If the closest germline could not be established, the sequence was compared against the subgroup consensus or the consensus of rabbit sequences with a high percentage of similarity. Rare framework residues were considered as possible result of somatic hypermutation and therefore playing a role in antigen binding. Consequently, such residues were considered for grafting onto the acceptor framework rFW1.4 or rFW1.4 (v2) to generate Max-grafts. Particularly, residues potentially implicated in direct antigen contact or influencing disposition of VL and VH were grafted. Further residues described to influence CDR structure were substituted if required. No framework substitutions were made when CDRs were grafted onto FW1.4 (Min-grafts). For example to generate 578minmax residue VH 94 (H94) of rFW1.4 was mutated to corresponding residue in the donor sequence. The rabbit antibody 578 contains Gly at H94 whereas both, the most homologous germline and the rabbit consensus contain Arg at position H94. Gly has an exceptional flexibility (positive phi angles) that is not found for other amino acids. This suggests a role in mainchain torsion angle and a possible strong influence of the loop conformation with implications on activity. Further examples of framework positions that were grafted to obtain the Max-grafts as disclosed herein can be identified by making a sequence alignment of the framework regions of rFW1.4, rFW1.4(v2) and the scFv sequences of interest provided herein. Webtools as known in the art may for example be used for said purpose (e.g. ClustalW or MultiAlin). All framework positions at which rFW1.4 and rFW1.4(v2) contain the same residue and at which the scFv of interest reveals a different residue, are framework positions that were grafted to obtain the Max-grafts.

Domain Shuffling

Variable light chains of Min-grafts were combined with variable heavy chain Max-grafts to identify optimal combinations in terms of biophysical properties (solubility and stability) and activity.

Cloning and Expression of scFvs

The scFvs described and characterized herein were produced as follows. The humanized VL sequences (SEQ ID NOs:82-106) were connected to humanized VH sequences (SEQ ID NOs:118-166) via the linker of SEQ ID NO:181 to yield an scFv of the following orientation: NH$_2$—VL-linker-VH—COOH. In many cases DNA sequences encoding for the various scFvs were de novo synthesized at the service provider Entelechon GmbH. The resulting DNA inserts were cloned into the bacterial expression vector pGMP002 via NcoI and HindIII restriction sites introduced at the 5' and 3' end of the scFv DNA sequence, respectively. Between the DNA sequence of the VL domain and the VH domain, a BamHI restriction site is located. In some cases the scFv encoding DNA was not de novo synthesized, but the scFv expressing constructs were cloned by domain shuffling. Accordingly, the VL domains were excised and introduced into the new constructs via NcoI and BamHI restriction sites, the VH domains via BamHI and HindIII restriction sites. In other cases, point mutations were introduced into the VH and/or VL domain using state of the art assembling PCR methods. The cloning of GMP002 is described in Example 1 of WO2008006235. The production of the scFvs was done analogue as for ESBA105 as described in Example 1 of WO2008006235.

EXAMPLE 3

Biacore Binding Analysis of Anti-VEGF scFvs

In this example, the Biacore-binding ability of scFvs was tested and the binding affinity was measured using the exemplary surface plasmon resonance method with BIAcore™-T100. The VEGF proteins, tested for binding by these scFv candidates, in this example and later examples include purified *Escherichia coli*-expressed recombinant human $VEGF_{165}$ (PeproTech EC Ltd.), recombinant human $VEGF_{121}$ (PeproTech EC Ltd.), recombinant human $VEGF_{110}$ (ESBATech AG), recombinant murine $VEGF_{164}$ (PeproTech EC Ltd.), recombinant rat $VEGF_{164}$ (Biovision), recombinant rabbit $VEGF_{110}$ (ESBATech AG), and recombinant human PLGF (PeproTech EC Ltd.). For the surface plasmon resonance experiment, carboxymethylated dextran biosensor chips (CM4, GE Healthcare) were activated with N-ethyl-N'-(3-dimethylaminopropyl) carbodiimide hydrochloride and N-hydroxysuccinimide according to the supplier's instructions. Each of the 6 different VEGF forms, as exemplified above, was coupled to 1 of the 4 different flow cells on a CM4 sensor chip using a standard amine-coupling procedure. The range of responses obtained with these immobilized VEGF molecules after coupling and blocking were ~250-500 response units (RU) for $hVEGF_{165}$, ~200 RU for $hVEGF_{110}$, $hVEGF_{121}$, murine $VEGF_{164}$, rat $VEGF_{164}$ and rabbit $VEGF_{110}$ and ~400 RU for PLGF. The 4th flow cell of each chip was treated similarly except no proteins were immobilized prior to blocking, and the flow cell was used as in-line reference. Various concentrations of anti-VEGF scFvs (e.g., 90 nM, 30 nM, 10 nM, 3.33 nM, 1.11 nM, 0.37 nM, 0.12 nM and 0.04 nM) in HBS-EP buffer (0.01 M HEPES, pH 7.4 or 5, 0.15 M NaCl, 3 mM EDTA, 0.005% surfactant P20) were injected into the flow cells at a flow rate of 30 µl/min for 5 min. Dissociation of the anti-VEGF scFv from the VEGF on the CM4 chip was allowed to proceed for 10 min at 25° C. Sensorgrams were generated for each anti-VEGF scFv sample after in-line reference cell correction followed by buffer sample subtraction. The apparent dissociation rate constant ($k_d$), the apparent association rate constant ($k_a$) and the apparent dissociation equilibrium constant ($K_D$) were calculated using one-to-one Langmuir binding model with BIAcore T100 evaluation Software version 1.1.

Figure 1A:
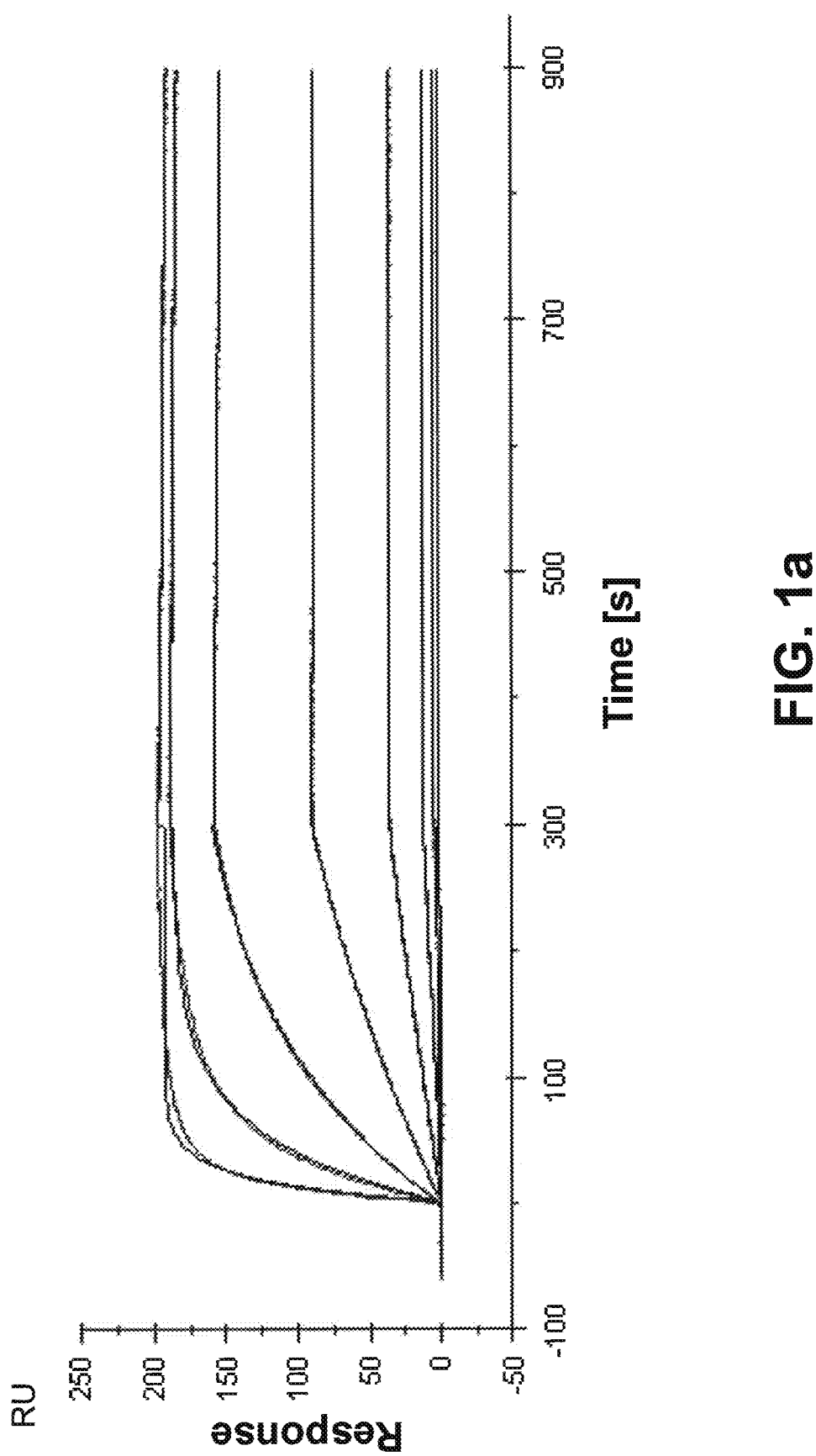
FIGS. 1a and 1b illustrate the binding kinetics of selected scFvs to hVEGF$_{165}$ using Biacore (hVEGF165).
Figure 1B:
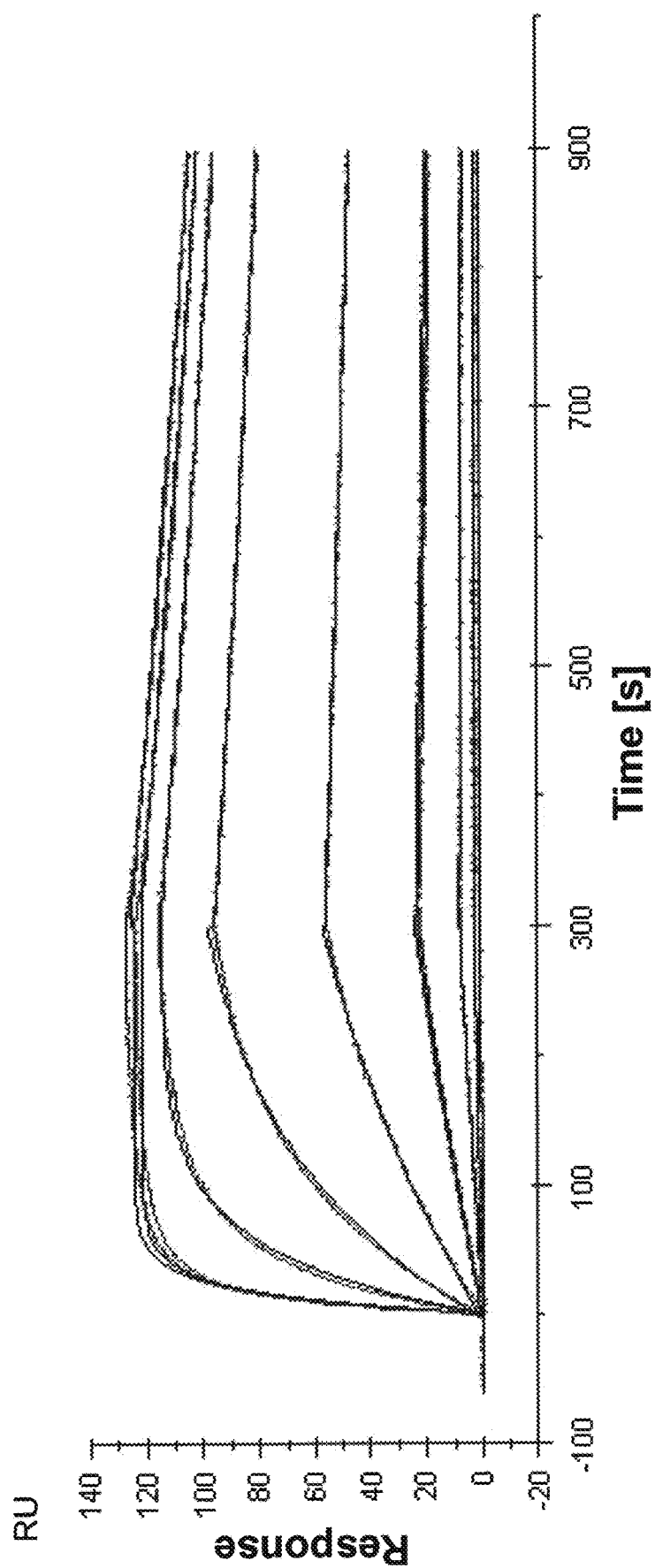
Figure 2A:
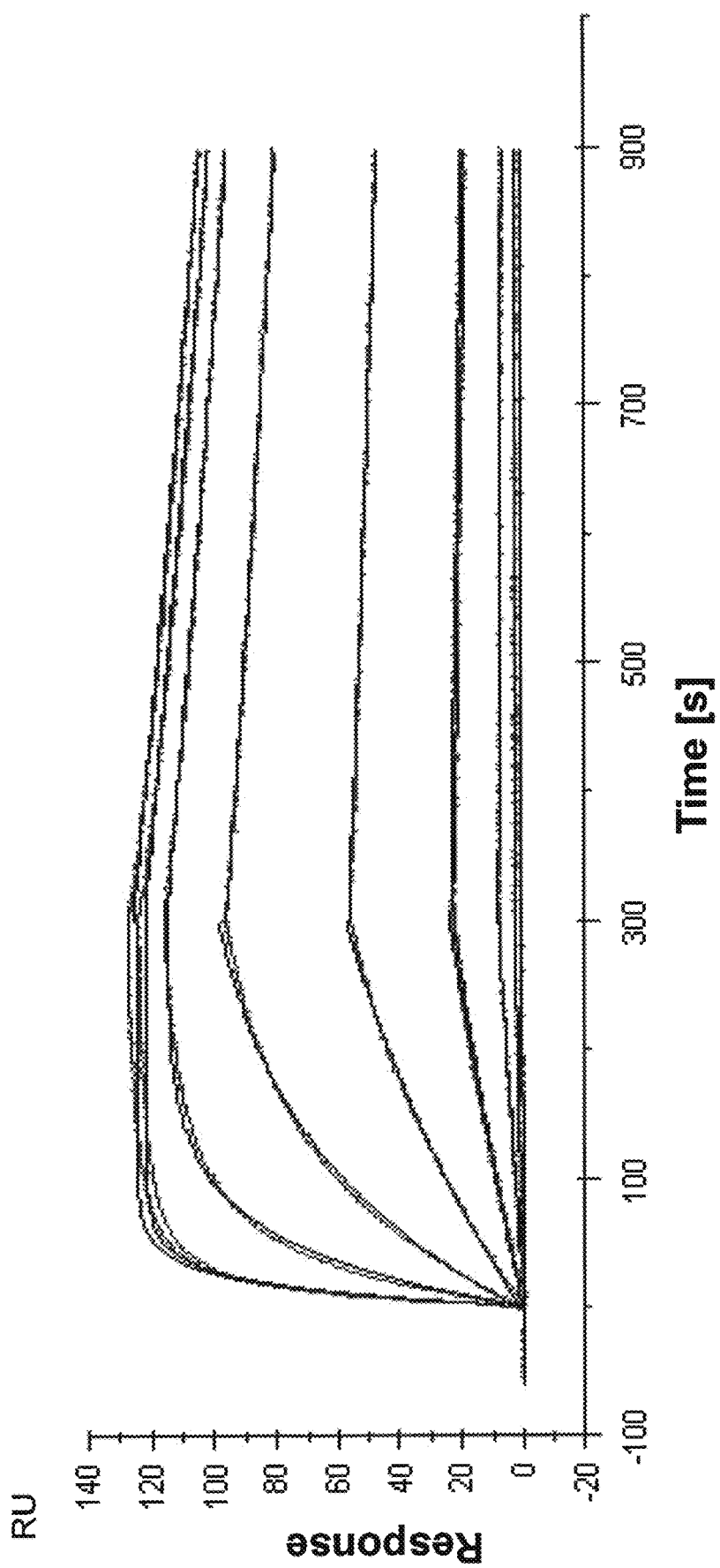
FIGS. 2a, 2b and 2c illustrate the species specificity by showing binding kinetics of 578max to human, mouse and rat VEGF.
Figure 2B:
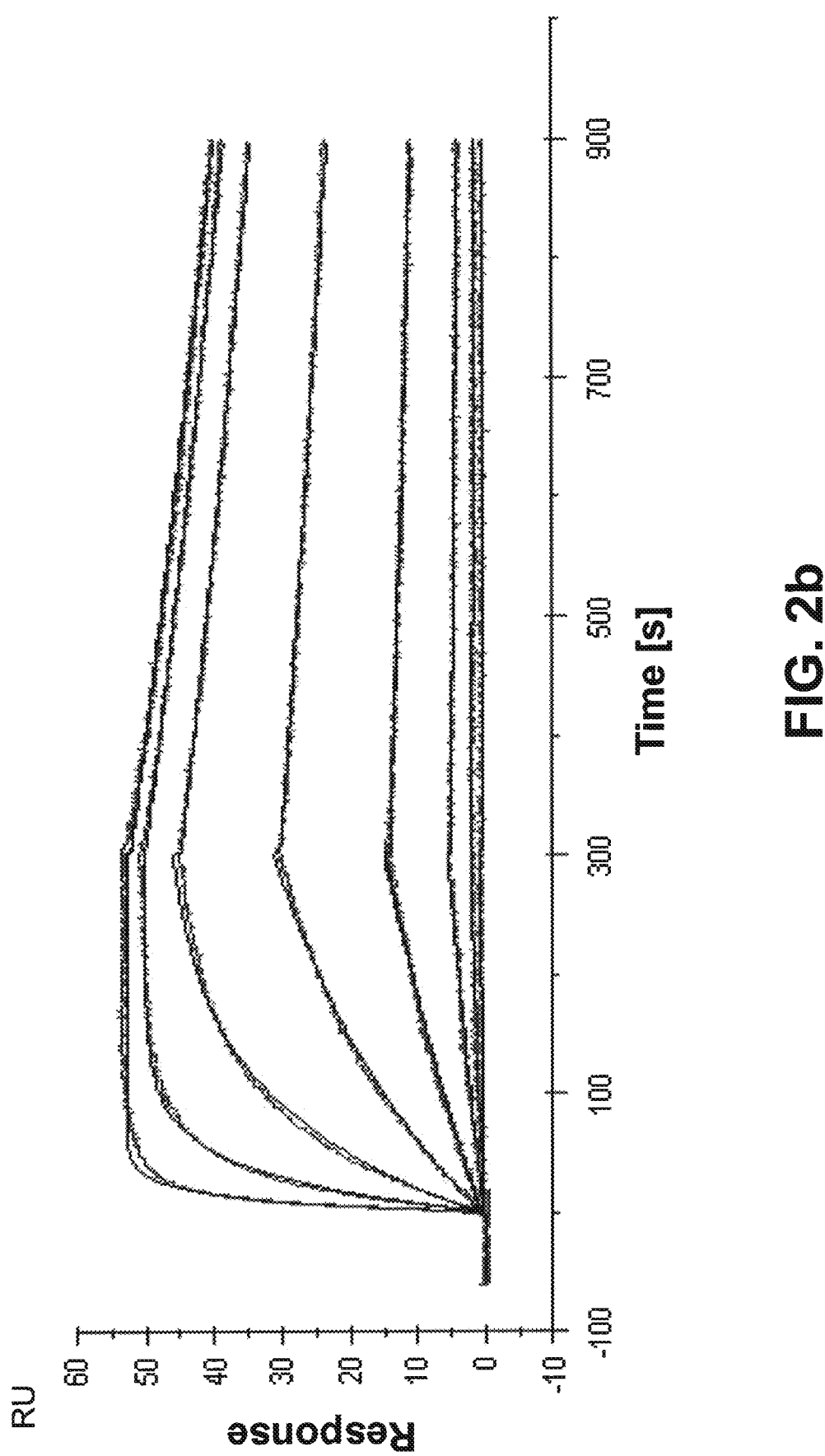
Figure 2C:
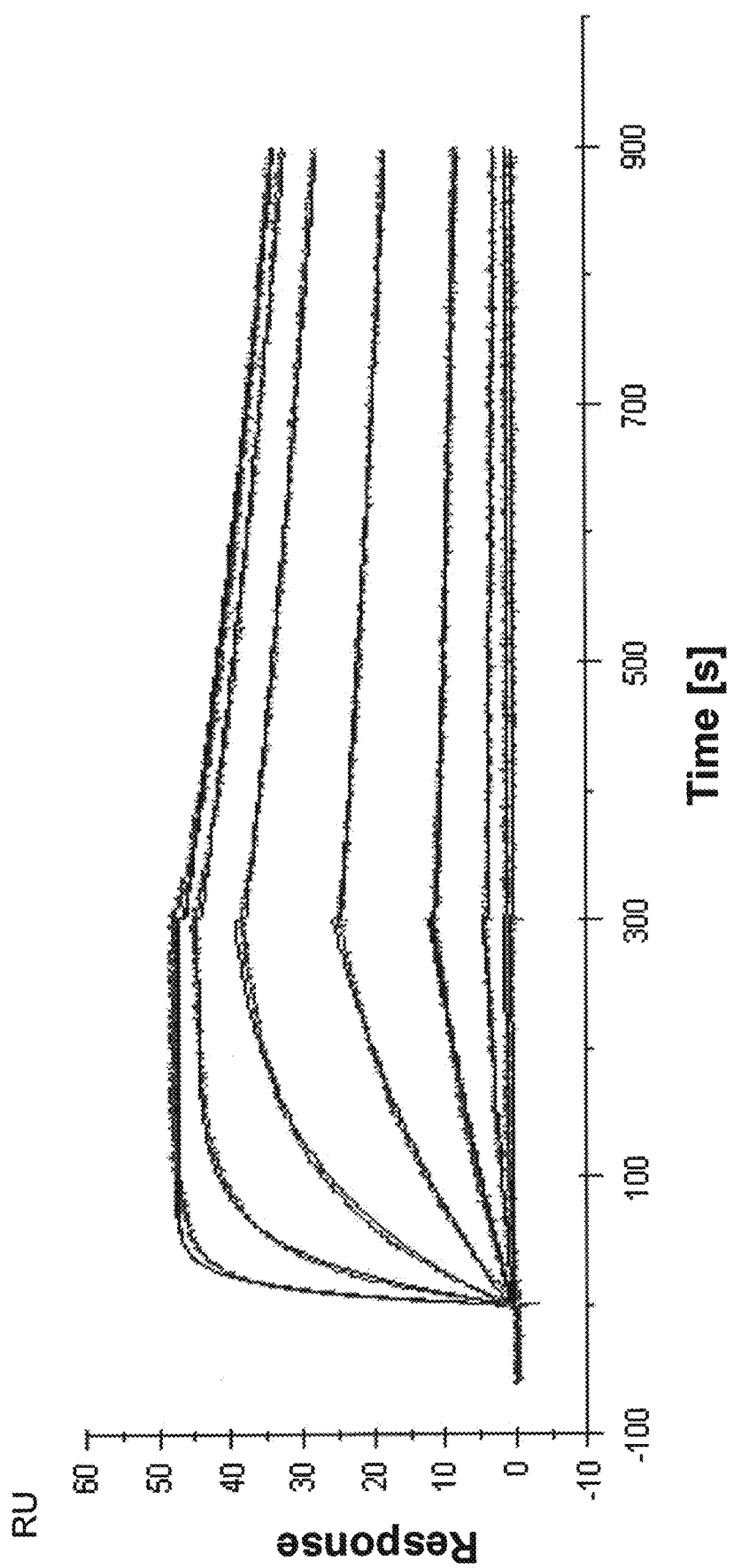

As one exemplary result, some lead anti-VEGF scFv candidates are listed in Table 7 showing their binding affinity to $hVEGF_{165}$. Their potency as VEGF inhibitors, which is measured using VEGFR competition ELISA and/or HUVEC assay and described in latter examples, is also shown in Table 7. The kinetics curves of some exemplary lead candidates, e.g., 511max and 578max, for their binding to $hVEGF_{165}$ are illustrated in FIG. 1. Their affinity constants ($k_d$, $k_a$ and $K_D$) were also determined. Some lead candidates also display species specificity in their binding to various VEGF proteins of different sources. For example, some affinity data measured at pH5 using mouse and rat $VEGF_{164}$ as binding partner are shown in Tables 8 a and b. An exemplary lead scFv candidate, 578minmax, has a $K_D$ of 5.76E-10 M and 7.48E-10 M in its binding to mouse and rat $VEGF_{164}$, respectively at a pH of 5 (Tables 8 a and b) and 2.73E-11 and 2.19E-11 at a pH of 7.4 (data not shown). This species specificity is further illustrated in FIG. 2 in the kinetics curves and affinity data for the binding between 578minmax and human, mouse or rat VEGF proteins.

Figure 3A:
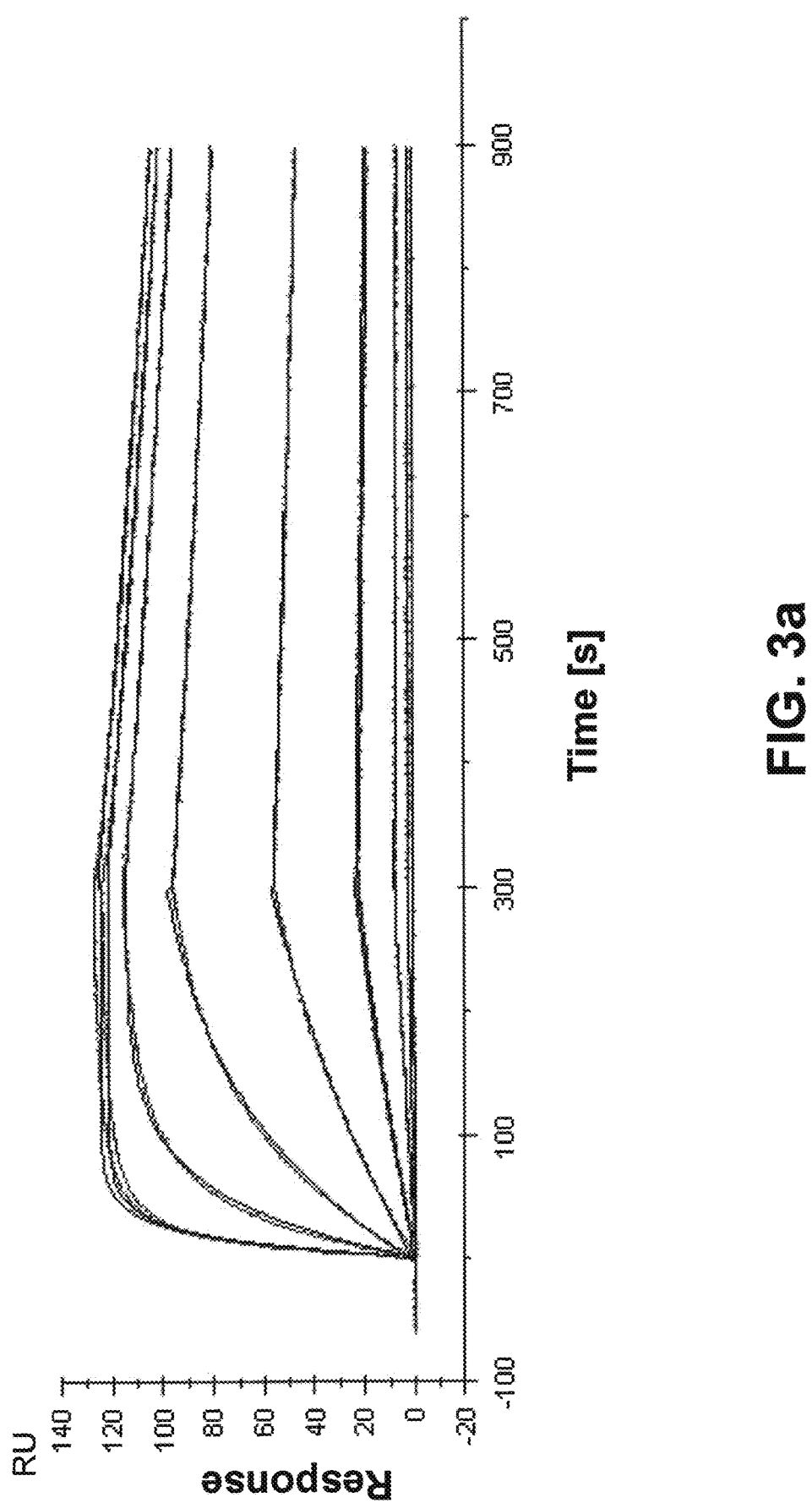
FIGS. 3a, 3b and 3c illustrate the binding kinetics of 578max to VEGF isoforms (hVEGF121 and hVEGF110).
Figure 3B:
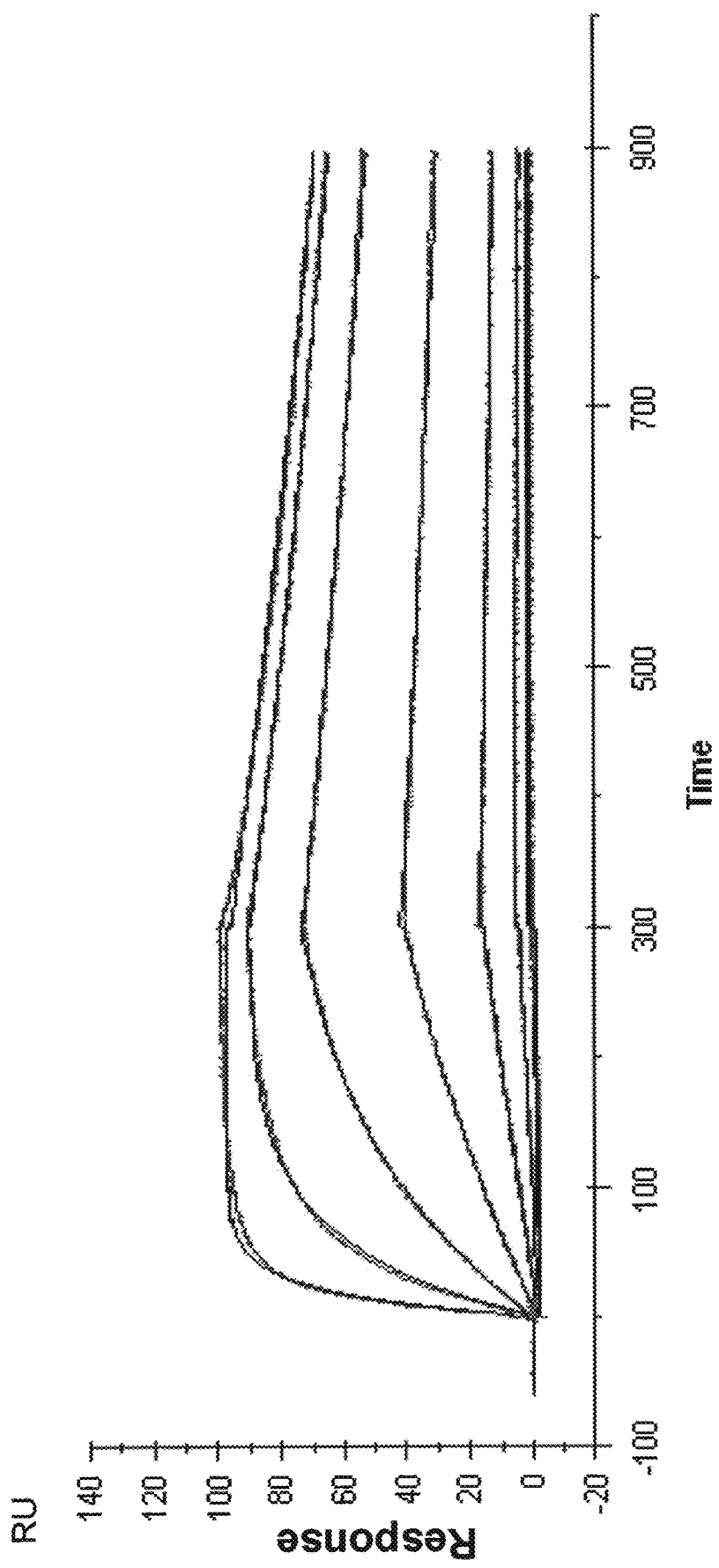
Figure 3C:
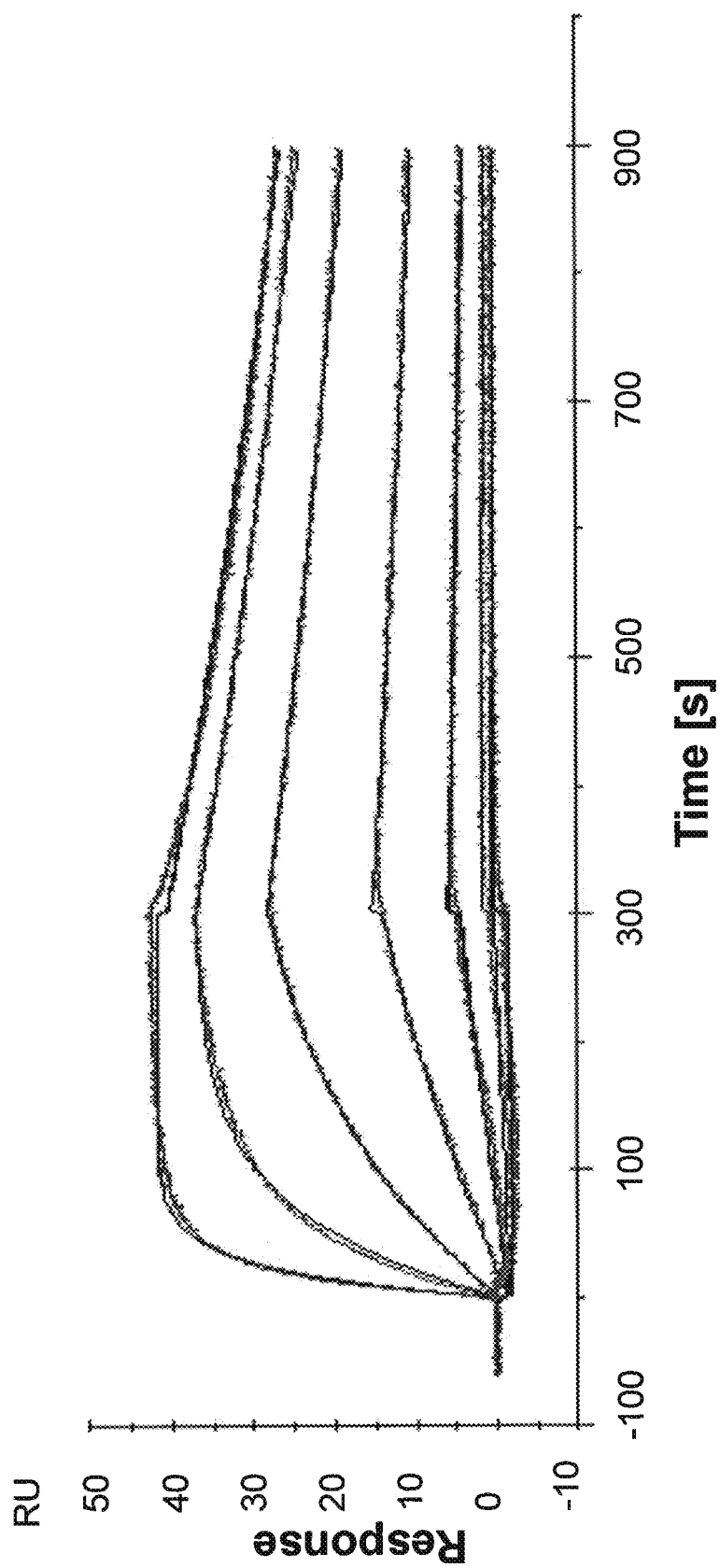

Besides the species specificity in their binding to VEGFs from different organisms, many lead scFv candidates also display differentiated binding affinities towards various VEGF isoforms. For example, the affinity data measured at pH 5.0 for some scFv candidates binding to human $VEGF_{165}$, $VEGF_{121}$ and $VEGF_{110}$ are compared in Table 9. In the same experiments, PlGF protein was also used as a negative control without binding capacity to those scFv candidates. Also, the differentiated kinetics curves and affinity data for the binding between 578Max and VEGF isoforms, as an example, are illustrated in FIG. 3.

Figure 4A:
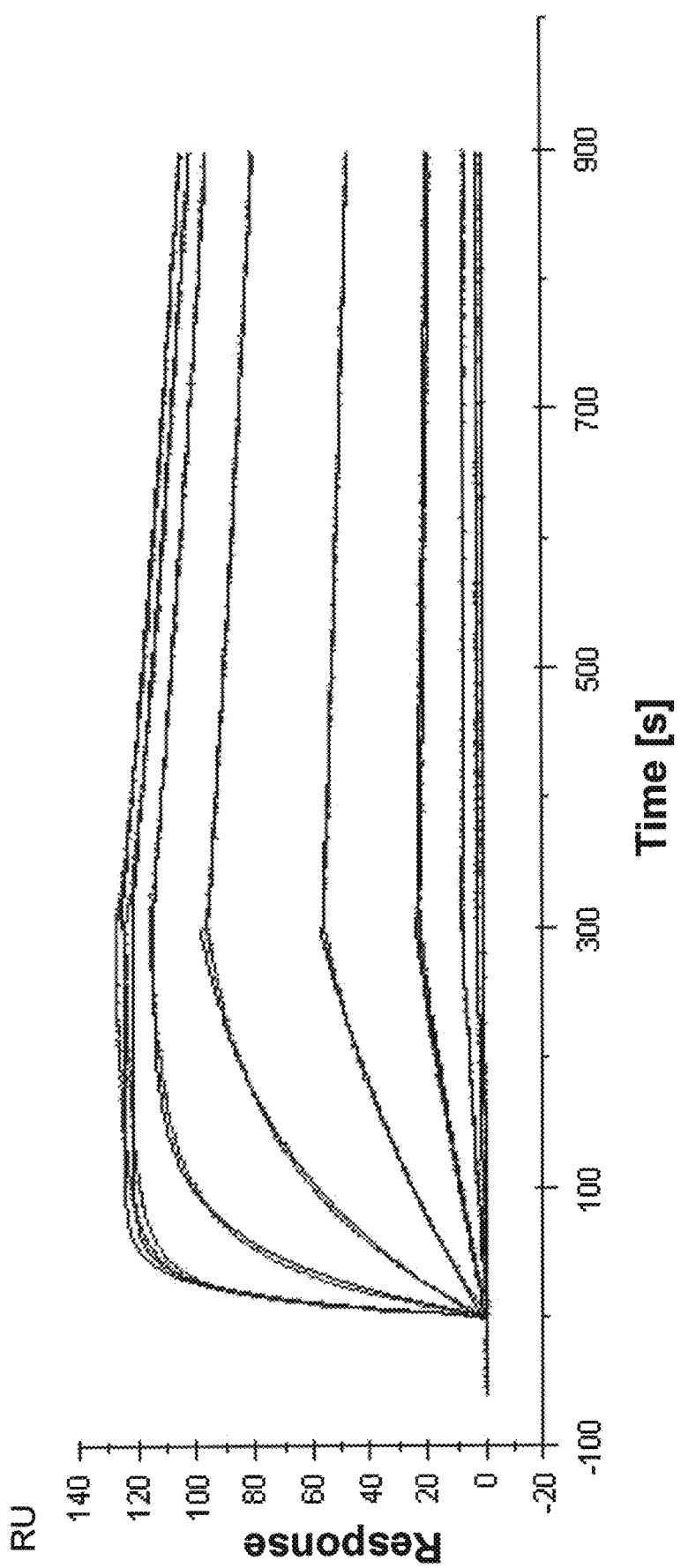
FIGS. 4a, 4b and 4c depict the binding kinetics of 578max, 578minmax and 578 wt to hVEGF165.
Figure 4B:
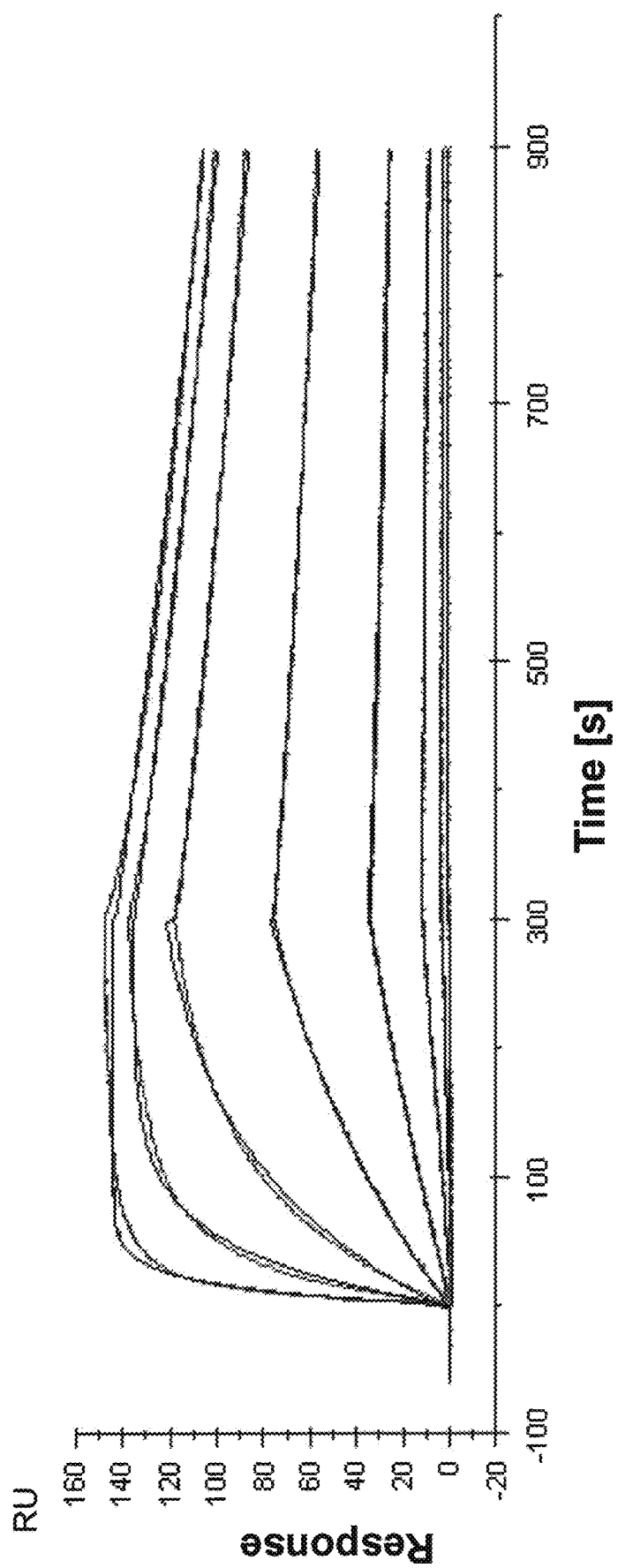
Figure 4C:
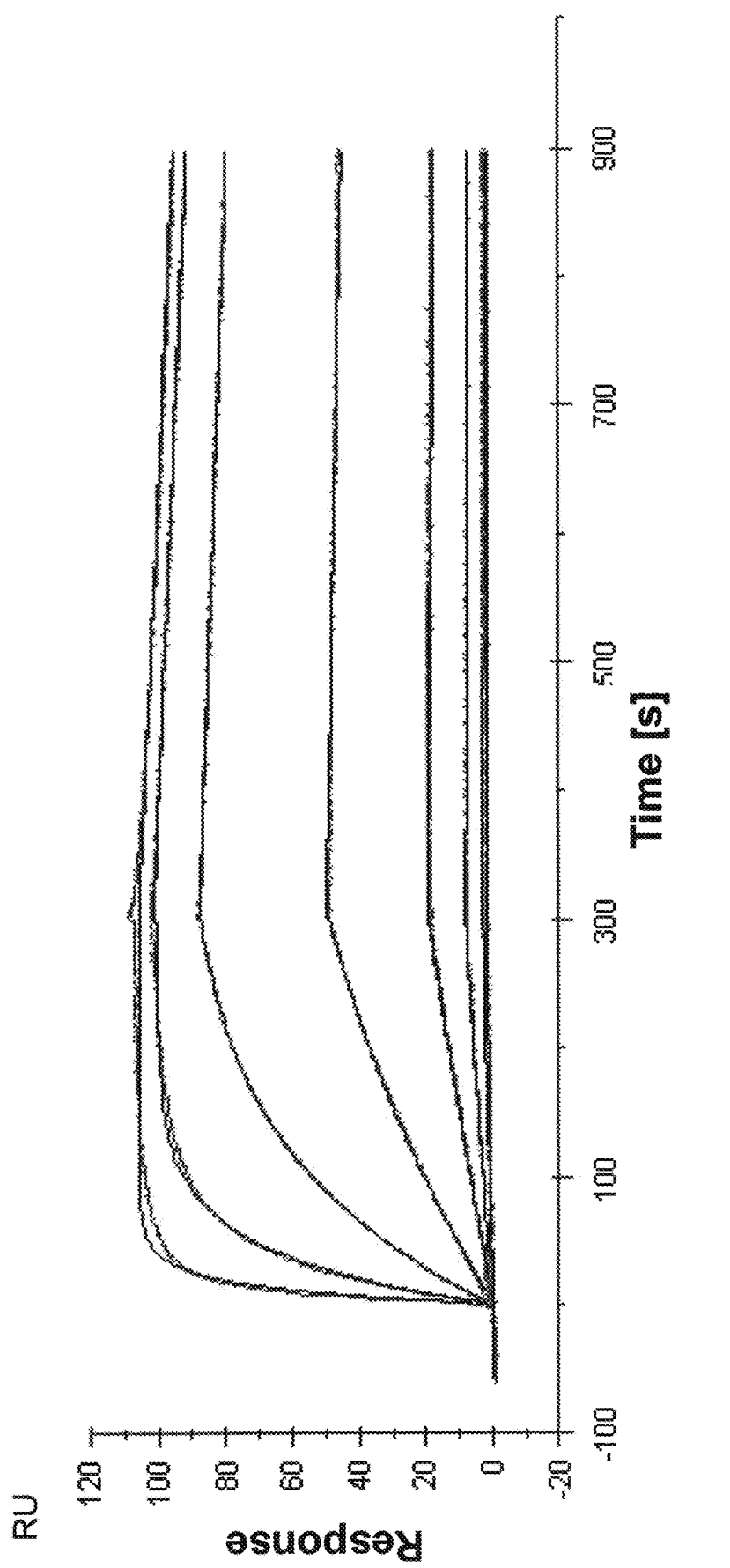

The present invention also discloses derivatives originating from the lead anti-VEGF scFv candidates, which are mentioned above. Some lead derivatives of candidate 578 and 511, as listed in Table 10, are exemplified for their affinity and potency (measured at pH 5.0). In this experiment, Biacore measurement was used for the affinity of these derivatives towards $hVEGF_{165}$, while hVEGFR2 competition ELISA and/or HUVEC assay were used to define their potency to inhibit VEGFs (Table 10). Three derivatives, 578max, 578minmax and 578 wt-His, are further exemplified in their kinetics curves and affinity data for binding to $hVEGF_{165}$ in FIG. 4.

Figure 5A:
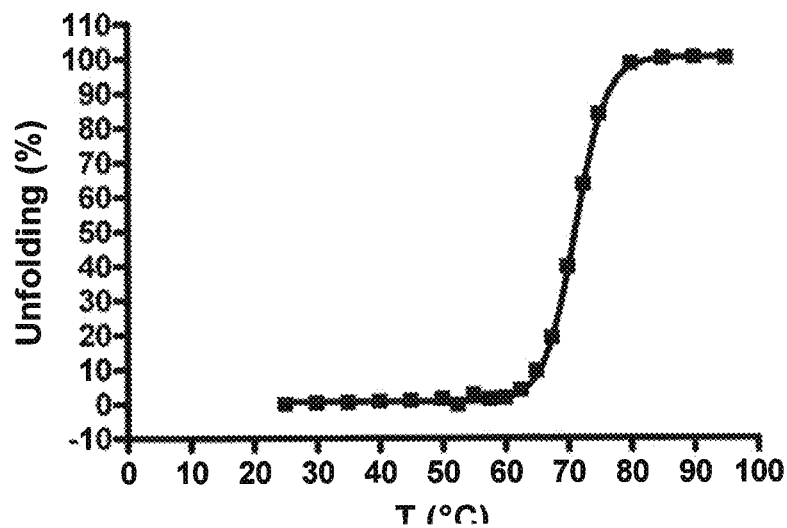
FIGS. 5a, 5b and 5c illustrate thermal stability of 578max, 578minmax and 578minmax_DHP (unfolding measured by FT-IR).
Figure 5B:
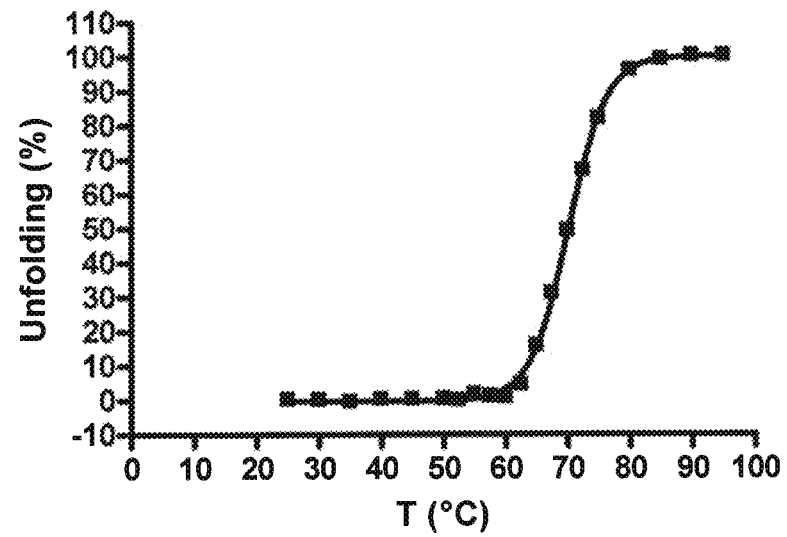
Figure 5C:
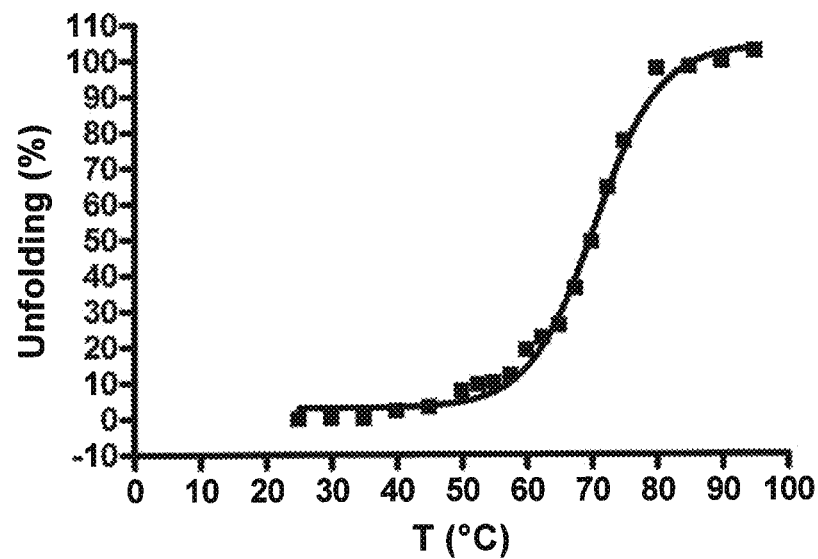
Figure 6A:
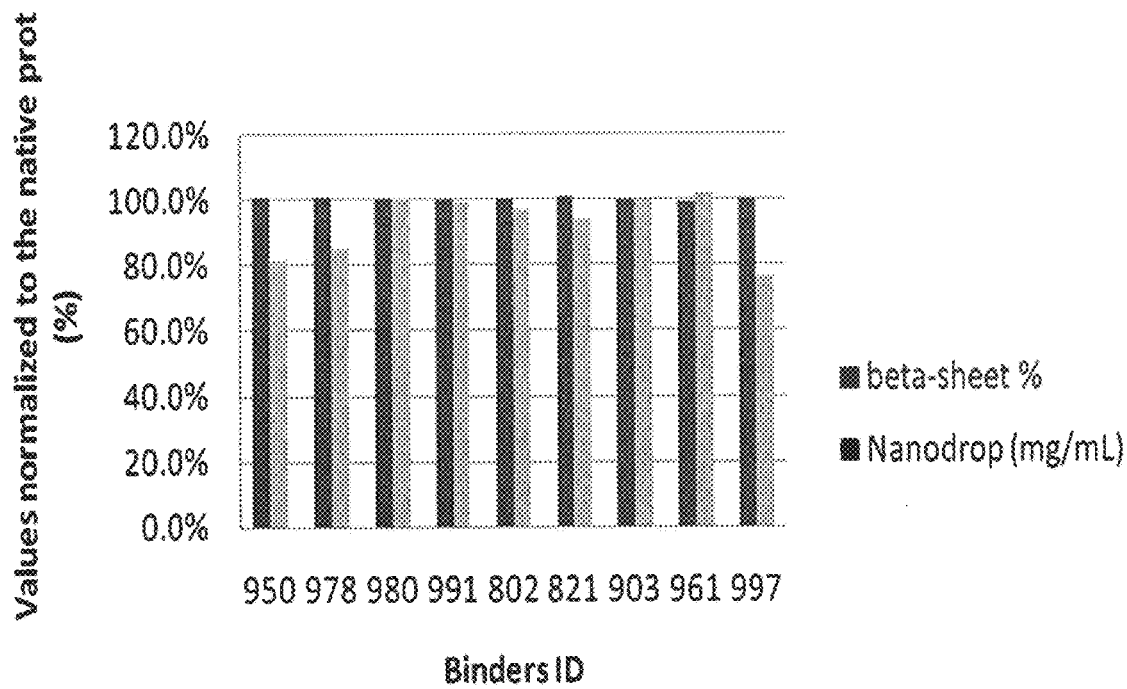
FIGS. 6a, 6b and 6c illustrate denaturation and precipitation of 578 derivatives after thermal stress (FIG. 6a: 50° C., FIG. 6b: 60° C., FIG. 6c: 70° C.) for 30 min.
Figure 6B:
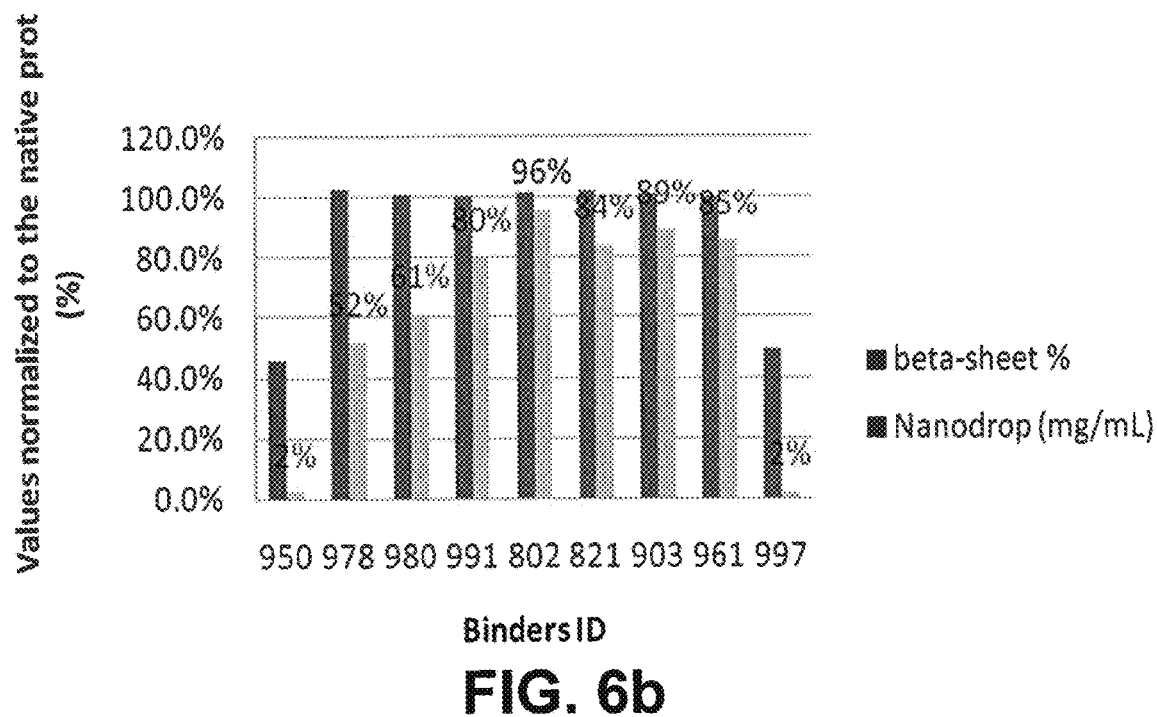
Figure 6C:
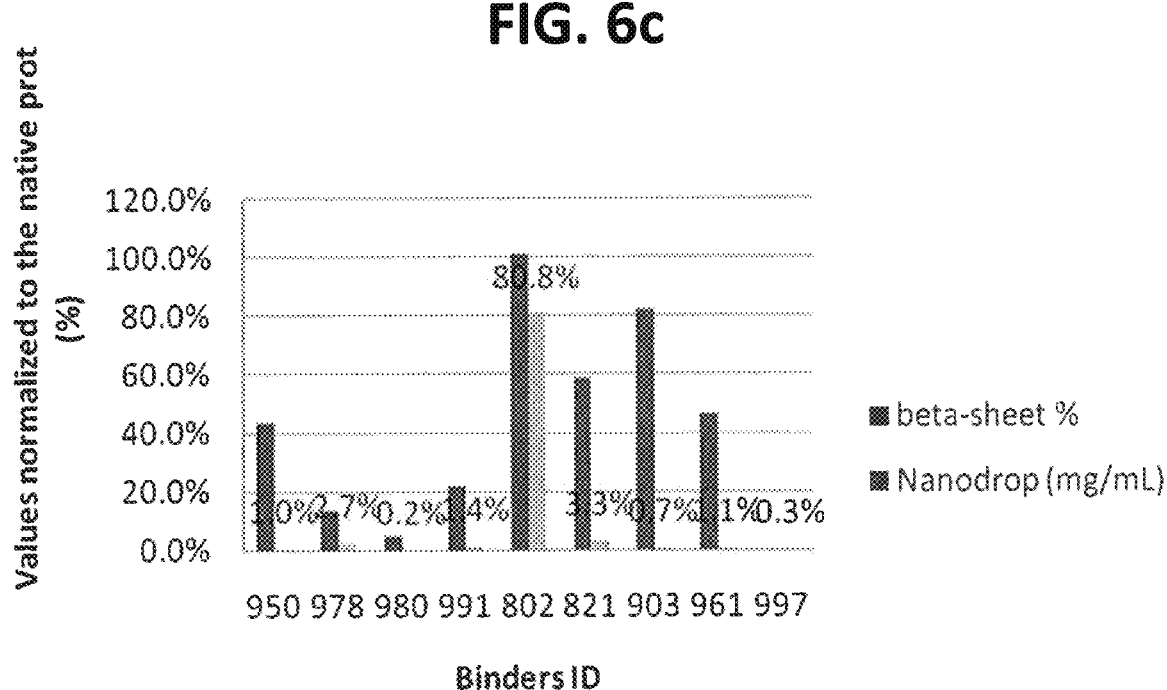
Figure 7A:
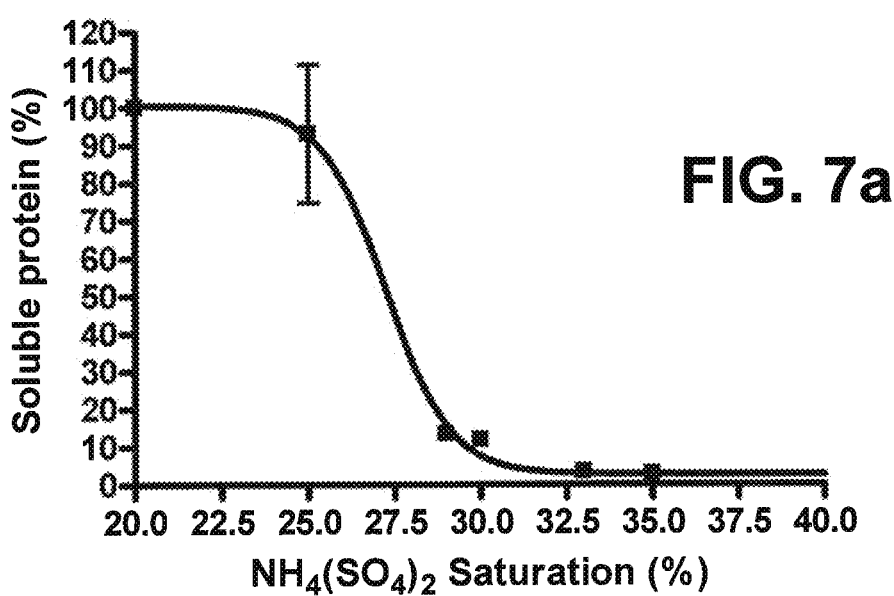
FIGS. 7a, 7b and 7c illustrate solubility of 578max, 578minmax and 578minmax_DHP (determined by ammonium sulfate precipitation).
Figure 7B:
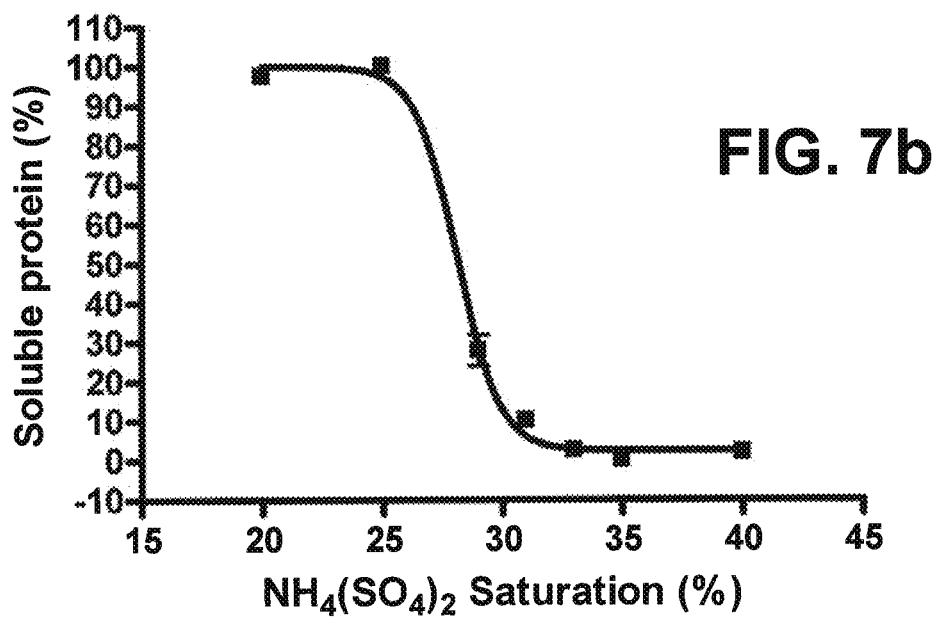
Figure 7C:
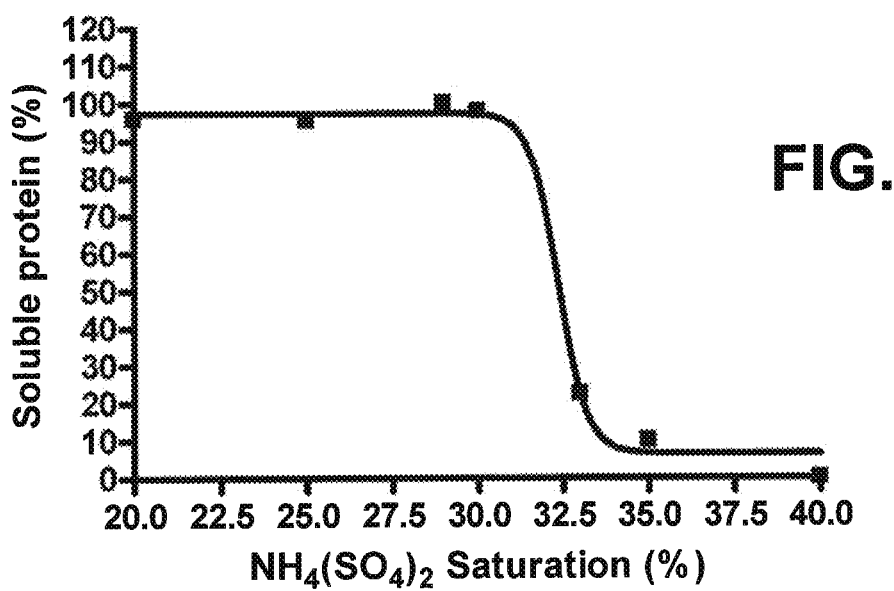
Figure 8A:
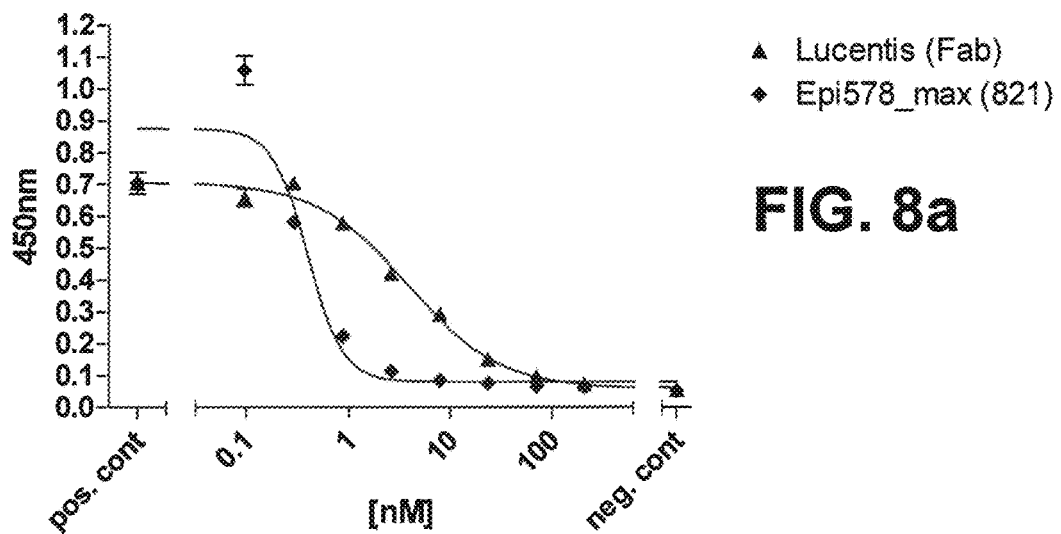
FIGS. 8a, 8b, 8c and 8d illustrate VEGFR2 competition ELISA versus HUVEC assay as methods to measure potency.
Figure 8B:
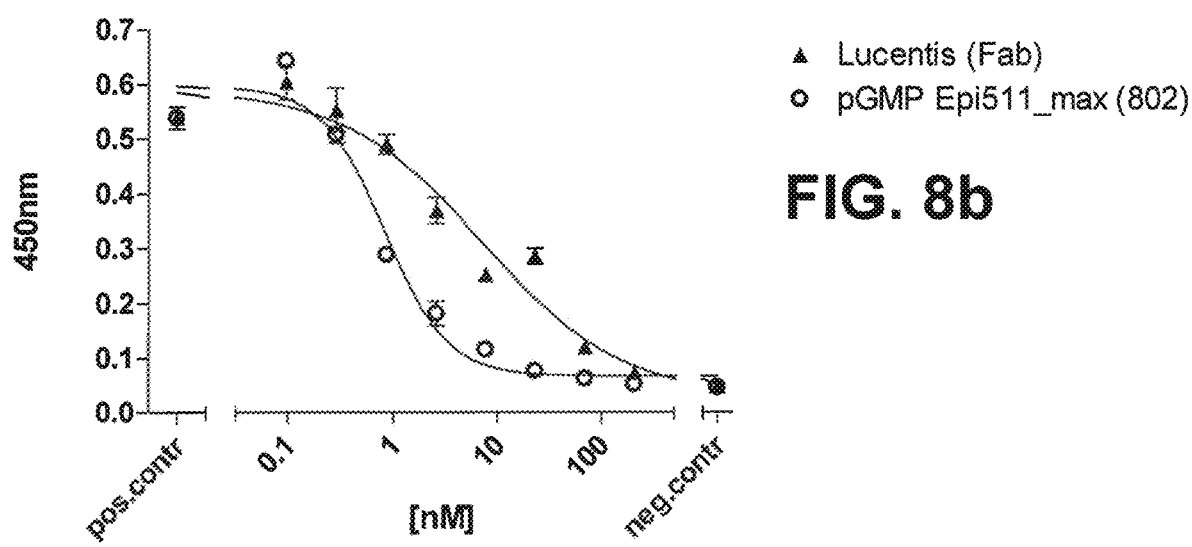
Figure 8C:
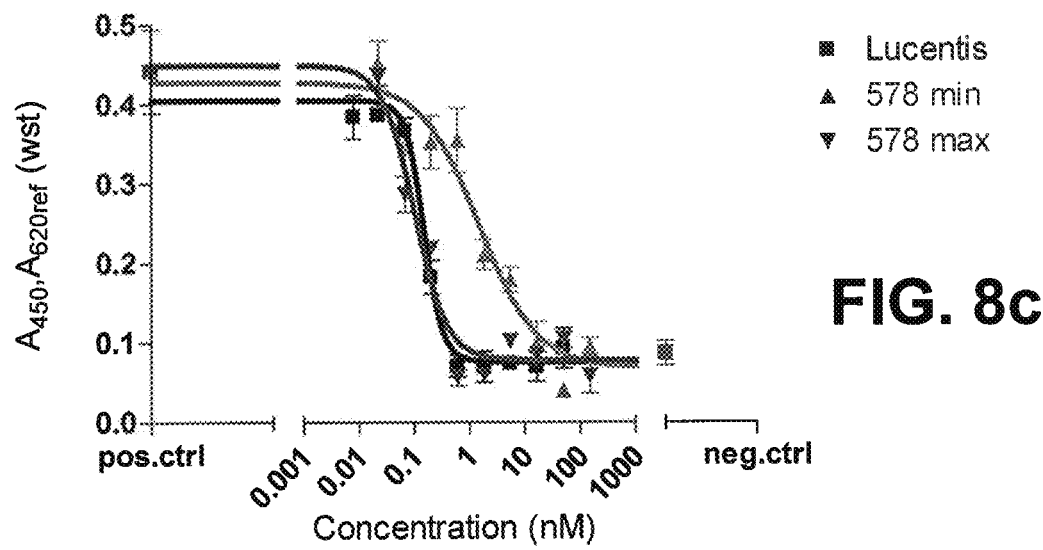
Figure 8D:
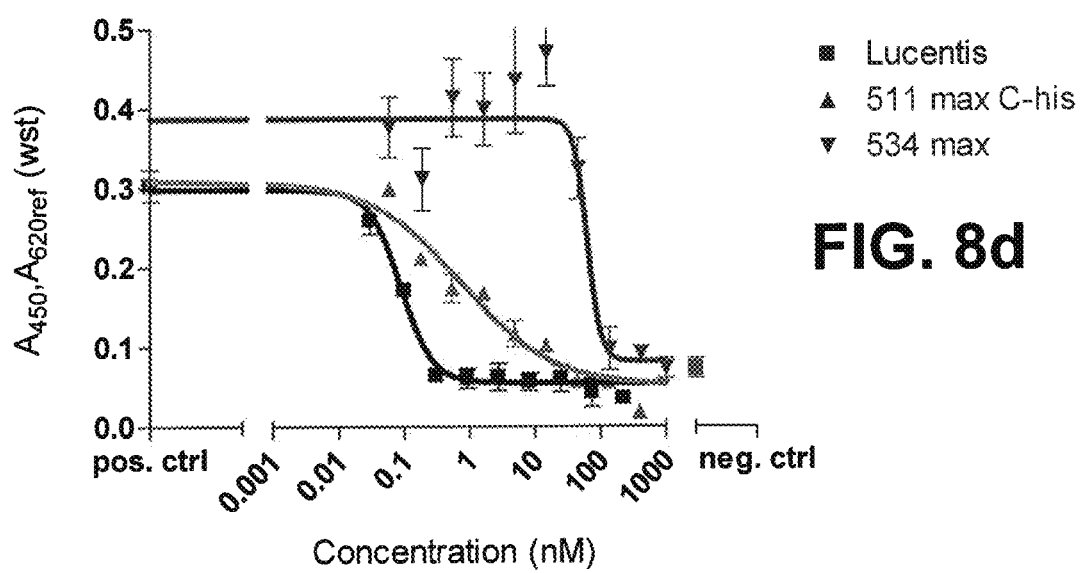

For derivatives of lead candidates, their biophysical characterizations were determined and exemplified in FIGS. 5-7 and table 11. These characteristics include, as exemplified in table 11, $T_m$ determined by FTIR, the percentage of β-sheet or protein loss after incubation at 60° C. for 30 min, solubility determined by ammonium sulfate precipitation, refolding yield during the production process and expression levels in *E. coli*. Three derivatives, 578max, 578minmax and 578minmax DHP, were characterized for their thermal stability in their unfolding curves against different temperatures measured by FT-IR (FIG. 5).

TABLE 7 overview of affinity and potency of lead candidates

| ID | Protein Nr. | Rel. activity hVEGR2 comp. ELISA ($EC50_{Luc}$ [nM]/$EC50_{test}$ [nM]) | Rel. activity hVEGR1 comp. ELISA ($EC50_{Luc}$ [nM]/$EC50_{test}$ [nM]) | Rel. activity in HUVEC assay ($EC50_{Luc}$ [nM]/$EC50_{test}$ [nM]) |
|---|---|---|---|---|
| 375-min | 857 | 0.3 | ND | ND |
| 375-max | 873 | 0.6 | ND | ND |
| 509-min | 854 | 1.0 | 2.9 | ND |
| 509-max | 855 | 4.1 | 13 | 0.003 |
| 509-maxII | 856 | 0.6 | 0.09 | 0.0009 |
| 511-min | 801 | 4.9 | 0.7 | 0.0011 |
| 511-max | 802 | 8.7 | 8 | 0.0179 |
| 534-min C-His | 807 | 0.1 | ND | ND |
| 534-max | 793 | 1.1 | ND | 0.0014 |
| 567-min | 884 | 9.7 | 14.9/57 | ND |
| 567-max | 874 | 4.1 | 15.7/54.5 | 0.0086 |
| 578-min | 820 | 4.1 | 4.8 | 0.1001 |
| 578-max | 821 | 9.6 | 35.5/51.6 | 1.483 |
| 610-min | 882 | 0.1 | ND | ND |
| 610-max | 883 | 0.4 | ND | ND |

TABLE 7-continued overview of affinity and potency of lead candidates

| 435-min | 944 | 0.03 | ND | ND |
| 435-max | 945 | 7.6 | 0.00039 | ND |

| | Biacore Measurements (pH 5) hVEGF$_{165}$ | | | Biacore Measurements (pH 7.4) hVEGF$_{165}$ | | |
| --- | --- | --- | --- | --- | --- | --- |
| ID | ka (1/Ms) | kd (1/s) | KD (M) | ka (1/Ms) | kd (1/s) | KD (M) |
| 375-min | 9.27E+05 | 5.01E−03 | 5.41E−09 | >E+08 | 3.86E+00 | NA |
| 375-max | 2.44E+06 | 6.55E−03 | 2.68E−09 | 5.09E+07 | 2.42E−01 | 4.74E−09 |
| 509-min | 6.23E+05 | 1.14E−03 | 1.82E−09 | 3.52E+06 | 1.08E−02 | 3.06E−09 |
| 509-max | 2.26E+06 | 2.72E−03 | 1.21E−09 | 1.42E+06 | 5.37E−04 | 3.78E−10 |
| 509-maxII | 8.38E+05 | 2.82E−03 | 3.37E−09 | 7.59E+06 | 1.98E−02 | 2.61E−09 |
| 511-min | 5.05E+05 | 1.28E−03 | 2.53E−09 | 6.75E+05 | 8.85E−04 | 1.31E−09 |
| 511-max | 6.59E+05 | 4.40E−05 | 6.67E−11 | 8.00E+05 | 6.85E−05 | 8.56E−11 |
| 534-min C-His | 2.71E+05 | 9.21E−03 | 3.41E−08 | ND | ND | ND |
| 534-max | 1.88E+06 | 1.73E−02 | 9.21E−09 | 1.06E+06 | 2.62E−03 | 2.47E−09 |
| 567-min | 2.01E+06 | 4.61E−04 | 2.30E−10 | 1.11E+06 | 7.00E−04 | 6.31E−10 |
| 567-max | 1.20E+06 | 2.26E−04 | 1.88E−10 | 1.17E+06 | 1.67E−04 | 1.43E−10 |
| 578-min | 1.14E+06 | 1.03E−02 | 9.01E−09 | 1.11E+06 | 2.02E−04 | 1.81E−10 |
| 578-max | 7.00E+05 | 3.07E−04 | 4.39E−10 | 1.58E+06 | 3.76E−05 | 2.37E−11 |
| 610-min | 2.51E+05 | 2.65E−03 | 1.06E−08 | No binding | No binding | No binding |
| 610-max | 5.09E+05 | 6.01E−04 | 1.18E−09 | >E+08 | 3.57E+01 | NA |
| 435-min | No binding | No binding | No binding | 4.95E+05 | 1.43E−02 | 2.89E−08 |
| 435-max | 1.67E+05 | 7.55E−04 | 4.53E−09 | 1.13E+06 | 1.04E−04 | 9.22E−11 |

TABLE 8a species specificity of selected lead candidates (mouse and rat VEGF 164)

| | Protein | mouse VEGF$_{164}$ | | | rat VEGF | | |
| --- | --- | --- | --- | --- | --- | --- | --- |
| ID | No. | ka (1/Ms) | kd (1/s) | KD (M) | ka (1/Ms) | kd (1/s) | KD (M) |
| 509-min | 854 | 6.14E+05 | 1.00E−03 | 1.63E−09 | 3.51E+05 | 8.44E−04 | 2.41E−09 |
| 509-max | 855 | 4.09E+06 | 5.90E−03 | 1.45E−09 | 3.90E+06 | 6.45E−03 | 1.65E−09 |
| 509-maxII | 856 | 3.47E+07 | 6.01E−02 | 1.73E−09 | 1.47E+07 | 2.66E−02 | 1.81E−09 |
| 511-min | 801 | 6.25E+05 | 1.03E−03 | 1.64E−09 | 5.50E+05 | 1.12E−03 | 2.04E−09 |
| 511-max | 802 | 7.53E+05 | 4.61E−05 | 6.13E−11 | 6.26E+05 | 6.63E−05 | 1.06E−10 |
| 567-min | 884 | 2.06E+06 | 3.50E−04 | 1.70E−10 | 1.72E+06 | 4.80E−04 | 2.79E−10 |
| 567-max | 874 | 1.64E+06 | 1.52E−04 | 9.29E−11 | 1.36E+06 | 2.03E−04 | 1.49E−10 |
| 578-min | 820 | 1.40E+06 | 1.51E−02 | 1.07E−08 | 1.70E+06 | 1.82E−02 | 1.07E−08 |
| 578-max | 821 | 1.03E+06 | 4.40E−04 | 4.29E−10 | 8.83E+05 | 5.28E−04 | 5.98E−10 |

TABLE 8b species specificity of selected development candidates

| | | Biacore measurements | | | Relative values Mouse VEGF$_{164}$ | |
| --- | --- | --- | --- | --- | --- | --- |
| | Protein | mouse VEGF$_{164}$ | | | (kd | (Kd$_{hVEGF165}$/ |
| ID | No. | ka (1/Ms) | kd (1/s) | KD (M) | h$_{VEGF165}$/kd$_{mVEGF164}$) | Kd$_{mVEGF164}$) |
| 578minmax | 903 | 1.14E+06 | 6.57E−04 | 5.67E−10 | 0.8 | 1.1 |
| 578 minmax_FW1.4:DHP | 961 | 1.10E+06 | 6.69E−04 | 6.08E−10 | 0.6 | 0.9 |
| 578minmaxT84N_V89L | 1008 | 1.23E+06 | 1.88E−03 | 1.53E−09 | 1.0 | 1.0 |
| 578min_max T84N_V89L_DHP | 1017 | 1.47E+06 | 2.16E−03 | 1.46E−09 | 1.4 | 1.8 |

| | | Biacore measurements | | | Relative values Mouse VEGF$_{164}$ | |
| --- | --- | --- | --- | --- | --- | --- |
| | Protein | rat VEGF$_{164}$ | | | (kd | (Kd$_{hVEGF165}$/ |
| ID | No. | ka (1/Ms) | kd (1/s) | KD (M) | h$_{VEGF165}$/kd$_{mVEGF164}$) | Kd$_{mVEGF164}$) |
| 578minmax | 903 | 8.58E+05 | 6.41E−04 | 7.48E−10 | 0.8 | 0.8 |
| 578 minmax_FW1.4:DHP | 961 | 8.00E+05 | 6.76E−04 | 8.45E−10 | 0.6 | 0.7 |
| 578minmaxT84N_V89L | 1008 | 8.02E+05 | 1.52E−03 | 1.89E−09 | 1.2 | 0.8 |

TABLE 8b-continued species specificity of selected development candidates

| | | | | | | |
|---|---|---|---|---|---|---|
| 578min_max T84N_V89L_DHP | 1017 | 1.04E+05 | 1.90E-03 | 1.82E-09 | 1.6 | 1.5 |

TABLE 9

Binding of selected lead candidates to VEGF isoforms (human VEGF121 and hVEGF110)

| Protein | | hVEGF$_{165}$ | | | hVEGF$_{110}$ | | |
|---|---|---|---|---|---|---|---|
| ID | Nr. | ka (1/Ms) | kd (1/s) | KD (M) | ka (1/Ms) | kd (1/s) | KD (M) |
| 509-min | 854 | 6.23E+05 | 1.14E-03 | 1.82E-09 | 2.87E+05 | 4.74E-04 | 1.65E-09 |
| 509-max | 855 | 2.26E+06 | 2.72E-03 | 1.21E-09 | 6.48E+05 | 2.35E-04 | 3.63E-10 |
| 509-maxII | 856 | 8.38E+05 | 2.82E-03 | 3.37E-09 | 9.01E+05 | 1.33E-03 | 1.48E-09 |
| 511-min | 801 | 5.05E+05 | 1.28E-03 | 2.53E-09 | 6.19E+05 | 8.98E-04 | 1.45E-09 |
| 511-max | 802 | 6.59E+05 | 4.40E-05 | 6.67E-11 | 4.05E+05 | 7.96E-05 | 1.97E-10 |
| 567-min | 884 | 2.01E+06 | 4.61E-04 | 2.30E-10 | 1.52E+06 | 3.82E-05 | 2.51E-11 |
| 567-max | 874 | 1.20E+06 | 2.26E-04 | 1.88E-10 | 1.00E+06 | 3.27E-05 | 3.27E-11 |
| 578-min | 820 | 1.14E+06 | 1.03E-02 | 9.01E-09 | 9.15E+05 | 1.04E-02 | 1.14E-08 |
| 578-max | 821 | 7.00E+05 | 3.07E-04 | 4.39E-10 | 5.23E+05 | 7.22E-04 | 1.38E-09 |

| | hVEGF$_{121}$ | | | |
|---|---|---|---|---|
| ID | ka (1/Ms) | kd (1/s) | KD (M) | PlGF |
| 509-min | 3.54E+05 | 4.53E-04 | 1.28E-09 | no binding |
| 509-max | 7.42E+05 | 2.49E-04 | 3.35E-10 | no binding |
| 509-maxII | 8.97E+05 | 1.23E-03 | 1.37E-09 | no binding |
| 511-min | 7.78E+05 | 9.63E-04 | 1.24E-09 | no binding |
| 511-max | 4.67E+05 | 9.97E-05 | 2.14E-10 | no binding |
| 567-min | 1.89E+06 | 4.54E-05 | 2.41E-11 | no binding |
| 567-max | 1.13E+06 | 5.76E-05 | 5.11E-11 | no binding |
| 578-min | 9.61E+05 | 8.80E-03 | 9.16E-09 | no binding |
| 578-max | 5.87E+05 | 5.58E-04 | 9.50E-10 | no binding |

TABLE 10

Overview on affinity and potency of lead derivatives (578 and 511)

| ID | Protein Nr. | Rel. activity hVEGR2 comp. ELISA (EC50$_{Luc}$ [nM]/ EC50$_{test}$ [nM]) | Rel. activity in HUVEC assay (EC50$_{Luc}$ [M]/ EC50$_{test}$ [nM]) hVEGF | Biacore Measurements hVEGF$_{165}$ | | |
|---|---|---|---|---|---|---|
| | | | | ka (1/Ms) | kd (1/s) | KD (M) |
| 578 wildtype C-His | 798 | ND | ND | 8.34E+05 | 1.69E-04 | 2.00E-10 |
| 578-min | 820 | 4.1 | 0.1001 | 1.14E+06 | 1.03E-02 | 9.01E-09 |
| 578-max | 821 | 9.6 | 0.94/1.0/1.2/1.2 (new setup) | 7.00E+05 | 3.07E-04 | 4.39E-10 |
| 578-max FW1.4_DHP | 960 | ND | ND | 9.30E+05 | 2.48E-04 | 2.66E-10 |
| 578-minmax | 903 | 8.4 | 1.6/1.4 (new setup) | 8.06E+05 | 5.04E-04 | 6.25E-10 |
| 578-minmax FW1.4_DHP | 961 | 16.5 | 0.78/1.9 | 7.11E+05 | 4.09E-04 | 5.76E-10 |
| 578-max-min | 902 | 6.5 | ND | 1.35E+06 | 8.83E-03 | 6.55E-09 |
| 578min_max T84N | 991 | ND | ND | 7.21E+05 | 7.00E-04 | 9.71E-10 |
| 578min_max V89A | 978 | ND | ND | 5.09E+05 | 6.12E-04 | 1.20E-09 |
| 578min_max V89L | 980 | ND | ND | 8.75E+05 | 1.87E-03 | 2.13E-09 |
| 578min_max T84N_V89L | 1008 | 8.4 | ND | 1.13E+06 | 1.80E-03 | 1.59E-09 |
| 578min_max T84N_V89A | 1009 | 7.5 | ND | 8.01E+05 | 4.93E-04 | 6.15E-10 |
| 578min_max T84N_V89L_DHP | 1017 | ND | ND | ND | ND | ND |

TABLE 10-continued

Overview on affinity and potency of lead derivatives (578 and 511)

| ID | Protein Nr. | Rel. activity hVEGR2 comp. ELISA (EC50$_{Luc}$ [nM]/ EC50$_{test}$ [nM]) | Rel. activity in HUVEC assay (EC50$_{Luc}$ [M]/ EC50$_{test}$ [nM]) hVEGF | Biacore Measurements hVEGF$_{165}$ | | |
|---|---|---|---|---|---|---|
| | | | | ka (1/Ms) | kd (1/s) | KD (M) |
| 578min_max T84N_V89A_DHP | | ND | ND | ND | ND | ND |
| 578max synth FW opt | 950 | ND | ND | 1.35E+06 | 5.86E−04 | 4.33E−10 |
| 578min_max_synthFW | 997 | 7.2 | ND | 1.23E+06 | 9.89E−04 | 8.03E−10 |
| 578max_min_synthFW | 990 | ND | ND | 1.55E+06 | 5.31E−03 | 3.42E−09 |
| 578min_max_FW1.synth | 1016 | ND | ND | 7.08E+05 | 7.02E−04 | 9.91E−10 |
| 511-min | 801 | 4.9 | 0.0011 | 5.05E+05 | 1.28E−03 | 2.53E−09 |
| 511-max | 802 | 8.7 | 0.0179 | 6.59E+05 | 4.40E−05 | 6.67E−11 |
| 511min_max | 904 | 5.4 | ND | 3.66E+05 | 1.02E−04 | 2.78E−10 |
| 511max_min | 905 | ND | ND | 5.11E+05 | 7.54E−04 | 1.48E−09 |

TABLE 11

Overview of biophysical characterization of lead derivatives (578 and 511)

| ID | Protein Nr. | TM in Bio-ATR [° C.] | % beta-sheet loss (Aquaspec 60° C.) | % Protein loss (precipitation at 60° C.) |
|---|---|---|---|---|
| 578-min | 820 | 66.85 | ND | ND |
| 578-max | 821 | 70.36 | −1.93% | 16.20% |
| 578-max FW1.4_DHP | 960 | ND | ND | ND |
| 578-minmax | 903 | 71.12 | −0.52% | 10.99% |
| 578minmax FW1.4_DHP | 961 | 70.18 | −0.15% | 14.82% |
| 578-max-min | 902 | ND | ND | ND |
| 578min_max T84N | 991 | 70.78 | 0.11% | 20.30% |
| 578min_max V89A | 978 | 63.23 | −2.28% | 48.22% |
| 578min_max V89L | 980 | 68.15 | −0.79% | 38.99% |
| 578min_max T84N_V89L | 1008 | 69 | −0.80% | 28.30% |
| 578min_max T84N_V89A | 1009 | ND | ND | ND |
| 578min_max T84N_V89L_DHP | 1017 | 67.8 | ND | ND |
| 578min_max T84N_V89A_DHP | 1080 | 66.3 | ND | ND |
| 578max synth FW opt | 950 | 63.62 | 54.06% | 97.85% |
| 578min_max_synthFW | 997 | 63.25 | 50.89% | 98.02% |
| 578max_min_synthFW | 990 | ND | ND | ND |
| 578min_max_FW1. synth | 1016 | 65.7 | −0.20% | 21.30% |
| 511-min | 801 | ND | ND | ND |
| 511-max | 802 | 70.5 | −1.53% | 4.50% |
| 511min_max | 904 | ND | ND | ND |
| 511max_min | 905 | ND | ND | ND |
| 567min | 884 | 54 | 100.00% | 100.00% |

| ID | Solubility by ammonium sulfate precipitation [EC$_{50}$ in % of NH$_4$(SO$_4$)$_2$ saturation] | Production: Refolding yield [mg/L] | Expression level in E. coli [arbitrary units] |
|---|---|---|---|
| 578-min | ND | 1.5 | ++ |
| 578-max | 27.24 | 12.5 | + |
| 578-max FW1.4_DHP | ND | 11.6 | + |
| 578-minmax | 28.13 | 23.93 | +++ |
| 578minmax FW1.4_DHP | 32.36 | 50.5 | +++ |
| 578-max-min | ND | 4.5 | + |
| 578min_max T84N | ND | 7.5 | +++ |
| 578min_max V89A | ND | 16 | +++ |
| 578min_max V89L | ND | 30 | +++ |
| 578min_max T84N_V89L | 27.88 | 24 | +++ |
| 578min_max | ND | 22 | +++ |

TABLE 11-continued

Overview of biophysical characterization of lead derivatives (578 and 511)

| | | | |
|---|---|---|---|
| T84N_V89A | | | |
| 578min_max | 30.80 | 36 | +++ |
| T84N_V89L_DHP | | | |
| 578min_max | 30.70 | 30 | +++ |
| T84N_V89A_DHP | | | |
| 578max synth FW opt | 28.30 | 19.4 | ++ |
| 578min_max_synthFW | 30.05 | 24 | +++ |
| 578max_min_synthFW | ND | 0.5 | ++ |
| 578min_max_FW1. synth | 25.10 | 28 | +++ |
| 511-min | ND | 13.5 | +++ |
| 511-max | 8.62 | 6.47 | +++ |
| 511min_max | ND | 3.75 | +++ |
| 511max_min | ND | 7 | +++ |
| 567min | 20.70 | 16.5 | +++ |

Some derivatives, as listed in FIG. 6, were compared for their denaturation and precipitation after thermal stress (e.g., under 50° C., 60° C., or 70° C.) for 30 minutes. 578max, 578minmax and 578minmax_DHP were further exemplified for their solubility, which was determined by ammonium sulfate precipitation. As in FIG. 7, the percentage of soluble proteins of these derivatives under various concentrations of ammonium sulfate were compared.

TABLE 12a anti-VEGF binders after incubation for 30 min at 50° C.

| Sample name | Beta sheet % | Nanodrop (mg/ml) |
|---|---|---|
| 950 | 100.8 | 81.2 |
| 978 | 100.9 | 85.1 |
| 980 | 99.9 | 100.3 |
| 991 | 99.4 | 99.2 |
| 802 | 100.4 | 96.7 |
| 821 | 100.6 | 93.5 |
| 903 | 99.5 | 99.4 |
| 961 | 98.7 | 101.7 |
| 997 | 99.9 | 76.39 |

TABLE 12a anti-VEGF binders after incubation for 30 min at 60° C.

| Sample name | Beta sheet % | Nanodrop (mg/ml) |
|---|---|---|
| 950 | 45.9 | 2 |
| 978 | 102.3 | 52 |
| 980 | 100.8 | 61 |
| 991 | 99.9 | 80 |
| 802 | 101.5 | 96 |
| 821 | 101.9 | 84 |
| 903 | 100.5 | 89 |
| 961 | 100.1 | 85 |
| 997 | 49.1 | 2 |

TABLE 12a anti-VEGF binders after incubation for 30 min at 70° C.

| Sample name | Beta sheet % | Nanodrop (mg/ml) |
|---|---|---|
| 950 | 43.1 | 1.0 |
| 978 | 13.4 | 2.7 |
| 980 | 4.5 | 0.2 |
| 991 | 21.5 | 1.4 |
| 802 | 100.4 | 80.8 |
| 821 | 58.4 | 3.3 |
| 903 | 81.9 | 0.7 |
| 961 | 46.3 | 1.1 |
| 997 | 0.0 | 0.3 |

EXAMPLE 4

VEFG Receptor Blocking Assays

For anti-VEGF scFv candidates or their derivatives disclosed in the present invention, their potency as VEGF inhibitors was also measured besides their binding affinity to VEGFs in Example 3. The methods to measure their potency include, for example, the VEGFR competition ELISA, as exemplified in this example, and HUVEC assays (FIG. 8).

The VEGFR competition ELISA assays include, for example, VEGFR2 Receptor blocking assays and VEGFR1 Receptor blocking assays. For VEGFR2 Receptor blocking assay, human $VEGF_{165}$ was coated on a 96-well Maxisorp ELISA plate (Nunc) at 0.05 µg/ml in PBS and blocked using PBS with 0.1% BSA and 0.2% Tween 20 (PBST). 500 ng/ml recombinant human VEGFR2/Fc chimera (R&D Systems Inc.), consisting of amino acid residues 1-764 of the extracellular domain of human VEGFR2 fused to a 6× histidine tagged Fc of human $IgG_1$, was first incubated with 3-fold serially diluted anti-VEGF scFvs in PBST. After 30-60 min of incubation at room temperature, the mixtures were transferred to the human $VEGF_{165}$ immobilized plate and incubated for 90 min. Binding of the VEGFR2/Fc chimera to the immobilized $VEGF_{165}$ was detected with goat ($Fab_2$) anti-human IgG Fcγ coupled to horseradish peroxidase (Jackson ImmunoResearch) followed by substrate (BM Blue POD substrate, Roche Diagnostics). Optical density at 450 nm (OD 450 nm) was measured using a Sunrise microplate reader (Tecan). Data were analyzed using a 4-parameter logistic curve fit, and $EC_{50}$ values were calculated from the dose-response curves of the scFvs. The exemplary potency of lead candidates or their derivatives, measured by VEGFR2 Receptor blocking assay, is listed in Table 7 and 9.

For VEGFR1 Receptor blocking assay, human $VEGF_{165}$ was coated on a 96-well Maxisorp ELISA plate (Nunc) at 0.0125 µg/ml in PBS and blocked using PBS with 0.4% BSA and 0.1% Tween 20. 100 ng/ml of recombinant human VEGFR1/Fc chimera (R&D Systems Inc.), consisting of amino acid residues 1-687 of the extracellular domain of human VEGFR1 fused to a 6× histidine tagged Fc of human $IgG_1$, was first incubated with 3-fold serially diluted anti- VEGF scFvs in PBST. After 30-60 min of incubation at room temperature, the mixtures were transferred to the human $VEGF_{165}$ immobilized plate and incubated for 90 min. Binding of the VEGFR1/Fc chimera to the immobilized $VEGF_{165}$ was detected with goat (Fab) anti-human IgG Fcγ coupled to horseradish peroxidase (Jackson ImmunoResearch) followed by substrate (BM Blue POD substrate, Roche Diagnostics). Optical density at 450 nm (OD 450 nm) was measured using a Sunrise microplate reader (Tecan). Data were analyzed as above, and $EC_{50}$ values were calculated from the dose-response curves of the scFvs. The exemplary potency of lead candidates, measured by VEGFR1 Receptor blocking assay, is listed in Table 7.

EXAMPLE 5

HUVEC Assay of VEGF Inhibition

This example exemplifies HUVEC assays as another method to measure the potency of the disclosed anti-VEGF scFv candidates, or their derivatives, as VEGF inhibitors.

Human umbilical vein endothelial cells (HUVECs) (Promocell), pooled from several donors, were used at passage 2 to passage 14. Cells were seeded at 1000 cells/well in 50 µl complete endothelial cell growth medium (ECGM) (Promocell), that contained 0.4% ECGS/H, 2% Fetal Calf Serum, 0.1 ng/ml Epidermal Growth Factor, 1 µg/ml Hydrocortison, 1 ng/ml basic Fibroblast Factor and 1% penicillin/streptomycin (Gibco). 7 to 8 h later, 50 µl starving medium (ECGM without supplements containing 0.5% heat inactivated FCS and 1% penicillin/streptomycin) was added to the cells and the cells were starved for 15 to 16 hours. 3 fold Serial dilutions of anti-VEGF scFvs (0.023-150 nM) and one of the following—recombinant human $VEGF_{165}$ (0.08 nM), recombinant mouse $VEGF_{164}$ (0.08 nM), or recombinant rat $VEGF_{164}$ (0.3 nM)-were prepared in starving medium and preincubated for 30-60 min at room temperature. The different concentrations of VEGFs were used to compensate for their different relative biological activities. Concentrations that stimulate submaximal VEGF induced proliferation ($EC_{90}$) were used. 100 µl of the mixtures were added to the 96-well tissue-culture plates containing the HUVEC suspension and incubated for 4 days in a 37° C./5% $CO_2$ humified incubator. Proliferation of HUVECs was assessed by measuring absorbance at 450 nm (620 nm used as reference wavelength) after addition of 20 µl/well WST-1 cell proliferation reagent (Roche) using a Sunrise microplate reader (Tecan). Data were analyzed using a 4-parameter logistic curve-fit, and the concentration of anti-VEGF scFvs required to inhibit HUVEC proliferation by 50% ($EC_{50}$) was derived from inhibition curves.

Figure 9:
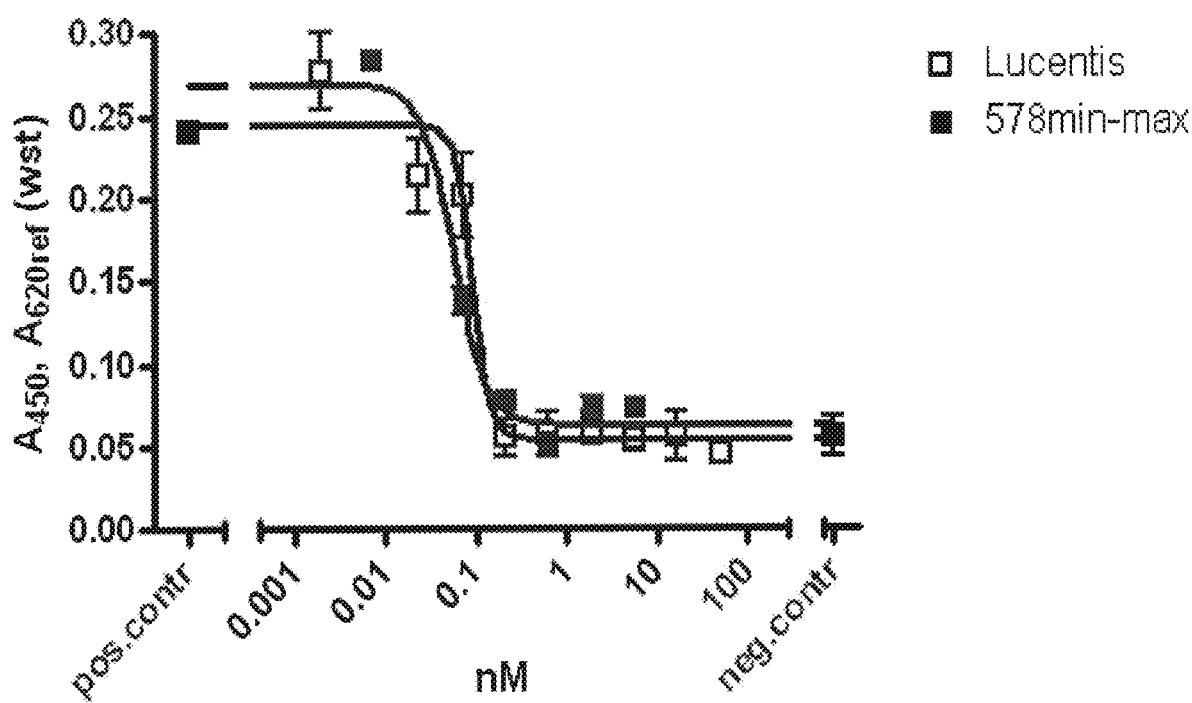
FIG. 9 illustrates the effects of 578minmax on HUVEC proliferation induced by hVEGF165. The parameters of the assay were the following: hVEGF165 concentration: 0.08 nM (3ng/ml); incubation with VEGF and test item: 96h. The EC50 was 0.08959 nM for Lucentis and 0.05516 nM for 578minmax, whereas the $R^2$ was 0.9066 for Lucentis and 0.9622 for 578minmax.
Figure 10A:
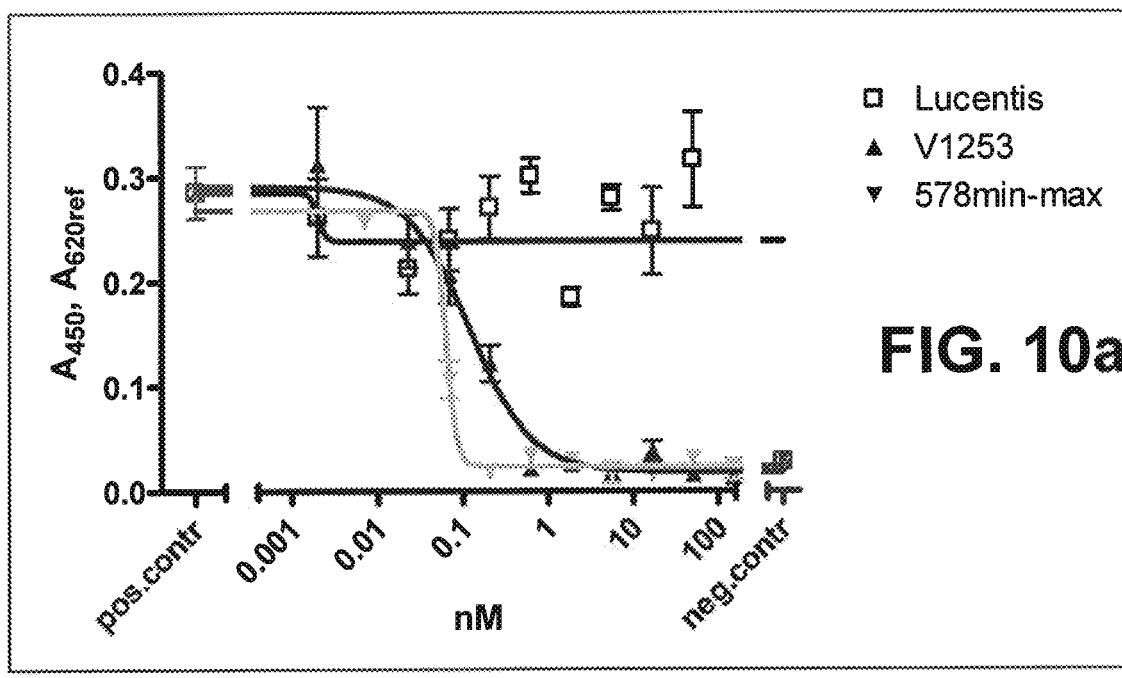
FIGS. 10*a* and 10*b* illustrate the effects of 578minmax on HUVEC Proliferation induced by mouse VEGF164 and rat VEGF164. The parameters of the assay were the following: mouse VEGF164 concentration: 0.08 nM (3ng/ml); rat VEGF164 concentration: 0.3 nM (11.3 ng/ml). Both concentrations were selected at EC90 for VEGF induced HUVEC proliferation; incubation with VEGF and test item: 96h.
Figure 10B:
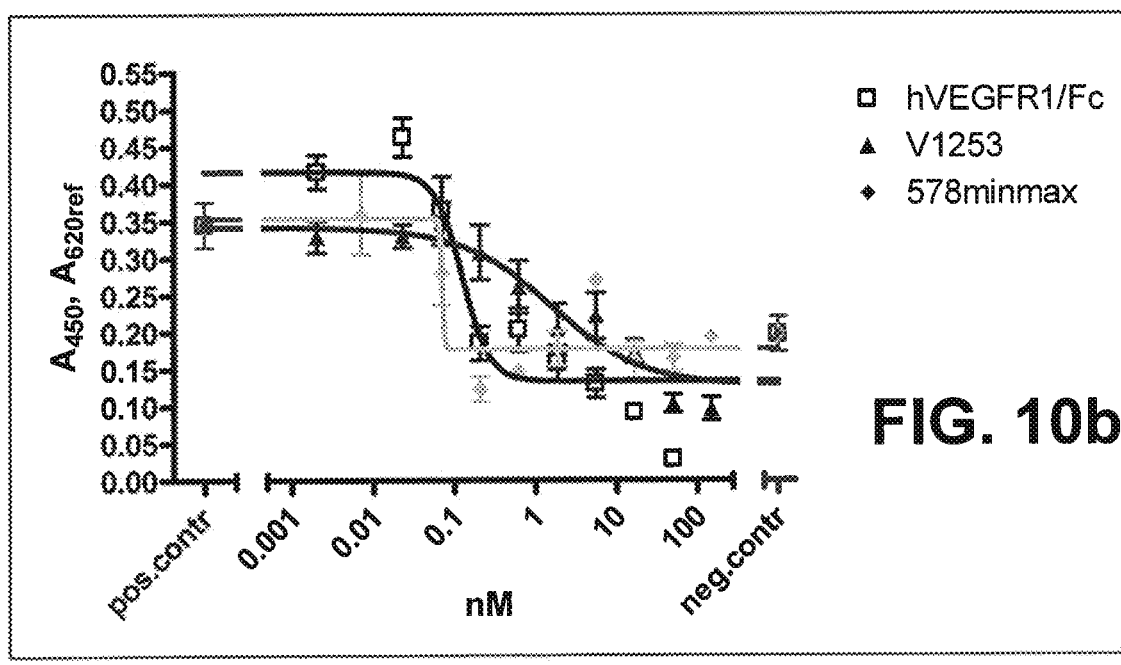

The exemplary potency of lead candidates or their derivatives, measured by HUVEC assays, is listed in Table 7. Further, the inhibition of $hVEGF_{165}$-induced HUVEC proliferation by one derivative of lead candidates, 578minmax, is exemplified in FIG. 9. EC50 of 578minmax for inhibition of $hVEGF_{165}$-induced cell-proliferation is determined to be 0.06 nM (FIG. 9). The potency of 578minmax as a VEGF inhibitor is about 1.6 times better compared to Lucentis. The inhibition of mouse or rat $VEGF_{164}$-induced HUVEC proliferation by 578minmax is also exemplified in FIG. 10. EC50 of 578minmax for inhibition of mouse and rat $VEGF_{164}$ induced cell-proliferation is 0.06 nM and 0.07 nM, respectively (FIG. 10). Thus, mouse and rat VEGF are equipotent to human VEGF for being inhibited by the exemplary derivative (578minmax). Also in this experiment, Lucentis does not inhibit proliferation induced by rodent VEGF.

EXAMPLE 6

Effects of Anti-VEGF scFvs on $hVEGF_{165}$ Induced Vascular Permeability in Hairless Guinea Pigs In this example, the effect of anti-VEGF scFvs on human $VEGF_{165}$ induced vascular permeability was assessed in guinea pigs using the Miles assay. Thirty application sites per animal were marked on the dorsum of hairless male guinea pigs using a permanent marker. On the treatment day each animal was administered intravenously with 1 ml of a 1% Evans blue dye solution under general anesthesia. One hour after dye injection, 0.1 ml of test solution containing 2.61 nM recombinant human $VEGF_{165}$ (PeproTech EC Ltd.) and various concentrations of anti-VEGF scFvs (0 nM, 0.085 nM, 0.256 nM, 0.767 nM, 2.3 nM, 6.9 nM, 20.7 nM, 62.1 nM; n=7 animals per test item) was injected in triplicate into the marks on the dorsum (3 injections per concentration of test item). Injections of PBS served as a negative control in all animals. As an additional control, 6.9 nM Lucentis (Novartis) was injected in all animals.

One hour after injection of the test solutions, the animals were euthanized, and the pelts were collected, cleaned, and photographed digitally using incident and transmitted light. The area of Evans Blue dye that extravasated into the injection sites was evaluated using Image J. For each animal, anti-VEGF scFv concentration versus area of dye leakage was analyzed using a 4-parameter logistic curve fit. The concentration of anti-VEGF scFvs required to inhibit vascular leakage by 50% ($EC_{50}$) was derived from inhibition curves.

Figure 11:
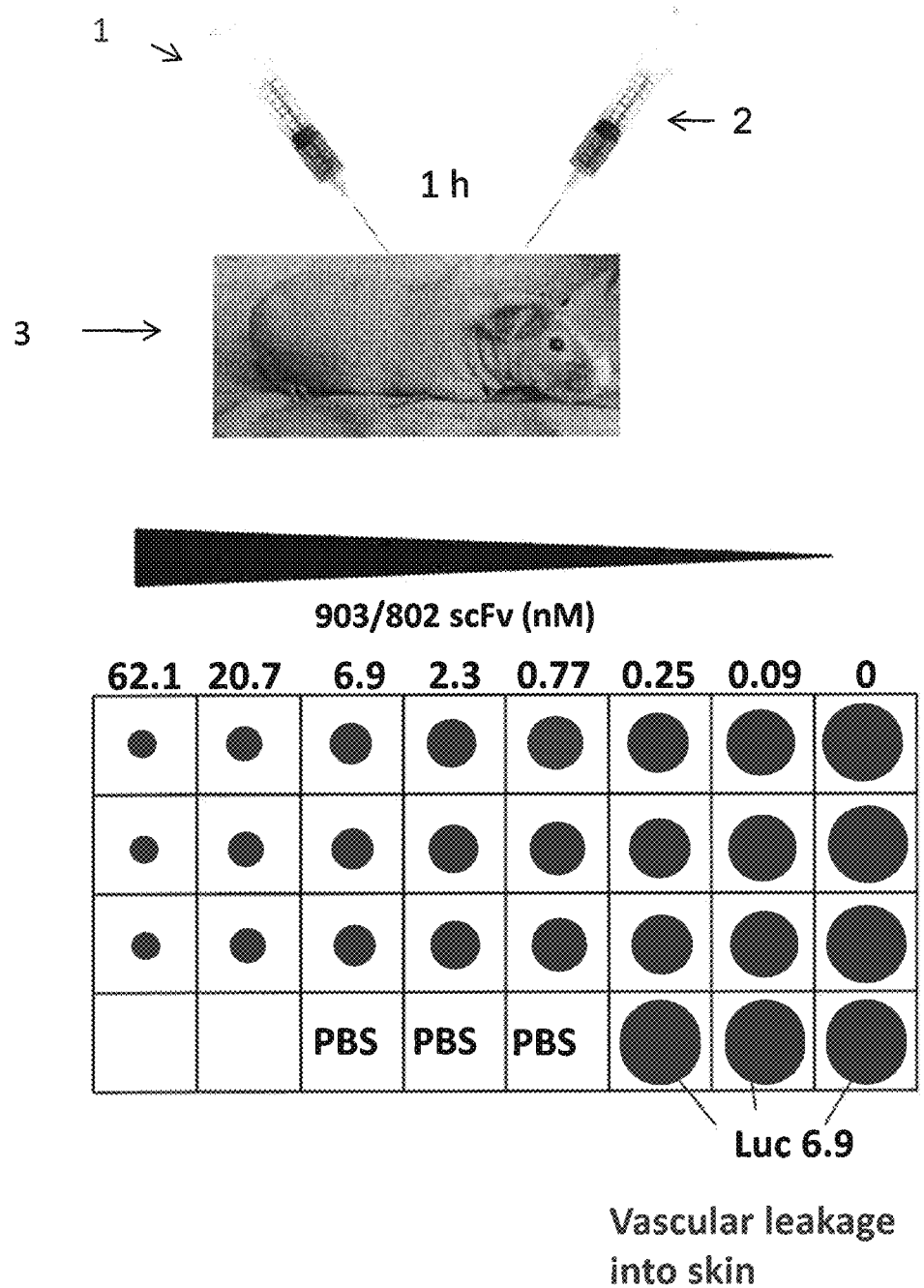
FIG. 11 illustrates efficacy studies using Miles assay in nude guinea pigs (part I). The dye almar blue 1 was administered intravenously to nude guinea pigs. One hour after dye injection, a premixture 2 of hVEGF (2.61 nM) and Lucentis, ESBA903 or #802, respectively, was injected into the skin of the animal 3. One hour after injection of the solutions, the animals 3 were euthanized and the pelts were collected, cleaned and photographed digitally using incident and transmitted light. The area of Evans Blue dye that extravasated into the injection sites was evaluated using Image J and the dose-area retention was plotted.
Figure 12A:
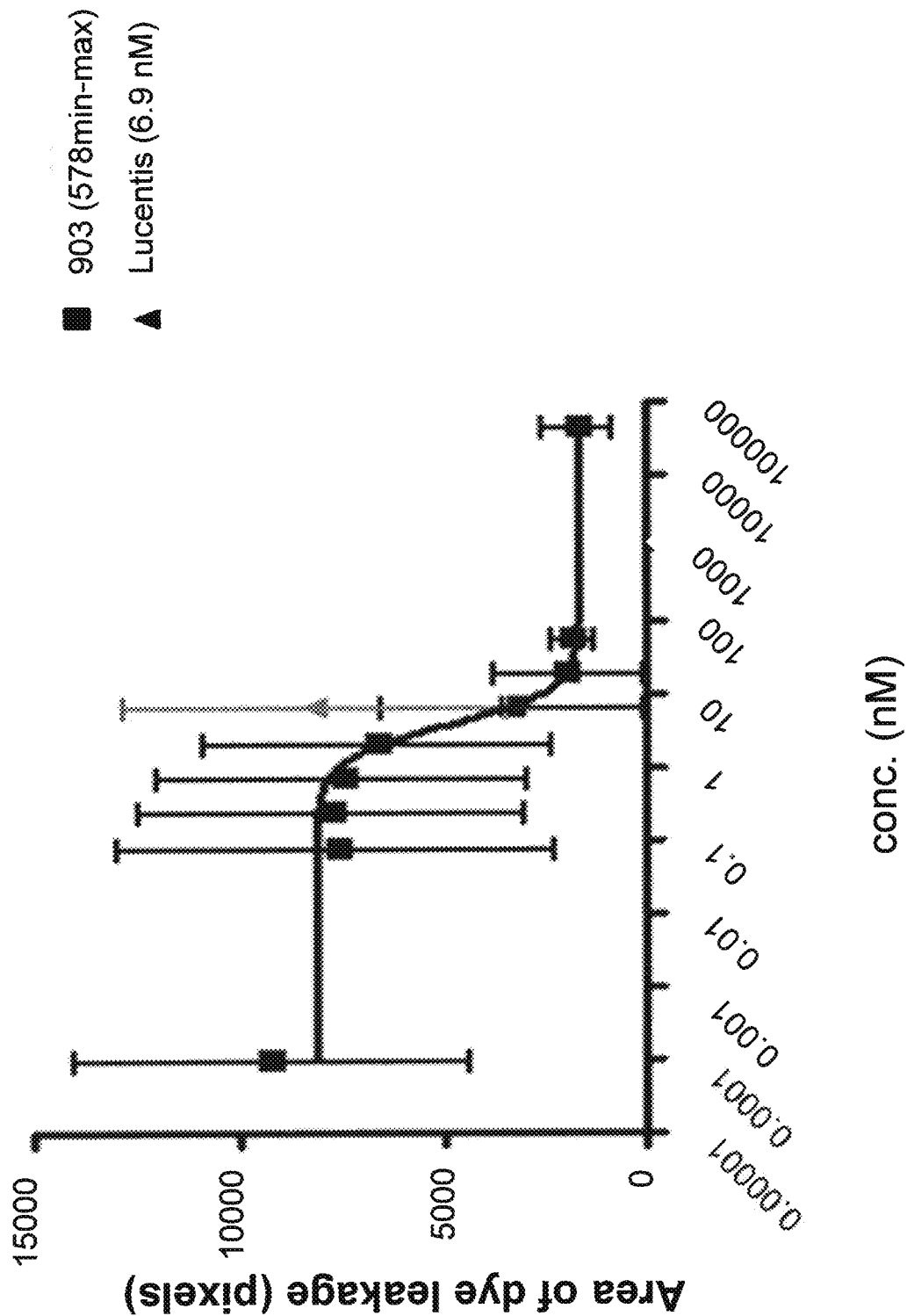
FIGS. 12*a*, 12*b* and 12*c* illustrate efficacy studies using Miles assay in nude guinea pigs (part II).
Figure 12B:
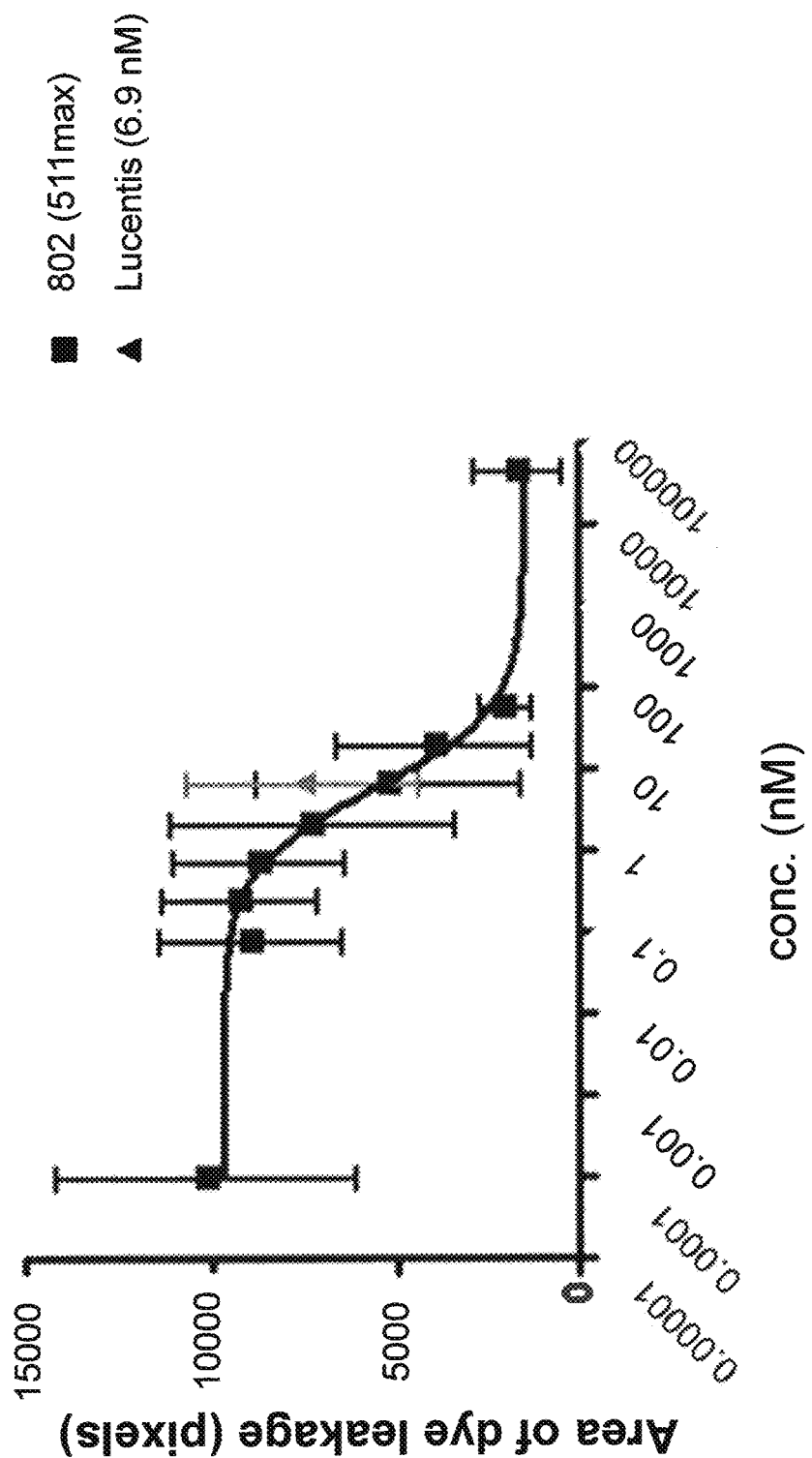
Figure 12C:
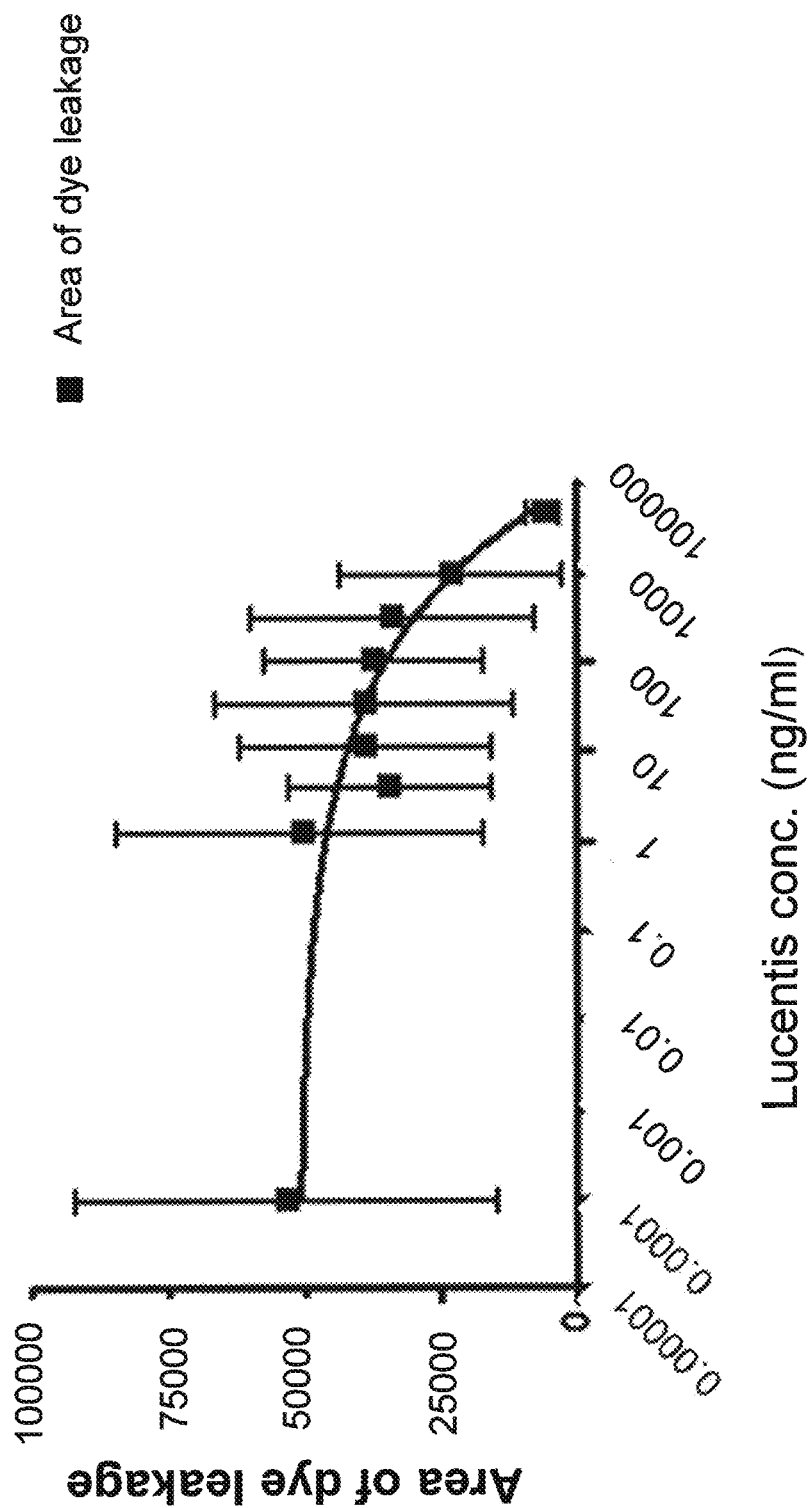

The experiment protocol is exemplified in FIG. 11. Also, the efficacy of scFv candidates, ESBA903 (578minmax) and 802 (511max), in inhibiting the hVEGF was illustrated in FIG. 11, represented by different sizes of areas containing the Evans Blue dye leaked from vascular system into skin. The efficacy data for 903 and 802 are shown in FIG. 12. At 6.9 nM, 903 and 802 showed stronger inhibition of VEGF induced vascular leakage into the skin compared to Lucentis in all animals tested (FIG. 12).

EXAMPLE 7

Effects of Topical Anti-VEGF scFvs Treatment on $hVEGF_{165}$ Induced Retinal Vascular Leakage in Rats In this example, topical efficacy of 578minmax is demonstarted using a modified Miles assay. These modifications include, for example, premixed study with intravitreal injections and topical application of scFvs.

Figure 13A:
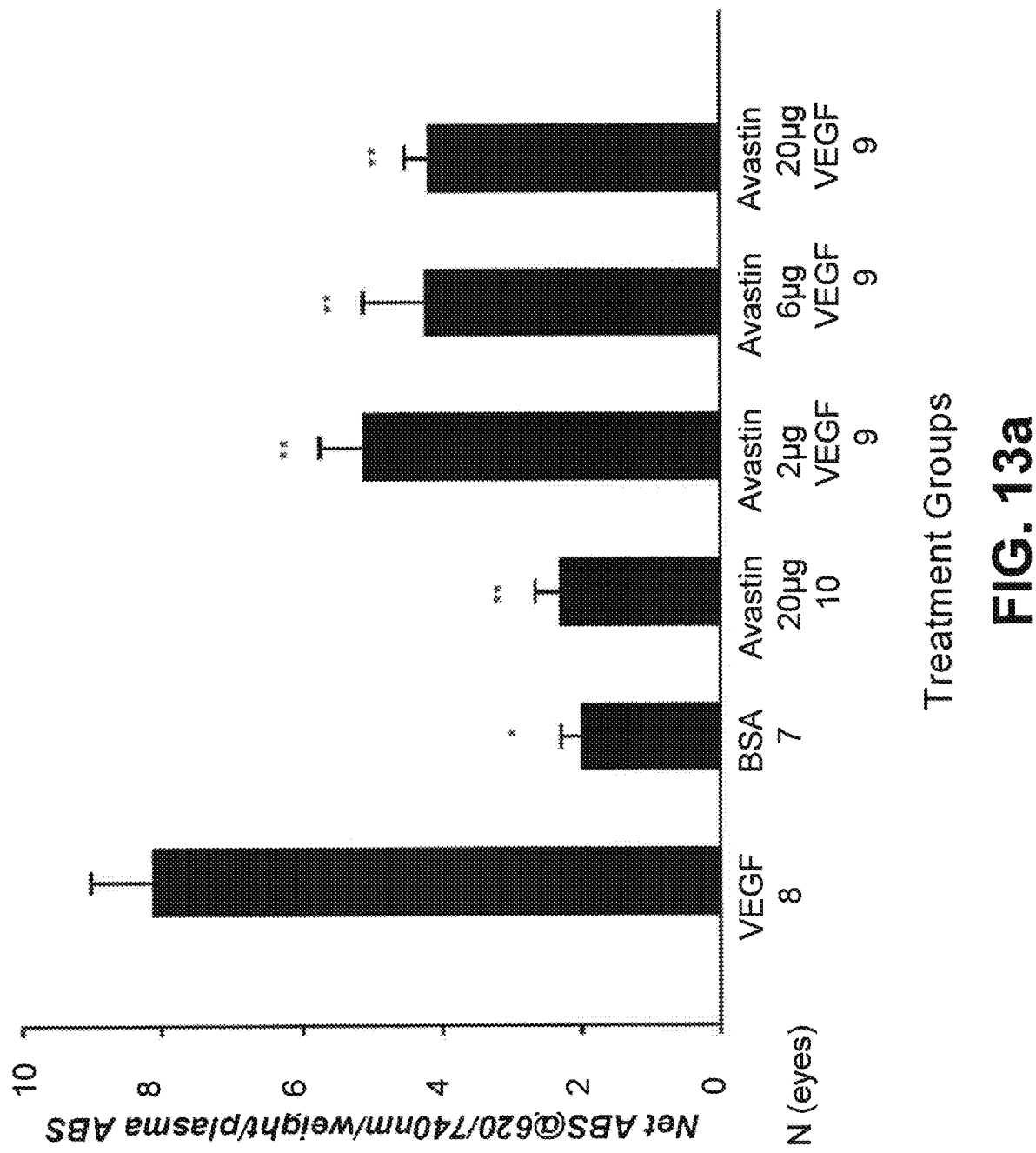
FIGS. 13*a* and 13*b* illustrate efficacy studies using modified miles assay in rats (premixed hVEGF165 and 578minmax (ESBA903)).
Figure 13B:
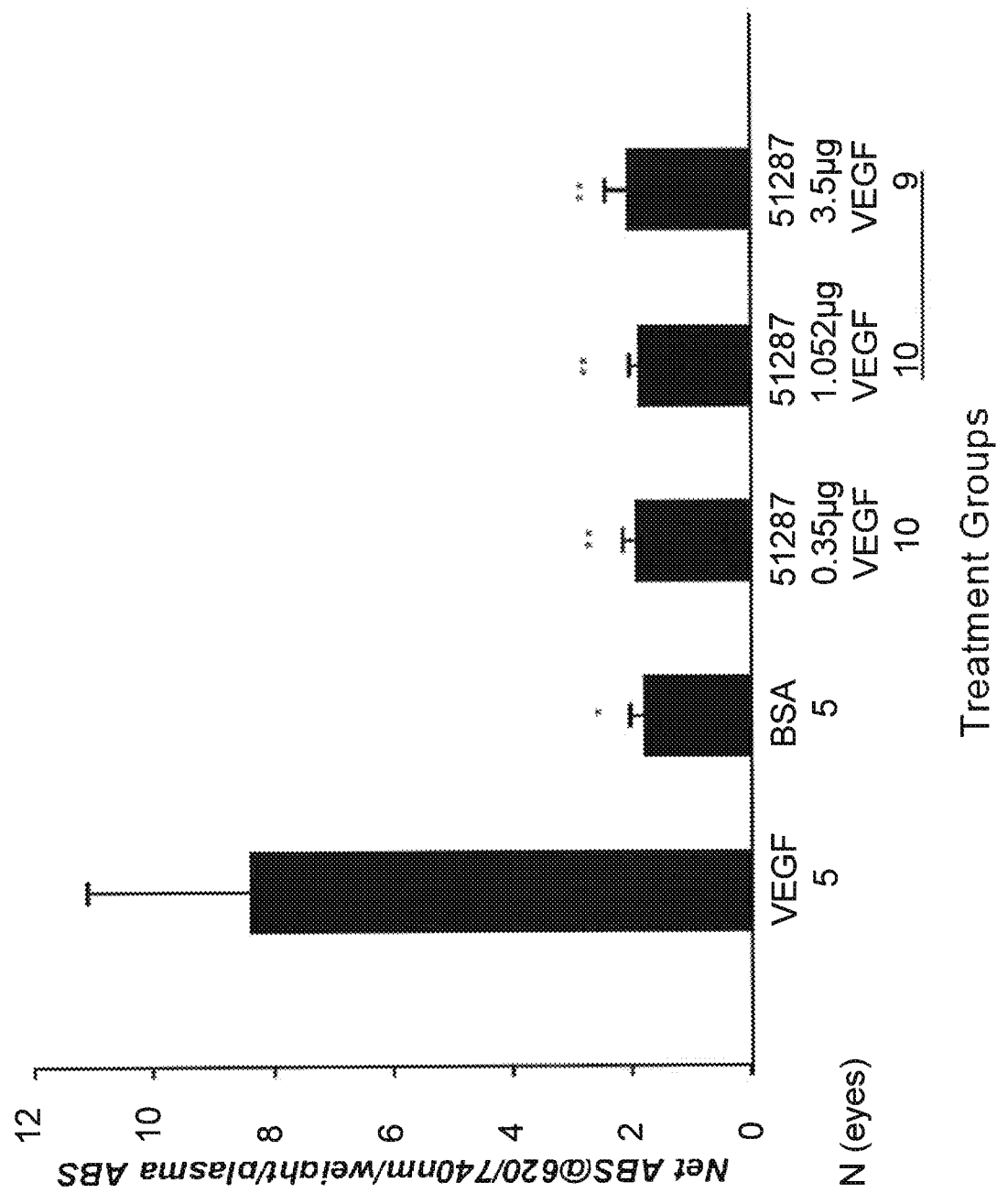

Premixed different concentrations of anti-VEGF scFv (10, 3, and 1 fold molar excess over VEGF) and VEGF (500 ng) were applied via a single intravitreal injection. Avastin (Roche) (10, 3, and 1 fold molar excess over VEGF) was used as a positive control. Vehicle for 578minmax (Citrate Buffer, 20 mM Na-Citrate, 125 mM NaCl, pH 7) was used as negative control. As illustrated in FIG. 13, premixing with $hVEGF_{165}$ facilitated 578minmax (ESBA903) to completely inhibit hVEGF-induced retinal vascular permeability. In this experiment, the inhibitory effect of 578minmax (ESBA903) was more significant compared to Avastin.

Figure 14:
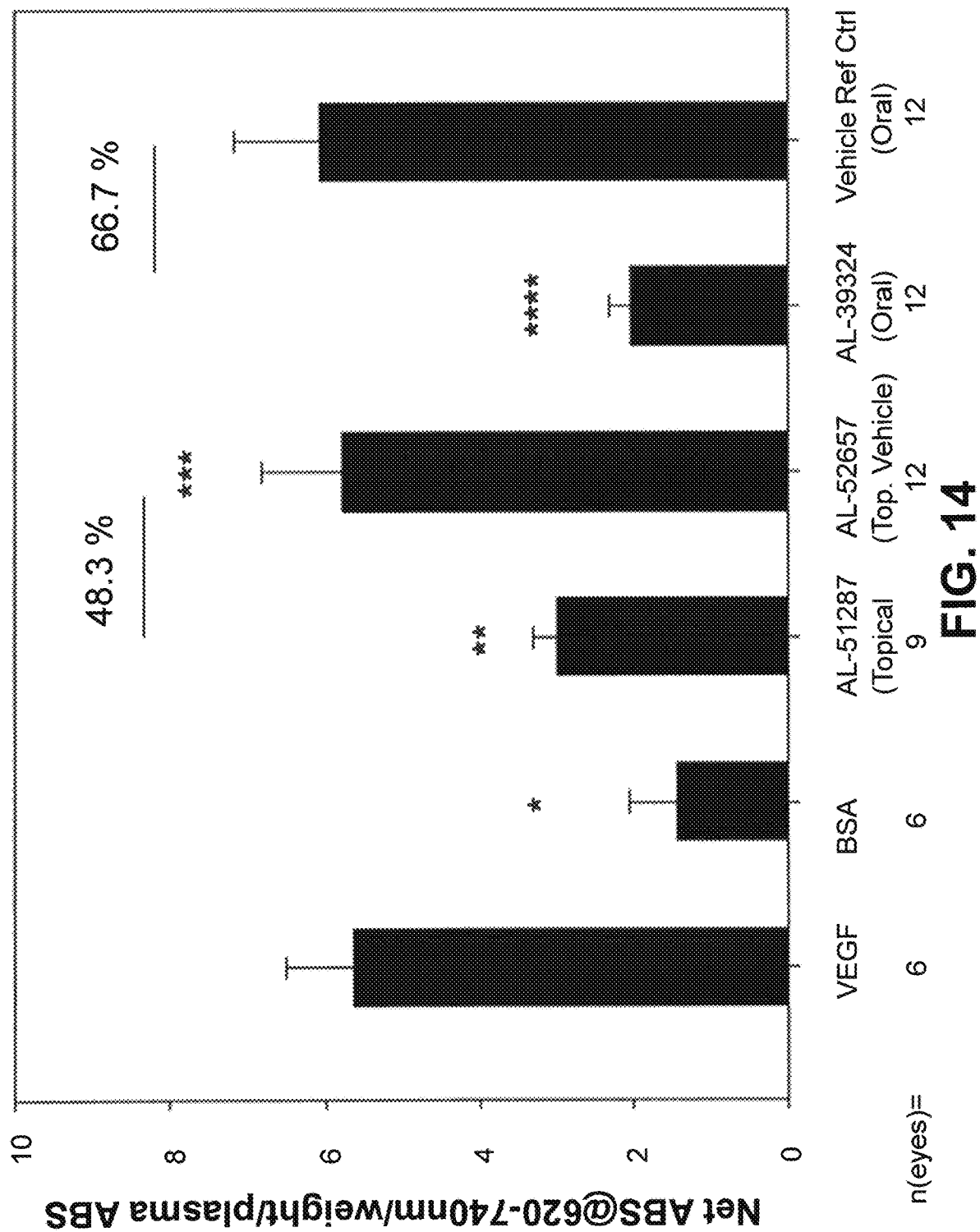
FIG. 14 illustrates efficacy studies using modified miles assay in rats (topical administration of 578minmax (ESBA903)). The anti-permeability efficacy of AL-51287 (ESBA903) upon VEGF induced retinal vascular leakage in rats was tested upon topical administration. Five days pre-treatment, 4 drops/day with a 10 ng/ml ESBA903 formulation. *$p<0.05$ (VEGF s. BSA), $p<0.05$ (VEGF vs. AL-51287), *$p=0,060$ (AL-51287 vs. AL-52667), **** (VEGF vs. AL-39324); $p<0.05$ (AL-39324 vs. vehicle ref ctrl). AL-51287: ESBA903; AL-52657: topical vehicle reference control; AL-39324: small molecule RTK inhibitor.

For topical application, five days before VEGF stimulation, adult Sprague-Dawley rats received 578minmax (1%=10 mg/ml) via bilateral topical dosing qid (4 drops/day) till perfusion day (Day 6). Vehicle for 578minmax (topical dosing) and Alcon RTKi (10 mg/kg/d, oral gavage) were used as negative and positive controls. On Day 5, rats are anesthetized and their pupils are dilated. All animals receive intravitreal injections of 500 ng hrVEGF (10 µl) in both eyes. Following 24 hours post-injection of VEGF, intravenous infusion of 3% Evans blue dye is performed on all animals during general anesthesia. After the dye has circulated for 90 minutes, the rats are euthanized. Blood samples are taken, then the rats are perfused with sterile saline solution, then both eyes of each rat are immediately enucleated and the retinas harvested using a surgical microscope. For both retina and plasma samples, 60 µL of supernatant is used to measure the Evans blue dye absorbance (ABS) with a spectrophotometer at 620/740 nm. The blood-retinal barrier breakdown and subsequent retinal vascular permeability as measured by dye absorbance are calculated as means±s.e.m. of net ABS/wet weight/plasma ABS. One way ANOVA is used to determine an overall difference between treatment means, where $P \leq 0.05$ is considered significant. As exemplified in FIG. 14, the topical administration (5 days of pretreatment, 4 drops per day) of 578minmax (903) significantly inhibited hVEGF-induced retinal vascular permeability. This is the first demonstration of a topically effective antibody useful for the treatment of intraocular disease.

Equivalents

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this specification, including defined terms, term usage, described techniques, or the like, this specification controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

```
SEQUENCE LISTING
SEQ ID NO: 1
Peptide Immunogen
KFMDVYQRSYC

VL sequences:
SEQ ID NO. 72: 60
EVVMAQTPASVEAAVGGTVTIKCQASQSISSYLSWYQQKPGQPPKLLIYKASTLASGVPSRFKGSRS

GTEYTLTISDLECADAATYYCQSNYGGSSSDYGNPFGGGTEAVVK

SEQ ID NO. 73: 435
AFELTQTPSSVEAAVGGTVTIKCQASQSIGSSLAWYQQKPGQRPKLLIYTAANLASGVPSRFRGSRSG

AAFTLTISDLECADAATYYCQNFATSDTVTFGGGTEVVVT

SEQ ID NO. 74: 453
AVVLTQTPSPVSAAVGGTVSISCQSSQSVWNNNRLAWFQQKSGQPPKLLIYYASTLASGVPSRFKG

SGSGTEFTLTISDVQCDDAATYYCAGGYSSTSDNTFGGGTEVVVK

SEQ ID NO. 75: 375
DIVMTQTPASVEATVGGTITINCQASENINIWLSWYQQKPGQPPKLLIYQASKLASGVPSRFKGSGS

GTQFTLTISDLECADAATYYCQNNYSYNRYGAPFGGGTEVVVK

SEQ ID NO. 76: 610
DVVMTQTPASVSEPVGGTVTIKCQASQSISSWLSWYQQKPGQPPKLLIYQASTLASGVPPRSSGSG

SGTEYTLTISDLECADAATYFCQNNYGFRSYGGAFGGGTEVVVK

SEQ ID NO. 77: 578
DVVMTQTPSSVSAAVGDTVTINCQASEIIHSWLAWYQQKPGQPPKLLIYLASTLASGVPSRFKGSGS

GTQFTLTISDLECADAAIYYCQNVYLASTNGANFGGGTEVVVK

SEQ ID NO. 78: 534
DVVMTQTPSSVSAAVGDTVTIKCQASQSINIWLSWYQQKSGQPPKLLVYKESTLASGVPSRFRGSG

SGTQFTLTISDLECADAATYYCQNNYDSGNNGFPFGGGTEVVVK
```

SEQ ID NO. 79: 567
DVVMTQTPSSVSAAVGDTVTINCQADQSIYIWLSWYQQKPGQPPKLLIYKASTLESGVPSRFKGSGS

GTQFTLTISDLECADAATYYCQNNAHYSTNGGTFGGGTEVVVK

SEQ ID NO. 80: 509
DVVMTQTPSSVSAAVGDTVTIKCQASQNIRIWLSWYQQKPGQPPKLLIYKASTLESGVPSRFKGSGS

GTEFTLTISDLECADAATYYCQNNAHYSTNGGTFGGGTEVVVK

SEQ ID NO. 81: 511
EVVMTQTPASVEAAVGGTVTIKCQASQSINIWCSWYQQKPGHPPKLLIYRASTLASGVSSRFKGSGS

GTEFTLTISDLECADAATYYCQANYAYSAGYGAAFGGGTEVVVK

SEQ ID NO. 82: 60 min
EIVMTQSPSTLSASVGDRVIITCQASQSISSYLSWYQQKPGKAPKLLIYKASTLASGVPSRFSGSGSGA

EFTLTISSLQPDDFATYYCQSNYGGSSSDYGNPFGQGTKLTVLG

SEQ ID NO. 83: 435 min
EIVMTQSPSTLSASVGDRVIITCQASQSIGSSLAWYQQKPGKAPKLLIYTAANLASGVPSRFSGSGSG

AEFTLTISSLQPDDFATYYCQNFATSDTVTFGQGTKLTVLG

SEQ ID NO. 84: 453 min
EIVMTQSPSTLSASVGDRVIITCQSSQSVWNNNRLAWYQQKPGKAPKLLIYYASTLASGVPSRFSGS

GSGAEFTLTISSLQPDDFATYYCAGGYSSTSDNTFGQGTKLTVLG

SEQ ID NO. 85: 375 min
EIVMTQSPSTLSASVGDRVIITCQASENINIWLSWYQQKPGKAPKLLIYQASKLASGVPSRFSGSGSG

AEFTLTISSLQPDDFATYYCQNNYSYNRYGAPFGQGTKLTVLG

SEQ ID NO. 86: 610 min
EIVMTQSPSTLSASVGDRVIITCQASQSISSWLSWYQQKPGKAPKLLIYQASTLASGVPSRFSGSGSG

AEFTLTISSLQPDDFATYYCQNNYGFRSYGGAFGQGTKLTVLG

SEQ ID NO. 87: 578 min
EIVMTQSPSTLSASVGDRVIITCQASEIIHSWLAWYQQKPGKAPKLLIYLASTLASGVPSRFSGSGSGA

EFTLTISSLQPDDFATYYCQNVYLASTNGANFGQGTKLTVLG

SEQ ID NO. 88: 534 min
EIVMTQSPSTLSASVGDRVIITCQASQSINIWLSWYQQKPGKAPKLLIYKESTLASGVPSRFSGSGSGA

EFTLTISSLQPDDFATYYCQNNYDSGNNGFPFGQGTKLTVLG

SEQ ID NO. 89: 567 min
EIVMTQSPSTLSASVGDRVIITCQADQSIYIWLSWYQQKPGKAPKLLIYKASTLESGVPSRFSGSGSGA

EFTLTISSLQPDDFATYYCQNNAHYSTNGGTFGQGTKLTVLG

SEQ ID NO. 90: 509 min
EIVMTQSPSTLSASVGDRVIITCQASQNIRIWLSWYQQKPGKAPKLLIYKASTLESGVPSRFSGSGSG

AEFTLTISSLQPDDFATYYCQNNAHYSTNGGTFGQGTKLTVLG

SEQ ID NO. 91: 511 min
EIVMTQSPSTLSASVGDRVIITCQASQSINIWCSWYQQKPGKAPKLLIYRASTLASGVPSRFSGSGSG

AEFTLTISSLQPDDFATYYCQANYAYSAGYGAAFGQGTKLTVLG

SEQ ID NO. 92: 578 min_Pref subst
EIVLTQSPSSLSASVGDRVTITCQASEIIHSWLAWYQQRPGKAPKLLISLASTLASGVPSRFSGSGSGT

DFTFTISSLQPEDFAVYYCQNVYLASTNGANFGQGTKVEIKR

SEQ ID NO. 93: 60 max
EIVMTQSPSTLSASVGDRVIITCQASQSISSYLSWYQQKPGKAPKLLIYKASTLASGVPSRFSGSGSGT

EFTLTISSLQPDDFATYYCQSNYGGSSSDYGNPFGQGTKLTVLG

SEQ ID NO. 94: 435 max
EIVMTQSPSTLSASVGDRVIIKCQASQSIGSSLAWYQQKPGKAPKLLIYTAANLASGVPSRFSGSGSG

AEFTLTISSLQPDDFATYYCQNFATSDTVTFGQGTKLTVLG

-continued

SEQ ID NO. 95: 453 max
EIVMTQSPSTLSASVGDRVIITCQSSQSVWNNNRLAWYQQKPGKAPKLLIYYASTLASGVPSRFSGS

GSGTEFTLTISSLQPDDFATYYCAGGYSSTSDNTFGQGTKLTVLG

SEQ ID NO. 96: 375 max
EIVMTQSPSTLSASVGDRVIITCQASENINIWLSWYQQKPGKAPKLLIYQASKLASGVPSRFSGSGSG

TQFTLTISSLQPDDFATYYCQNNYSYNRYGAPFGQGTKLTVLG

SEQ ID NO. 97: 610 max
EIVMTQSPSTLSASVGDRVIITCQASQSISSWLSWYQQKPGKAPKLLIYQASTLASGVPSRFSGSGSG

TEFTLTISSLQPDDFATYYCQNNYGFRSYGGAFGQGTKLTVLG

SEQ ID NO. 98: 578 max
EIVMTQSPSTLSASVGDRVIITCQASEIIHSWLAWYQQKPGKAPKLLIYLASTLASGVPSRFSGSGSGT

QFTLTISSLQPDDFATYYCQNVYLASTNGANFGQGTKLTVLG

SEQ ID NO. 99: 534 max
EIVMTQSPSTLSASVGDRVIITCQASQSINIWLSWYQQKPGKAPKLLIYKESTLASGVPSRFSGSGSGT

EFTLTISSLQPDDFATYYCQNNYDSGNNGFPFGQGTKLTVLG

SEQ ID NO. 100: 567 max
EIVMTQSPSTLSASVGDRVIITCQADQSIYIWLSWYQQKPGKAPKLLIYKASTLESGVPSRFSGSGSGT

QFTLTISSLQPDDFATYYCQNNAHYSTNGGTFGQGTKLTVLG

SEQ ID NO. 101: 509 max
EIVMTQSPSTLSASVGDRVIITCQASQNIRIWLSWYQQKPGKAPKLLIYKASTLESGVPSRFSGSGSGT

EFTLTISSLQPDDFATYYCQNNAHYSTNGGTFGQGTKLTVLG

SEQ ID NO. 102: 511 max
EIVMTQSPSTLSASVGDRVIITCQASQSINIWLSWYQQKPGKAPKLLIYRASTLASGVPSRFSGSGSGT

EFTLTISSLQPDDFATYYCQANYAYSAGYGAAFGQGTKLTVLG

SEQ ID NO. 103: 578 max_Pref subst
EIVMTQSPSSLSASVGDRVTITCQASEIIHSWLAWYQQRPGKAPKLLISLASTLASGVPSRFSGSGSGT

QFTFTISSLQPEDFAVYYCQNVYLASTNGANFGQGTKVEIKR

SEQ ID NO. 104: 578 min VL: E1D
DIVMTQSPSTLSASVGDRVIITCQASEIIHSWLAWYQQKPGKAPKLLIYLASTLASGVPSRFSGSGSGA

EFTLTISSLQPDDFATYYCQNVYLASTNGANFGQGTKLTVLG

SEQ ID NO. 105: 578 min VL: I2V
EVVMTQSPSTLSASVGDRVIITCQASEIIHSWLAWYQQKPGKAPKLLIYLASTLASGVPSRFSGSGSG

AEFTLTISSLQPDDFATYYCQNVYLASTNGANFGQGTKLTVLG

SEQ ID NO. 106: 511 min VL: C41L
EIVMTQSPSTLSASVGDRVIITCQASQSINIWLSWYQQKPGKAPKLLIYRASTLASGVPSRFSGSGSG

AEFTLTISSLQPDDFATYYCQANYAYSAGYGAAFGQGTKLTVLG

VH sequences:
SEQ ID NO. 107: 60-11-4
QSLEESGGDLVKPGASLTLTCTASGFPFSSGYWVCWVRQAPGKGLEWIACIYAGSSGSTYYASWAK

GRFTISKTSSTTVTLQMTSLTAADTATYFCARGNNYYIYTDGGYAYAGLELWGPGILVTVSS

SEQ ID NO. 108: 60-11-6
QSLEESGGDLVKPGASLTLTCTASGFSFSSGYWICWVRQAPGKGLEWIACIYAGSSGSTYYASWAKG

RFTISKTSSTTVTLQMTSLTAADTATYFCARGNNYYIYTDGGYAYAGLELWGPGILVTVSS

SEQ ID NO. 109: 435
QSLEESGGDLVQPGASLTLTCKVSGFSLNTNYWMCWVRQAPGKGLEWIGCMYTGSYNRAYYASW

AKGRFTSSKTSSTTVTLEMTSLTAADTATYFCAKGSNWYSDLWGPGTLVTVSS

SEQ ID NO. 110: 453
QERLVESGGGLVQPEGSLTLTCKASGFSFSRSYYIYWVRQAPGKGLEWIACIDAGSSGILVYANWAK

GRFTISKTSSTTVTLQMTSLTAADTATYFCARGDASYGVDSFMLPLWGPGTLVTVSS

-continued

SEQ ID NO. 111: 375
QSLEESGGGLVQPEGSLTLTCKASGFSFTTTDYMCWVRQAPGKGLEWIGCILAGDGSTYYANWAK

GRFTGSKTSSTTVDLKMTGLTAADTATYFCARSDPASSWSFALWGPGTLVTVSS

SEQ ID NO. 112: 610
QSLEESGGRLVTPGTPLTLTCTASGIDFSGAYYMGWVRQAPGKGLEWIGYIDYDGDRYYASWAKG

RFTISKTSTTVDLKITSPTTEDTATYFCARSDYSSGWGTDIWGPGTLVTVSL

SEQ ID NO. 113: 578
QSVEESGGRLVTPGTPLTLTCTASGFSLTDYYYMTWVRLAPGKGLEYIGFIDPDDDPYYATWAKGRF

TISRTSTTVNLKMTSPTTEDTATYFCAGGDHNSGWGLDIWGPGTLVTVSL

SEQ ID NO. 114: 534
QSLEESGGRLVTPGTPLTLTCTASGFSLSYYYMSWVRQAPGKGLEWIGIIGPGDYTDYASWAKGRFT

ISKTSTTVDLKITSPTTEDTATYFCGRGDDNSGWGEDIWGPGTLVTVSL

SEQ ID NO. 115: 567
QSVEESGGRLVTPGAPLTLTCSVSGFSLSDYYMCWVRQAPGKGLQWIGCLDYFGSTDDASWAKGR

FTISKTSTAVDLKITSPTTEDTATYFCARTDDSRGWGLNIWGPGTLVTVSL

SEQ ID NO. 116: 509
QSLEESGGRLVTPGTPLTLTCTASGFSLSSYYMCWVRQAPGKGLEWIGCLDYVGDTDYASWAKGRF

TISKASTTVDLKITSLTTEDTATYFCARTDDSRGWGLNIWGPGTLVTVSL

SEQ ID NO. 117: 511
QSVEESGGRLVTPGTPLTLTCTVSGFSLNTYYMNWVRQAPGKGLEWIGIIAPDDTTYYASWAKSRST

ITRDTNENTVTLKMTSLTTEDTATYFCARSGDTTAWGADIWGPGTLVTVSL

SEQ ID NO. 118: 60-11-4 min
EVQLVESGGGLVQPGGSLRLSCAASGFPFSSGYWVCWVRQAPGKGLEWVSCIYAGSSGSTYYASW

AKGRFTISRDNSKNTLYLQMNSLRAEDTAVYYCAKGNNYYIYTDGGYAYAGLELWGQGTLVTVSS

SEQ ID NO. 119: 60-11-6 min
EVQLVESGGGLVQPGGSLRLSCAASGFSFSSGYWICWVRQAPGKGLEWVSCIYAGSSGSTYYASW

AKGRFTISRDNSKNTLYLQMNSLRAEDTAVYYCAKGNNYYIYTDGGYAYAGLELWGQGTLVTVSS

SEQ ID NO. 120: 435 min
EVQLVESGGGLVQPGGSLRLSCAASGFSLNTNYWMCWVRQAPGKGLEWVSCMYTGSYNRAYYA

SWAKGRFTISRDNSKNTLYLQMNSLRAEDTAVYYCAKGSNWYSDLWGQGTLVTVSS

SEQ ID NO. 121: 453 min
EVQLVESGGGLVQPGGSLRLSCAASGFSFSRSYYIYWVRQAPGKGLEWVSCIDAGSSGILVYANWA

KGRFTISRDNSKNTLYLQMNSLRAEDTAVYYCAKGDASYGVDSFMLPLWGQGTLVTVSS

SEQ ID NO. 122: 375 min
EVQLVESGGGLVQPGGSLRLSCAASGFSFTTTDYMCWVRQAPGKGLEWVSCILAGDGSTYYANW

AKGRFTISRDNSKNTLYLQMNSLRAEDTAVYYCAKSDPASSWSFALWGQGTLVTVSS

SEQ ID NO. 123: 610 min
EVQLVESGGGLVQPGGSLRLSCAASGIDFSGAYYMGWVRQAPGKGLEWVSYIDYDGDRYYASWA

KGRFTISRDNSKNTLYLQMNSLRAEDTAVYYCAKSDYSSGWGTDIWGQGTLVTVSS

SEQ ID NO. 124: 578 min
EVQLVESGGGLVQPGGSLRLSCAASGFSLTDYYYMTWVRQAPGKGLEWVSFIDPDDDPYYATWAK

GRFTISRDNSKNTLYLQMNSLRAEDTAVYYCAKGDHNSGWGLDIWGQGTLVTVSS

SEQ ID NO. 125: 534 min
EVQLVESGGGLVQPGGSLRLSCAASGFSLSYYYMSWVRQAPGKGLEWVSIIGPGDYTDYASWAKG

RFTISRDNSKNTLYLQMNSLRAEDTAVYYCAKGDDNSGWGEDIWGQGTLVTVSS

SEQ ID NO. 126: 567 min
EVQLVESGGGLVQPGGSLRLSCAASGFSLSDYYMCWVRQAPGKGLEWVSCLDYFGSTDDASWAK

GRFTISRDNSKNTLYLQMNSLRAEDTAVYYCAKTDDSRGWGLNIWGQGTLVTVSS

-continued

SEQ ID NO. 127: 509 min
EVQLVESGGGLVQPGGSLRLSCAASGFSLSSYYMCWVRQAPGKGLEWVSCLDYVGDTDYASWAK

GRFTISRDNSKNTLYLQMNSLRAEDTAVYYCAKTDDSRGWGLNIWGQGTLVTVSS

SEQ ID NO. 128: 511 min
EVQLVESGGGLVQPGGSLRLSCAASGFSLNTYYMNWVRQAPGKGLEWVSIIAPDDTTYYASWAKS

RFTISRDNSKNTLYLQMNSLRAEDTAVYYCAKSGDTTAWGADIWGQGTLVTVSS

SEQ ID NO. 129: 578 min_Pref subst
substQVQLVQTGGGLVQPGGSLRLSCAASGFSLTDYYYMTWVRQAPGKGLEWVSFIDPDDDPYY

ATWAKGRFTISRDNSKNTVYLQMNSLRAEDTALYYCAKGDHNSGWGLDIWGQGTLVTVSS

SEQ ID NO. 130: 60-11-4 max
EVQLVESGGGLVQPGGSLRLSCTASGFPFSSGYWVCWVRQAPGKGLEWVGCIYAGSSGSTYYASW

AKGRFTISKDTSKNTVYLQMNSLRAEDTAVYYCARGNNYYIYTDGGYAYAGLELWGQGTLVTVSS

SEQ ID NO. 131: 60-11-6 max
EVQLVESGGGLVQPGGSLRLSCTASGFSFSSGYWICWVRQAPGKGLEWVGCIYAGSSGSTYYASW

AKGRFTISKDTSKNTVYLQMNSLRAEDTAVYYCARGNNYYIYTDGGYAYAGLELWGQGTLVTVSS

SEQ ID NO. 132: 435 max
EVQLVESGGGLVQPGGSLRLSCKVSGFSLNTNYWMCWVRQAPGKGLEWVGCMYTGSYNRAYYA

SWAKGRFTSSKDTSKNTVYLQMNSLRAEDTAVYYCAKGSNWYSDLWGQGTLVTVSS

SEQ ID NO. 133: 453 max
EVQLVESGGGLVQPGGSLRLSCKASGFSFSRSYYIYWVRQAPGKGLEWVGCIDAGSSGILVYANWA

KGRFTISKDTSKNTVYLQMNSLRAEDTAVYYCARGDASYGVDSFMLPLWGQGTLVTVSS

SEQ ID NO. 134: 375 max
EVQLVESGGGLVQPGGSLRLSCKASGFSFTTTDYMCWVRQAPGKGLEWVGCILAGDGSTYYANW

AKGRFTGSKDTSKNTVYLQMNSLRAEDTAVYYCARSDPASSWSFALWGQGTLVTVSS

SEQ ID NO. 135: 610 max
EVQLVESGGGLVQPGGSLRLSCTASGIDFSGAYYMGWVRQAPGKGLEWVGYIDYDGDRYYASWA

KGRFTISKDTSKNTVYLQMNSLRAEDTAVYYCARSDYSSGWGTDIWGQGTLVTVSS

SEQ ID NO. 136: 578 max
EVQLVESGGGLVQPGGSLRLSCTASGFSLTDYYYMTWVRQAPGKGLEWVGFIDPDDDPYYATWA

KGRFTISRDTSKNTVYLQMNSLRAEDTAVYYCAGGDHNSGWGLDIWGQGTLVTVSS

SEQ ID NO. 137: 534 max
EVQLVESGGGLVQPGGSLRLSCTASGFSLSYYYMSWVRQAPGKGLEWVGIIGPGDYTDYASWAKG

RFTISKDTSKNTVYLQMNSLRAEDTAVYYCARGDDNSGWGEDIWGQGTLVTVSS

SEQ ID NO. 138: 567 max
EVQLVESGGGLVQPGGSLRLSCSVSGFSLSDYYMCWVRQAPGKGLEWVGCLDYFGSTDDASWAK

GRFTISKDTSKNTVYLQMNSLRAEDTAVYYCARTDDSRGWGLNIWGQGTLVTVSS

SEQ ID NO. 139: 509 max
EVQLVESGGGLVQPGGSLRLSCTASGFSLSSYYMCWVRQAPGKGLEWVGCLDYVGDTDYASWAK

GRFTISKDASKNTVYLQMNSLRAEDTAVYYCARTDDSRGWGLNIWGQGTLVTVSS

SEQ ID NO. 140: 509 maxII
EVQLVESGGGLVQPGGSLRLSCTASGFSLSSYYMSWVRQAPGKGLEWVGILDYVGDTDYASWAKG

RFTISKDASKNTVYLQMNSLRAEDTAVYYCARTDDSRGWGLNIWGQGTLVTVSS

SEQ ID NO. 141: 511 max
EVQLVESGGGLVQPGGSLRLSCTVSGFSLNTYYMNWVRQAPGKGLEWVGIIAPDDTTYYASWAKS

RSTISRDTSKNTVYLQMNSLRAEDTAVYYCARSGDTTAWGADIWGQGTLVTVSS

SEQ ID NO. 142: 578 max_Pref subst
substQVQLVQTGGGLVQPGGSLRLSCTASGFSLTDYYYMTWVRQAPGKGLEWVGFIDPDDDPYY

ATWAKGRFTISRDTSKNTVYLQMNSLRAEDTALYYCAGGDHNSGWGLDIWGQGTLVTVSS

SEQ ID NO. 143: 567 minDHP
EVQLVESGGGSVQPGGSLRLSCAASGFSLSDYYMCWVRQAPGKGLEWVSCLDYFGSTDDASWAK

GRFTISRDNSKNTLYLQMNSLRAEDTATYYCAKTDDSRGWGLNIWGQGTTVTVSS

SEQ ID NO. 144: 578 maxDHP
EVQLVESGGGSVQPGGSLRLSCTASGFSLTDYYYMTWVRQAPGKGLEWVGFIDPDDDPYYATWA

KGRFTISRDTSKNTVYLQMNSLRAEDTATYYCAGGDHNSGWGLDIWGQGTTVTVSS

SEQ ID NO. 145: 511 maxDHP
EVQLVESGGGSVQPGGSLRLSCTVSGFSLNTYYMNWVRQAPGKGLEWVGIIAPDDTTYYASWAKS

RSTISRDTSKNTVYLQMNSLRAEDTATYYCARSGDTTAWGADIWGQGTTVTVSS

SEQ ID NO. 146: 578 max_Pref subst_DHP
QVQLVQTGGGSVQPGGSLRLSCTASGFSLTDYYYMTWVRQAPGKGLEWVGFIDPDDDPYYATWA

KGRFTISRDTSKNTVYLQMNSLRAEDTATYYCAGGDHNSGWGLDIWGQGTTVTVSS

SEQ ID NO. 147: 578 max VH: E1_
VQLVESGGGLVQPGGSLRLSCTASGFSLTDYYYMTWVRQAPGKGLEWVGFIDPDDDPYYATWAK

GRFTISRDTSKNTVYLQMNSLRAEDTAVYYCAGGDHNSGWGLDIWGQGTLVTVSS

SEQ ID NO. 148: 578 max VH: V2Q
EQQLVESGGGLVQPGGSLRLSCTASGFSLTDYYYMTWVRQAPGKGLEWVGFIDPDDDPYYATWA

KGRFTISRDTSKNTVYLQMNSLRAEDTAVYYCAGGDHNSGWGLDIWGQGTLVTVSS

SEQ ID NO. 149: 578 max VH: Q46L
EVQLVESGGGLVQPGGSLRLSCTASGFSLTDYYYMTWVRLAPGKGLEWVGFIDPDDDPYYATWAK

GRFTISRDTSKNTVYLQMNSLRAEDTAVYYCAGGDHNSGWGLDIWGQGTLVTVSS

SEQ ID NO. 150: 578 max VH: W54Y
EVQLVESGGGLVQPGGSLRLSCTASGFSLTDYYYMTWVRQAPGKGLEYVGFIDPDDDPYYATWAK

GRFTISRDTSKNTVYLQMNSLRAEDTAVYYCAGGDHNSGWGLDIWGQGTLVTVSS

SEQ ID NO. 151: 578 max VH: V55I
EVQLVESGGGLVQPGGSLRLSCTASGFSLTDYYYMTWVRQAPGKGLEWIGFIDPDDDPYYATWAK

GRFTISRDTSKNTVYLQMNSLRAEDTAVYYCAGGDHNSGWGLDIWGQGTLVTVSS

SEQ ID NO. 152: 578 max VH: D83A
EVQLVESGGGLVQPGGSLRLSCTASGFSLTDYYYMTWVRQAPGKGLEWVGFIDPDDDPYYATWA

KGRFTISRATSKNTVYLQMNSLRAEDTAVYYCAGGDHNSGWGLDIWGQGTLVTVSS

SEQ ID NO. 153: 578 max VH: N87A
EVQLVESGGGLVQPGGSLRLSCTASGFSLTDYYYMTWVRQAPGKGLEWVGFIDPDDDPYYATWA

KGRFTISRDTSKATVYLQMNSLRAEDTAVYYCAGGDHNSGWGLDIWGQGTLVTVSS

SEQ ID NO. 154: 578 max VH: Y105F
EVQLVESGGGLVQPGGSLRLSCTASGFSLTDYYYMTWVRQAPGKGLEWVGFIDPDDDPYYATWA

KGRFTISRDTSKNTVYLQMNSLRAEDTAVYFCAGGDHNSGWGLDIWGQGTLVTVSS

SEQ ID NO. 155: 578 max VH: D83_
EVQLVESGGGLVQPGGSLRLSCTASGFSLTDYYYMTWVRQAPGKGLEWVGFIDPDDDPYYATWA

KGRFTISRTSKNTVYLQMNSLRAEDTAVYYCAGGDHNSGWGLDIWGQGTLVTVSS

SEQ ID NO. 156: 578 max VH: N87_
EVQLVESGGGLVQPGGSLRLSCTASGFSLTDYYYMTWVRQAPGKGLEWVGFIDPDDDPYYATWA

KGRFTISRDTSKTVYLQMNSLRAEDTAVYYCAGGDHNSGWGLDIWGQGTLVTVSS

SEQ ID NO. 157: 578 max VH: T84N
EVQLVESGGGLVQPGGSLRLSCTASGFSLTDYYYMTWVRQAPGKGLEWVGFIDPDDDPYYATWA

KGRFTISRDNSKNTVYLQMNSLRAEDTAVYYCAGGDHNSGWGLDIWGQGTLVTVSS

SEQ ID NO. 158: 578 max VH: V89L
EVQLVESGGGLVQPGGSLRLSCTASGFSLTDYYYMTWVRQAPGKGLEWVGFIDPDDDPYYATWA

KGRFTISRDTSKNTLYLQMNSLRAEDTAVYYCAGGDHNSGWGLDIWGQGTLVTVSS

SEQ ID NO. 159: 578 max VH: V89A
EVQLVESGGGLVQPGGSLRLSCTASGFSLTDYYYMTWVRQAPGKGLEWVGFIDPDDDPYYATWA

KGRFTISRDTSKNTAYLQMNSLRAEDTAVYYCAGGDHNSGWGLDIWGQGTLVTVSS

SEQ ID NO. 160: 578 maxDHP VH: T84N
EVQLVESGGGSVQPGGSLRLSCTASGFSLTDYYYMTWVRQAPGKGLEWVGFIDPDDDPYYATWA

KGRFTISRDNSKNTVYLQMNSLRAEDTATYYCAGGDHNSGWGLDIWGQGTTVTVSS

SEQ ID NO. 161: 578 maxDHP VH: V89L
EVQLVESGGGSVQPGGSLRLSCTASGFSLTDYYYMTWVRQAPGKGLEWVGFIDPDDDPYYATWA

KGRFTISRDTSKNTLYLQMNSLRAEDTATYYCAGGDHNSGWGLDIWGQGTTVTVSS

SEQ ID NO. 162: 578 maxDHP VH: V89A
EVQLVESGGGSVQPGGSLRLSCTASGFSLTDYYYMTWVRQAPGKGLEWVGFIDPDDDPYYATWA

KGRFTISRDTSKNTAYLQMNSLRAEDTATYYCAGGDHNSGWGLDIWGQGTTVTVSS

SEQ ID NO. 163: 578 max VH: T84N, V89A
EVQLVESGGGLVQPGGSLRLSCTASGFSLTDYYYMTWVRQAPGKGLEWVGFIDPDDDPYYATWA

KGRFTISRDNSKNTAYLQMNSLRAEDTAVYYCAGGDHNSGWGLDIWGQGTLVTVSS

SEQ ID NO. 164: 578 max VH: T84N, V89L
EVQLVESGGGLVQPGGSLRLSCTASGFSLTDYYYMTWVRQAPGKGLEWVGFIDPDDDPYYATWA

KGRFTISRDNSKNTLYLQMNSLRAEDTAVYYCAGGDHNSGWGLDIWGQGTLVTVSS

SEQ ID NO. 165: 578 maxDHP VH: T84N, V89A
EVQLVESGGGSVQPGGSLRLSCTASGFSLTDYYYMTWVRQAPGKGLEWVGFIDPDDDPYYATWA

KGRFTISRDNSKNTAYLQMNSLRAEDTATYYCAGGDHNSGWGLDIWGQGTTVTVSS

SEQ ID NO. 166: 578 maxDHP VH: T84N, V89L
EVQLVESGGGSVQPGGSLRLSCTASGFSLTDYYYMTWVRQAPGKGLEWVGFIDPDDDPYYATWA

KGRFTISRDNSKNTLYLQMNSLRAEDTATYYCAGGDHNSGWGLDIWGQGTTVTVSS framework sequences (X residues are CDR insertion sites and may
be any naturally occurring amino acid. At least 3 and up to 50
amino acids can be present):
SEQ ID NO. 167: Variable light chain FW1.4 and rFW1.4
EIVMTQSPSTLSASVGDRVIITC(X)$_{n=3-50}$ WYQQKPGKAPKLLIY(X)$_{n=3-50}$ GVPSRFSGSGSGAEFTLTISSLQPDDFATYYC(X)$_{n=3-50}$ FGQGTKLT VLG SEQ ID NO. 168: Variable light chain rFW1.4 variant 2 (v2)
EIVMTQSPSTLSASVGDRVIITC(X)$_{n=3-50}$ WYQQKPGKAPKLLIY(X)$_{n=3-50}$ GVPSRFSGSGSGAEFTLTISSLQPDDFATYYC(X)$_{n=3-50}$ FGQGTKLT VLG SEQ ID NO. 169: Variable heavy chain FW1.4
EVQLVESGGGLVQPGGSLRLSCAAS(X)$_{n=3-50}$ WVRQAPGKGLEWVS(X)$_{n=3-50}$ RFTISRDNSKNTLYLQMNSLRAEDTAVYYCAK(X)$_{n=3-50}$ WGQGTL VTVSS SEQ ID NO. 170: Variable heavy chain rFW1.4
EVQLVESGGGLVQPGGSLRLSCTAS(X)$_{n=3-50}$ WVRQAPGKGLEWVG(X)$_{n=3-50}$ RFTISRDTSKNTVYLQMNSLRAEDTAVYYCAR(X)$_{n=3-50}$ WGQGTLV TVS SEQ ID NO. 171: Variable heavy chain rFW1.4 variant 2 (v2)
EVQLVESGGGLVQPGGSLRLSCTVS(X)$_{n=3-50}$ WVRQAPGKGLEWVG(X)$_{n=3-50}$ RFTISKDTSKNTVYLQMNSLRAEDTAVYYCAR(X)$_{n=3-50}$ WGQGTLVTVSS ScFv framework sequences:
SEQ ID NO. 172: FW1.4
EIVMTQSPSTLSASVGDRVIITC(X)$_{n=3-50}$ WYQQKPGKAPKLLIY(X)$_{n=3-50}$ GVPSRFSGSGSGAEFTLTISSLQPDDFATYYC(X)$_{n=3-50}$ FGQGTKLTVLG GGGGSGGGGSGGGGSGGGGSEVQLVESGGGLVQPGGSLRLSCAAS(X)$_{n=3-50}$ WVRQAPGKGLEWVS(X)$_{n=3-50}$ RFTISRDNSKNTLYLQMNSLRAEDTA VYYCAK(X)$_{n=3-50}$

WGQGTLVTVSS

-continued

SEQ ID NO. 173: rFW1.4
EIVMTQSPSTLSASVGDRVIITC(X)$_{n=3-50}$ WYQQKPGKAPKLLIY(X)$_{n=3-50}$

GVPSRFSGSGSGTEFTLTISSLQPDDFATYYC(X)$_{n=3-50}$ FGQGTKLTVLG

GGGGSGGGGSGGGGSGGGGSEVQLVESGGGLVQPGGSLRLSCTAS(X)n$_{=3-50}$

WVRQAPGKGLEWVG(X)$_{n=3-50}$ RFTISRDTSKNTVYLQMNS LRAEDTAVYYCAR(X)$_{n=3-50}$

WGQGTLVTVSS

SEQ ID NO. 174: rFW1.4 variant 2 (v2)
EIVMTQSPSTLSASVGDRVIITC(X)$_{n=3-50}$ WYQQKPGKAPKLLIY(X)$_{n=3-50}$ GVPSRFSGSGSGTEFTLTISSLQPDDFATYYC(X)$_{n=3-50}$ FGQGTKLTVLG GGGGSGGGGSGGGGSGGGGS EVQLVESGGGLVQPGGSLRLSCTVS(X)$_{n=3-50}$ WVRQAPGKGLEWVG(X)$_{n=3-50}$ RFTISKDTSKNTVYLQMNSLR AEDTAVYYCAR(X)$_{n=3-50}$

WGQGTLVTVSS

ScFv anti-VEGF sequences:
SEQ ID NO. 175: 435_max
EIVMTQSPSTLSASVGDRVIITCQASQSIGSSLAWYQQKPGKAPKLLIYTAANLASGVPSRFSGSRSG

AEFTLTISSLQPDDFATYYCQNFATSDTVTFGQGTKLTVLGGGGGSGGGGSGGGGSGGGGSEVQL

VESGGGLVQPGGSLRLSCKASGFSLNTNYWMCWVRQAPGKGLEWVGCMYTGSYNRAYYASWA

KGRFTSSKDTSKNTVYLQMNSLRAEDTAVYYCAKGSNWYSDLWGQGTLVTVSS

SEQ ID NO. 176: 511_max
EIVMTQSPSTLSASVGDRVIITCQASQSINIWLSWYQQKPGKAPKLLIYRASTLASGVPSRFSGSGSGT

EFTLTISSLQPDDFATYYCQANYAYSAGYGAAFGQGTKLTVLGGGGGSGGGGSGGGGSGGGGSEV

QLVESGGGLVQPGGSLRLSCTVSGFSLNTYYMNWVRQAPGKGLEWVGIIAPDDTTYYASWAKSRS

TISRDTSKNTVYLQMNSLRAEDTAVYYCARSGDTTAWGADIWGQGTLVTVSS

SEQ ID NO. 177: 567_min
EIVMTQSPSTLSASVGDRVIITCQADQSIYIWLSWYQQKPGKAPKLLIYKASTLESGVPSRFSGSGSGA

EFTLTISSLQPDDFATYYCQNNAHYSTNGGTFGQGTKLTVLGGGGGSGGGGSGGGGSGGGGSEVQ

LVESGGGLVQPGGSLRLSCAASGFSLSDYYMCWVRQAPGKGLEWVSCLDYFGSTDDASWAKGRFT

ISRDNSKNTLYLQMNSLRAEDTAVYYCAKTDDSRGWGLNIWGQGTLVTVSS

SEQ ID NO. 178: 578 min
EIVMTQSPSTLSASVGDRVIITCQASEIIHSWLAWYQQKPGKAPKLLIYLASTLASGVPSRFSGSGSGA

EFTLTISSLQPDDFATYYCQNVYLASTNGANFGQGTKLTVLGGGGGSGGGGSGGGGSGGGGSEVQ

LVESGGGLVQPGGSLRLSCAASGFSLTDYYYMTWVRQAPGKGLEWVSFIDPDDDPYYATWAKGRF

TISRDNSKNTLYLQMNSLRAEDTAVYYCAKGDHNSGWGLDIWGQGTLVTVSS

SEQ ID NO. 179: 578 max
EIVMTQSPSTLSASVGDRVIITCQASEIIHSWLAWYQQKPGKAPKLLIYLASTLASGVPSRFSGSGSGT

QFTLTISSLQPDDFATYYCQNVYLASTNGANFGQGTKLTVLGGGGGSGGGGSGGGGSGGGGSEVQ

LVESGGGLVQPGGSLRLSCTASGFSLTDYYYMTWVRQAPGKGLEWVGFIDPDDDPYYATWAKGRF

TISRDTSKNTVYLQMNSLRAEDTAVYYCAGGDHNSGWGLDIWGQGTLVTVSS

SEQ ID NO. 180: 578 minmax (E5BA903)
EIVMTQSPSTLSASVGDRVIITCQASEIIHSWLAWYQQKPGKAPKLLIYLASTLASGVPSRFSGSGSGA

EFTLTISSLQPDDFATYYCQNVYLASTNGANFGQGTKLTVLGGGGGSGGGGSGGGGSGGGGSEVQ

LVESGGGLVQPGGSLRLSCTASGFSLTDYYYMTWVRQAPGKGLEWVGFIDPDDDPYYATWAKGRF

TISRDTSKNTVYLQMNSLRAEDTAVYYCAGGDHNSGWGLDIWGQGTLVTVSS

SEQ ID No. 181 linker
GGGGSGGGGSGGGGSGGGGS

The invention claimed is:

1. A humanized antibody or antigen-binding fragment thereof comprising a variable heavy chain (VH), and a variable light chain (VL), wherein:
   the VH comprises CDRH1, CDRH2 and CDRH3 sequences of SEQ ID NO: 8, SEQ ID NO: 20 and SEQ ID NO: 32, respectively, and the VL comprises CDRL1, CDRL2, and CDRL3 sequences of SEQ ID NO: 43, SEQ ID NO: 55 and SEQ ID NO: 66, wherein the antibody or antigen-binding fragment thereof binds human VEGF$_{165}$ with an affinity ($K_d$) of $\leq 1\times10^{-9}$ M.

2. The humanized antibody or antigen-binding fragment thereof of claim 1, wherein the fragment is an scFv, a Fab fragment, a Fab' fragment, or a F(ab')$_2$ fragment.

3. A composition comprising the humanized antibody or antigen-binding fragment of claim 1, and a pharmaceutically acceptable carrier.

4. The composition of claim 3, formulated for topical, intraocular, oral, nasal, rectal or parental administration.

5. The humanized antibody or antigen-binding fragment of claim 1 comprising a heavy chain variable region variable region framework sequence having at least 95% sequence identity to the sequence of SEQ ID NO: 164.

6. The humanized antibody or antigen-binding fragment of claim 5, wherein the heavy chain variable region framework comprises a sequence having 100% identity to SEQ ID NO: 164.

7. The humanized antibody or antigen-binding fragment of claim 1, comprising a light chain variable region framework sequence having at least 95% sequence identity to the sequence of SEQ ID NO: 87.

8. The humanized antibody or antigen-binding fragment of claim 7, wherein the light chain variable region framework comprises a sequence having 100% identity to SEQ ID NO: 87.

9. The humanized antibody or antigen-binding fragment of claim 1, wherein the antibody or antigen-binding fragment comprises a variable heavy chain comprises the sequence of SEQ ID NO: 164 and wherein the antibody or antigen-binding fragment comprises a variable light chain comprising the sequence of SEQ ID NO: 87.

10. The humanized antibody or antigen-binding fragment of claim 9, further comprising a linker sequence having the sequence of SEQ ID NO: 181 linking the heavy chain variable region and the light chain variable region.

11. The antigen-binding fragment of claim 10, which is a single-chain antibody (scFv).

12. The antigen-binding fragment of claim 11, comprising an N-terminal methionine derived from a start codon present in an expression vector that expresses the antigen-binding fragment.

13. The humanized antibody or antigen-binding fragment of claim 5, 6, 7, 8, 9, 10, 11, or 12, wherein the antibody or antigen-binding fragment thereof binds human VEGF$_{165}$ with an affinity ($K_d$) of $\leq 1\times10^{-10}$ M.

14. A composition comprising the humanized antibody or antigen-binding fragment of claim 13, and a pharmaceutically acceptable carrier.

* * * * *